United States Patent
Yasuda et al.

(10) Patent No.: US 10,522,763 B2
(45) Date of Patent: Dec. 31, 2019

(54) DICYANOPYRAZINE COMPOUND, LUMINESCENT MATERIAL, LUMINESCENCE DEVICE USING THE SAME, AND METHOD FOR PRODUCING 2,5-DICYANO-3,6-DIHALOGENOPYRAZINE

(71) Applicants: KYUSHU UNIVERSITY, NATIONAL UNIVERSITY CORPORATION, Fukuoka-shi, Fukuoka (JP); NIPPON SODA CO., LTD., Tokyo (JP)

(72) Inventors: Takuma Yasuda, Fukuoka (JP); In Seob Park, Fukuoka (JP); Yu Seok Yang, Fukuoka (JP); Hiroshi Sumiya, Takaoka (JP); Yukio Fukushima, Kurashiki (JP)

(73) Assignees: KYUSHU UNIVERSITY, NATIONAL UNIVERSIT CORPORATION, Fukuoka-shi (JP); NIPPON SODA CO., LTD., Tokyo (JP)

( * ) Notice: Subject to any disclaimer, the term of this patent is extended or adjusted under 35 U.S.C. 154(b) by 0 days.

(21) Appl. No.: 16/260,725

(22) Filed: Jan. 29, 2019

(65) Prior Publication Data
US 2019/0169170 A1 Jun. 6, 2019

Related U.S. Application Data

(62) Division of application No. 15/769,578, filed as application No. PCT/JP2016/083095 on Nov. 8, 2016.

(30) Foreign Application Priority Data

Nov. 10, 2015 (JP) .................. 2015-220371
Dec. 11, 2015 (JP) .................. 2015-242690

(51) Int. Cl.
*H01L 51/00* (2006.01)
*H01L 51/50* (2006.01)
(Continued)

(52) U.S. Cl.
CPC ........ *H01L 51/0067* (2013.01); *C07D 241/24* (2013.01); *C07D 401/14* (2013.01);
(Continued)

(58) Field of Classification Search
CPC .. C07D 401/14; C07D 413/14; C07D 403/14; C07D 241/24; C07D 417/14;
(Continued)

(56) References Cited

U.S. PATENT DOCUMENTS

| 4,592,857 A | 6/1986 | Sugimori et al. |
| 5,294,711 A | 3/1994 | Tazaki et al. |
| 5,904,994 A | 5/1999 | Dodabalapur et al. |

FOREIGN PATENT DOCUMENTS

| CN | 101514262 A | 8/2009 |
| CN | 101723907 A | 6/2010 |

(Continued)

OTHER PUBLICATIONS

Chew, et al., Photoluminescence and Electroluminescence of a Novel Green-yellow Emitting Material—5,6-bis-[4-naphthalene-1-yl-phenyl-amino)-phenyl]-pyrazine-2,3-dicarbonitrile, J. of Luminescence 124, 221-227 (2007). (Year: 2007).*

(Continued)

*Primary Examiner* — Erich A Leeser
(74) *Attorney, Agent, or Firm* — Oliff PLC

(57) ABSTRACT

A compound represented by formula (I) or formula (II):

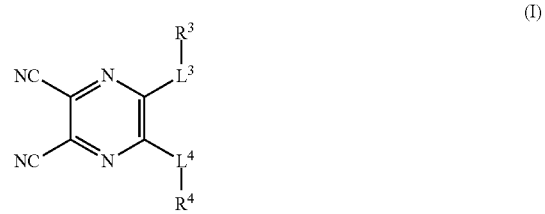

(I)

in formula (I), $R^3$ represents an electron donating group, $R^4$ represents a hydrogen atom, a substituted or unsubstituted aryl group or an electron donating group, $L^3$ represents a substituted or unsubstituted heteroarylene group or a substituted or unsubstituted arylene group, $L^4$ represents a single bond, a substituted or unsubstituted heteroarylene group or a substituted or unsubstituted arylene group, $L^3$ and $L^4$ may bond together to form a ring with the carbon atoms to which they are bonded,

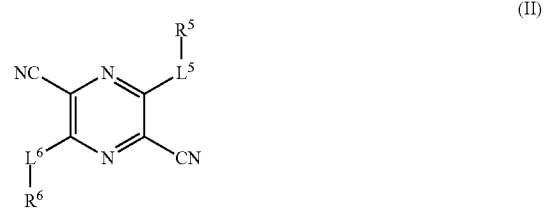

(II)

in formula (II), $R^5$ represents an electron donating group, $R^6$ represents a hydrogen atom, a substituted or unsubstituted aryl group or an electron donating group, $L^5$ represents a substituted or unsubstituted heteroarylene (Continued)

group or a substituted or unsubstituted arylene group, $L^6$ represents a single bond, a substituted or unsubstituted heteroarylene group or a substituted or unsubstituted arylene group.

4 Claims, 13 Drawing Sheets

(51) Int. Cl.
| | |
|---|---|
| *C07D 401/14* | (2006.01) |
| *C07D 413/14* | (2006.01) |
| *C07D 403/14* | (2006.01) |
| *C07D 241/24* | (2006.01) |
| *C07D 417/14* | (2006.01) |
| *C09K 11/06* | (2006.01) |

(52) U.S. Cl.
CPC ......... *C07D 403/14* (2013.01); *C07D 413/14* (2013.01); *C07D 417/14* (2013.01); *C09K 11/06* (2013.01); *H01L 51/0061* (2013.01); *H01L 51/0068* (2013.01); *H01L 51/0072* (2013.01); *H01L 51/50* (2013.01); *C09K 2211/1018* (2013.01); *H01L 51/5012* (2013.01)

(58) Field of Classification Search
CPC ............ C09K 11/06; C09K 2211/1018; H01L 51/0067; H01L 51/50; H01L 51/0061; H01L 51/0068; H01L 51/0072; H01L 51/5012
See application file for complete search history.

(56) References Cited

FOREIGN PATENT DOCUMENTS

| CN | 102634333 A | 8/2012 |
|---|---|---|
| CN | 104830320 A | 8/2015 |
| EP | 1749822 A1 | 2/2007 |
| JP | 55-022609 A | 2/1980 |
| JP | 55-079307 A | 6/1980 |
| JP | 55-115874 A | 9/1980 |
| JP | 56-002971 A | 1/1981 |
| JP | 56-002973 A | 1/1981 |
| JP | 60-084273 A | 5/1985 |
| JP | 61-241727 A | 10/1986 |
| JP | 62-000071 A | 1/1987 |
| JP | 62-010183 A | 1/1987 |
| JP | 63-077864 A | 4/1988 |
| JP | 01-252295 A | 10/1989 |
| JP | 05-032640 A | 2/1993 |
| JP | 06-100566 A | 4/1994 |
| JP | 09-188876 A | 7/1997 |
| JP | 11-138974 A | 5/1999 |
| JP | 2001-002661 A | 1/2001 |
| JP | 2001-089460 A | 4/2001 |
| JP | 2001-261658 A | 9/2001 |
| JP | 2006-241124 A | 9/2006 |
| JP | 2007-204443 A | 8/2007 |
| JP | 2009-503052 A | 1/2009 |
| JP | 2015-153864 A | 8/2015 |
| JP | 2015-172166 A | 10/2015 |
| KR | 10-2014-0027030 A | 3/2014 |
| WO | 88/01264 A1 | 2/1988 |
| WO | 91/03469 A1 | 3/1991 |
| WO | 2007/017758 A2 | 2/2007 |
| WO | 2011/055911 A1 | 5/2011 |

OTHER PUBLICATIONS

Mar. 20, 2019 Search Report issued in European Patent Application No. 16864207.2.
Wang et al: "Highly Efficient Near-Infrared Delayed Fluorescence Organic Light Emitting Diodes Using a Phenanthrene-Based Charge-Transfer Compound", Angewandte Chemie International Edition, vol. 54, No. 44, 26, Oct. 25, 2015, pp. 13068-13072.
Chew et al: "Photoluminescence and electroluminescence of a novel green-yellow emitting material-5,6-Bis-[4-(naphthalene-1-yl-phenyl-amino)-phenyl]-pyrazine-2,3-dicarbonitrile", Journal of Luminescence, Elsevier BV North-Holland, NL, vol. 124, No. 2, Nov. 29, 2006, pp. 221-227.
N. Sato et al., "Synthesis of 3,6-Dibromopyrazine-2,5-dicarbonitrile[1]," J. Heterocyclic. Chem., vol. 49, 675 (2012).
Begland et al., J. Org. Chem., vol. 39, No. 9, 1235 (1974).
N. Sato, Journal of Heterocyclic Chemistry, vol. 26, 817 (1989).
Feb. 14, 2017 International Search Report issued in International Application No. PCT/JP2016/083095.
Aug. 1, 2018 Office Action issued in U.S. Appl. No. 15/769,578.
Nov. 6, 2018 Office Action Issued in U.S. Appl. No. 15/769,578.

* cited by examiner

DICYANOPYRAZINE COMPOUND, LUMINESCENT MATERIAL, LUMINESCENCE DEVICE USING THE SAME, AND METHOD FOR PRODUCING 2,5-DICYANO-3,6-DIHALOGENOPYRAZINE

This is a Division of application Ser. No. 15/769,578, filed Apr. 19, 2018, which in turn is a national phase of PCT/JP2016/083095, filed Nov. 8, 2016, which claims the benefit of Japanese Patent Application No. 2015-220371, filed Nov. 10, 2015, and Japanese Patent Application No. 2015-242690, filed Dec. 11, 2015. The disclosure of the priority applications is hereby incorporated by reference herein in its entirety.

TECHNICAL FIELD

The present invention relates to a dicyanopyrazine compound, a luminescent material, a luminescence device using the same, and a method for producing a 2,5-dicyano-3,6-dihalogenopyrazine.

BACKGROUND ART

Several compounds among the compounds containing a dicyanopyrazine skeleton having an electron donating group are useful as electron transport materials, charge generating materials, optical recording materials, photoelectric conversion materials, luminescent materials, and the like.

For example, Patent Document 1 discloses an organic solid fluorescent substance containing N,N,N',N'-tetrakis(2-methylbenzyl)-2,5-diamino-3,6-pyrazinecarbonitrile crystal represented by formula (1), of which the maximum reflectance in a visible light region by a reflectance measurement of a post-dispersive spectroscopy is 100% or more.

[Chemical formula 1]

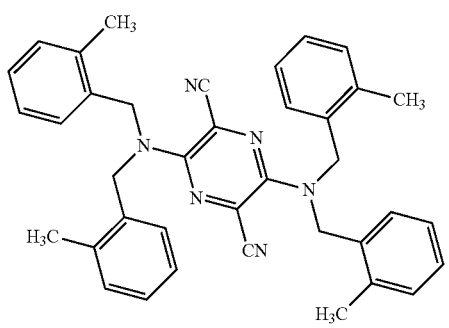

(1)

Patent Document 2 discloses a film obtained by adding a compound containing a quinoxaline skeleton represented by formula (3) or 2,3-dicyanopyrazine skeleton represented by formula (4) to 1,4,5,8,9,11-hexaazatriphenylene hexacarbonitrile represented by formula (2). The film seems to be usable for organic electronic devices such as organic electroluminescence devices, organic thin film solar cells or the like.

[Chemical formula 2]

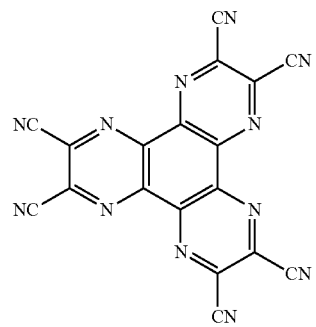

(2)

[Chemical formula 3]

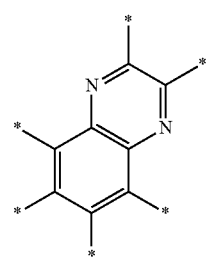

(3)

[Chemical formula 4]

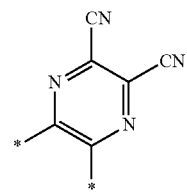

(4)

Patent Document 3 discloses an organic electroluminescence device having a layer containing a dicyanopyrazine compound represented by formula (5) between an anode and cathode which are opposite to each other.

[Chemical formula 5]

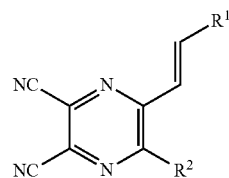

(5)

In formula (5), $R^1$ and $R^2$ each independently represent a heterocyclic group which may have a substituent or a hydrocarbon ring group which may have a substituent.)

Patent Document 4 discloses a compound represented by formula (6) or the like. The compound seems to be used for electron transport materials, charge generating materials, optical recording materials, photoelectric conversion materials, and the like.

[Chemical formula 6]

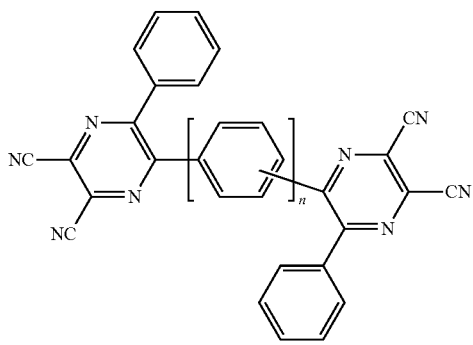
(6)

Patent Documents 5 and 6 disclose compounds represented by formula (7), Formula (8) and the like. These compounds seem to be usable for functional materials such as electroluminescence and wavelength conversion material or the like.

[Chemical formula 7]

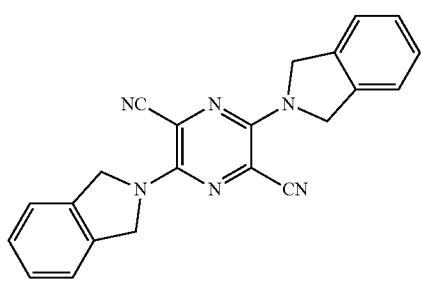
(7)

[Chemical formula 8]

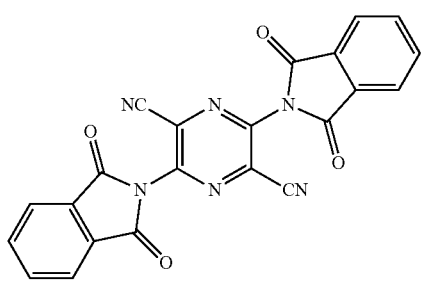
(8)

Patent Document 7 discloses a luminescent material including a compound in which a cyano pyridine as an electron attractive site and a heteroaryl group as an electron donating site are bonded.

There are various methods for producing a compound containing a dicyanopyrazine skeleton having an electron donating group. In order to obtain a compound containing a dicyanopyrazine skeleton having an electron donating group at a low cost and in a high yield, it is necessary to investigate starting materials and intermediates. Various candidates for starting materials or intermediates are conceivable. For example, a pyrazine compound having an amino group and a cyano group, such as 6-aminopyrazine-2,3,5-tricarbonitrile, 5,6-diaminopyrazine-2,3-dicarbonitrile, 3,5-diaminopyrazine-2,6-dicarbonitrile, 3,6-diaminopyrazine-2,5-dicarbonitrile or the like can be synthesized from a diamino maleonitrile or a homolog thereof as a starting material (see Non-Patent Document 2, Patent Document 8, Patent Document 9, etc.).

As the pyrazine compound having an amino group and a halogeno group, for example, 2-amino-6-chloropyrazine, 2-amino-5-chloropyrazine 2-amino-5-bromopyrazine and 2-amino-3,5-dibromopyrazine are commercially available and readily available. The 2-amino-bromopyrazines are likely to be synthesized by a method of reacting 2-aminopyrazines having at least one hydrogen atom in the pyrazine nucleus with bromine in the presence of a dehydrobromide agent in a solvent (Patent Document 11). This bromination is a substitution reaction of hydrogen to bromine.

As the pyrazine compound having a cyano group and a bromo group, for example, 2,5-dicyano-3,6-dibromopyrazine can be prepared from 2-cyano-3-aminopyrazine in a 4-step reaction or from 2-cyano-3-amino-6-bromopyrazine in 3-step reaction (Non-Patent Document 1). 2-cyano-3-aminopyrazine can be obtained by a method described in Non-Patent Document 3. A multi-step reaction is required for the synthesis of a pyrazine compound having a cyano group and a bromo group.

[Chemical formula 9]

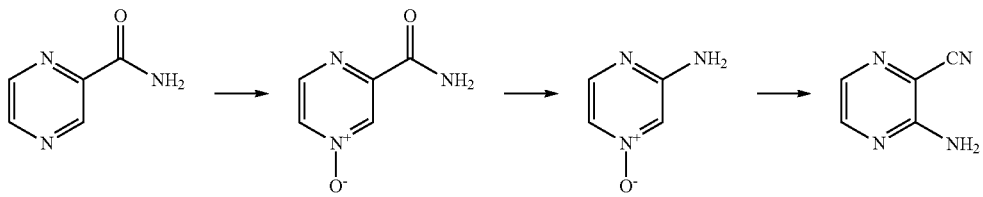

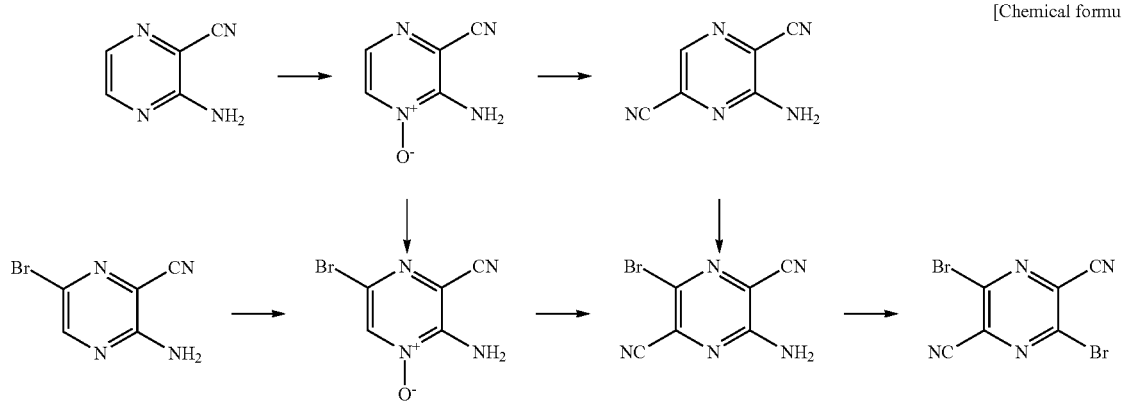

PRIOR ART LITERATURE

Patent Documents

[Patent Document 1] Japanese Unexamined Patent Application Publication No. 2007-204443
[Patent Document 2] Japanese Unexamined Patent Application Publication No. 2015-153864
[Patent Document 3] Japanese Unexamined Patent Application Publication No. 2001-261658
[Patent Document 4] Japanese Unexamined Patent Application Publication No. 2001-2661
[Patent Document 5] Japanese Unexamined Patent Application Publication No. Hei 5-32640
[Patent Document 6] Japanese Unexamined Patent Application Publication No. Hei 11-138974
[Patent Document 7] Japanese Unexamined Patent Application Publication No. 2015-172166
[Patent Document 8] Japanese Unexamined Patent Application Publication No. Sho 63-75909
[Patent Document 9] WO 91/03469 A
[Patent Document 10] WO 88/01264 A
[Patent Document 11] Japanese Unexamined Patent Application Publication No. 2001-89460

Non-Patent Document

Non-patent document 1: N. Sato et al., "Synthesis of 3,6-dibromopyrazine-2,5-dicarbonitrile", Journal of Heterocyclic Chemistry, Vol. 49, May 2012, 675
Non-patent document 2: J. Org. Chem., Vol. 39, 1235 (1974)
Non-patent document 3: Journal of Heterocyclic Chemistry, Vol. 26, 1989, 817

DISCLOSURE OF INVENTION

Problems to be Solved by the Invention

An object of the present invention is to provide a novel dicyanopyrazine compound and a luminescent material, and to provide a luminescence device using the luminescent material.

Further, it has been discovered that when a compound containing a dicyanopyrazine skeleton having a halogeno group, such as 2,5-dicyano-3,6-dibromopyrazine, is reacted with a compound capable of serving as an electron donating group, a compound containing a dicyanopyrazine skeleton having an electron donating group can be obtained in an extremely high yield.

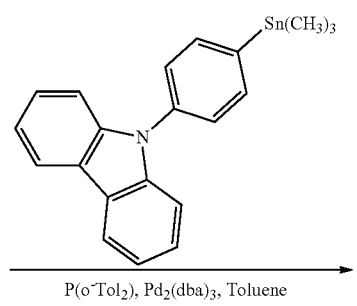

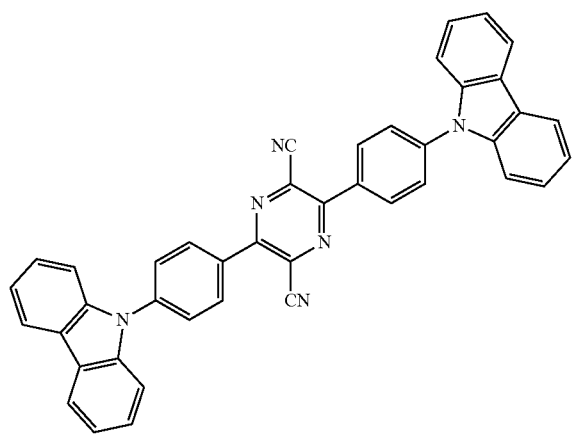

An object of the present invention is to provide a method for producing a 2,5-dicyano-3,6-dihalogenopyrazine, which is used in a method for producing a compound containing a dicyanopyrazine skeleton having an electron donating group, from an inexpensive starting material with less reaction steps and in a high yield Means for Solving the Problems As a result of intensive studies to solve the above problems, the present invention including the following embodiments has been completed.

That is, the present invention includes the following embodiments.

[1] A compound represented by formula (I) or formula (II),

[Chemical formula 13]

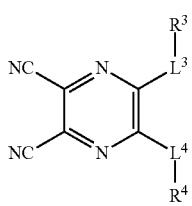

(I)

[In formula (I), $R^3$ represents an electron donating group, $R^4$ represents a hydrogen atom, a substituted or unsubstituted aryl group or an electron donating group, $L^3$ represents a substituted or unsubstituted heteroarylene group or a substituted or unsubstituted arylene group, $L^4$ represents a single bond, a substituted or unsubstituted heteroarylene group or a substituted or unsubstituted arylene group. $L^3$ and $L^4$ may bond together to form a ring with the carbon atoms to which they are bonded]

[Chemical formula 14]

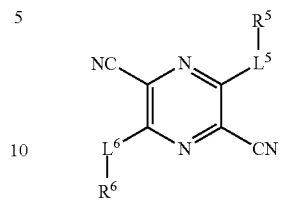

(II)

[In formula (II), $R^5$ represents an electron donating group, $R^6$ represents a hydrogen atom, a substituted or unsubstituted aryl group or an electron donating group, $L^5$ represents a substituted or unsubstituted heteroarylene group or a substituted or unsubstituted arylene group, $L^6$ represents a single bond, a substituted or unsubstituted heteroarylene group or a substituted or unsubstituted arylene group.]

[2] The compound according to [1], wherein $R^3$ and $R^5$ are at least one selected from the group consisting of the groups represented by formulas (d1) to (d7).

[Chemical formula 15]

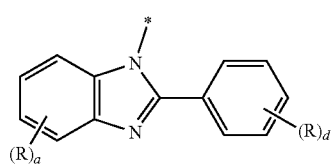

(d1)

[Chemical formula 16]

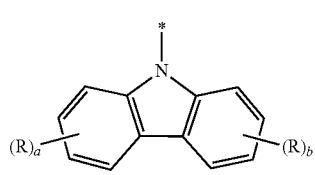

(d2)

[Chemical formula 17]

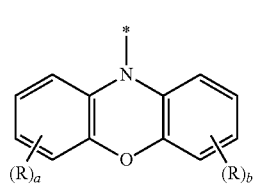

(d3)

[Chemical formula 18]

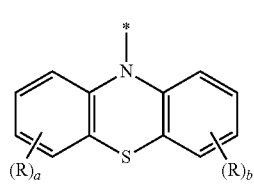

(d4)

-continued

[Chemical formula 19]

(d5)

[Chemical formula 20]

(d6)

[Chemical formula 21]

(d7)

(In formulas (d1) to (d7), R represents a substituent, a and b each independently represent a number of 1 in the parentheses and are an integer of 0 to 4. c represents a number of R in the parentheses and is an integer of 0 to 2. d represents a number of R in the parentheses and is an integer of 0 to 5. When there are a plurality of R, they may be the same substituents or different substituents. Two adjacent Rs may bond together to form a ring with the carbon atoms to which Rs are bonded. * represents a bonding site.)

[3] The compound according to [1] or [2], wherein $R^4$ and are at least one selected from the group consisting of the groups represented by formulas (d1) to (d7).

[4] The compound according to [1], [2] or [3], wherein $L^3$, $L^4$, $L^5$ and $L^6$ are each independently a substituted or unsubstituted arylene group.

[5] A luminescent material comprising the compound defined in any one of [1] to [4].

[6] A luminescence device comprising the luminescent material defined in the above [5].

[7] A method for producing a 2,5-dicyano-3,6-dihalogenopyrazine (formula (11)), including reacting (2E)-2,3-diamino-3-(substituted sulfanyl)-2-propenenitrile in a solvent in the presence of oxygen under acidic conditions to obtain 2,5-dicyano-3,6-diaminopyrazine; and subjecting the 2,5-dicyano-3,6-diaminopyrazine (formula (10)) to a halogenation reaction in a solvent in the presence of nitrous acid or nitrite.

[Chemical formula 22]

(10)

[Chemical formula 23]

(11)

In formula (11), X represents a halogen atom.

[8] The method according to [7], wherein the (2E)-2,3-diamino-3-(substituted sulfanyl)-2-propenenitrile is a compound represented by formula (9).

[Chemical formula 24]

(9)

(In formula (9), R represents a substituted or unsubstituted aryl group, a substituted or unsubstituted alkyl group, a substituted or unsubstituted aralkyl group, or a substituted or unsubstituted alkenyl group.)

[9] A method for producing a 2,5-dicyano-3,6-dihalogenopyrazine including subjecting a 2,5-dicyano-3,6-diaminopyrazine to a halogenation reaction in a solvent in the presence of nitrous acid or nitrite.

[10] The method according to any one of [7] to [9] wherein a temperature during the halogenation reaction is 30 to 60° C.

Effects of the Invention

The dicyanopyrazine compound according to the present invention is useful as a luminescent material. Some of the luminescent materials according to the present invention emits delayed fluorescence. The luminescence device including the luminescent material according to the present invention can provide excellent luminescence efficiency.

Further, according to the production method of the present invention, a 2,5-dicyano-3,6-dihalogenopyrazine can be produced from an inexpensive starting material with less reaction steps and in a high yield.

BEST MODE FOR CARRYING OUT THE INVENTION

Figure 1:
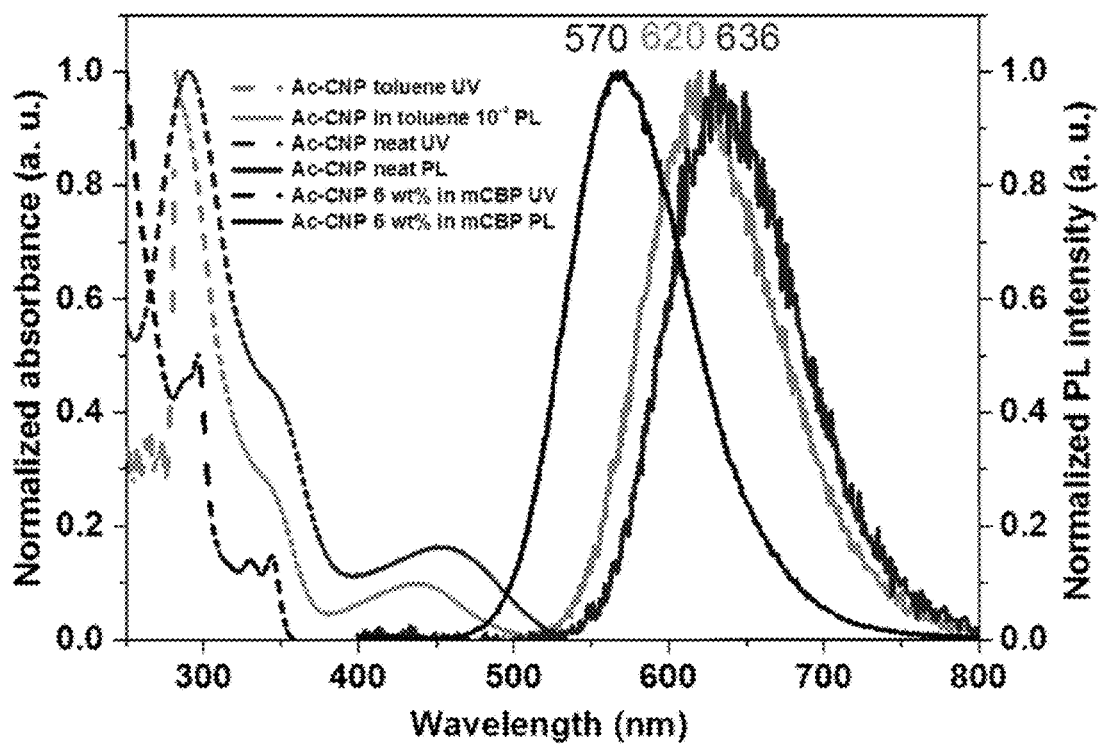
FIG. 1 shows an absorption/emission spectrum of Ac-CNP toluene solution A, Ac-CNP organic photoluminescence device B and Ac-CNP organic photoluminescence device.

The dicyanopyrazine compound of the present invention is a compound represented by formula (I) or formula (II).

[Chemical formula 25]

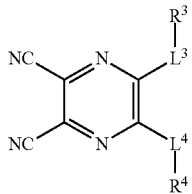

(I)

[in formula (I), $R^3$ represents an electron donating group, $R^4$ represents a hydrogen atom, a substituted or unsubstituted aryl group or an electron donating group, $L^3$ represents a substituted or unsubstituted heteroarylene group or a substituted or unsubstituted arylene group, $L^4$ represents a single bond, a substituted or unsubstituted heteroarylene group or a substituted or unsubstituted arylene group. $L^3$ and $L^4$ may bond together to form a ring with the carbon atoms to which they are bonded.]

[Chemical formula 26]

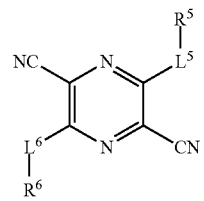

(II)

[in formula (II), $R^5$ represents an electron donating group, $R^6$ represents a hydrogen atom, a substituted or unsubstituted aryl group, or an electron donating group, $L^5$ represents a substituted or unsubstituted heteroarylene group, or a substituted or unsubstituted arylene group, $L^6$ represents a single bond, a substituted or unsubstituted heteroarylene group, or a substituted or unsubstituted arylene group.]

In the present invention, the term "unsubstituted" means that the group is solely formed of a group serving as a mother nucleus. When it is described only by a name of a group serving as a mother nucleus, it means "unsubstituted" unless otherwise stated.

On the other hand, the term "substituted" means that at least one of hydrogen atoms of a mother nucleus are substituted with a group having a structure same as or different from the mother nucleus. Accordingly, the "substituent" is another group bonded to the group serving as a mother nucleus. The number of substituents may be one, or two or more. Two or more substituents may be the same or different.

The "substituent" is not particularly limited as long as it is chemically acceptable and has the effects of the present invention.

Specific examples of the "substituent" include the following groups.

A halogeno group such as a fluoro group, chloro group, bronco group, iodo group or the like;

A C1-6 alkyl group such as a methyl group, ethyl group, n-propyl group, i-propyl group, n-butyl group, s-butyl group, i-butyl group, t-butyl group, n-pentyl group, n-hexyl group or the like;

A C2-6 alkenyl group such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group or the like;

A C2-6 alkynyl group such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2- butynyl group, 2-methyl-3-pentynyl group, 1-hexynyl group, 1,1-dimethyl-2-butynyl group or the like;

A C3-8 cycloalkyl group such as a cyclopropyl group, cyclobutyl group, cyclopentyl group, cyclohexyl group, cycloheptyl group, cubanyl group or the like;

A C3-8 cycloalkenyl group such as a 2-cyclopropenyl group, 2-cyclopentenyl group, 3-cyclohexenyl group, 4-cyclooctenyl group or the like;

A C6-10 aryl group such as a phenyl group, naphthyl group or the like;

A 5-membered heteroaryl group such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group or the like;

A 6-membered heteroaryl group such as a pyridyl group, pyrazinyl group, pyrimidinyl group, pyridazinyl group, triazinyl group or the like;

A fused ring of heteroaryl group such as an indolyl group, benzofuryl group, benzothienyl group, benzimidazolyl group, benzoxazolyl group, benzothiazolyl group, quinolyl group, isoquinolyl group, quinoxalinyl group or the like;

A cyclic ether group such as an oxiranyl group, tetrahydrofuryl group, dioxolanyl group, dioxolanyl group or the like;

A cyclic amino group such as an aziridinyl group, pyrrolidinyl group, piperidyl group, piperazinyl group, morpholinyl group or the like;

A hydroxyl group; An oxo group;

A C1-6 alkoxy group such as a methoxy group, ethoxy group, n-propoxy group, i-propoxy group, n-butoxy group, s-butoxy group, i-butoxy group, t-butoxy group;

A C2-6 alkenyloxy group such as a vinyloxy group, allyloxy group, propenyloxy group, butenyloxy group or the like;

A C2-6 alkynyloxy group such as an ethynyloxy group, propargyloxy group or the like;

A C6-10 aryloxy group such as a phenoxy group, naphthoxy group or the like;

A 5- to 6-membered heteroaryloxy group such as a thiazolyloxy group, pyridyloxy group or the like;

A carboxyl group;

A formyl group; A C1-6 alkylcarbonyl group such as an acetyl group, propionyl group or the like;

A formyloxy group; A C1-6 alkylcarbonyloxy group such as an acetyloxy group, propionyloxy group or the like;

A C1-6 alkoxycarbonyl group such as a methoxycarbonyl group, ethoxycarbonyl group, n-propoxycarbonyl group, i-propoxycarbonyl group, n-butoxycarbonyl group, t-butoxycarbonyl group or the like;

A C1-6 haloalkyl group such as a chloromethyl group, chloroethyl group, trifluoromethyl group, 1,2-dichloro-n-propyl group, 1-fluoro-n-butyl group, perfluoro-n-pentyl group or the like;

A C2-6 haloalkenyl group such as 2-chloro-1-propenyl group, 2-fluoro-1-butenyl group or the like;

A C2-6 haloalkynyl group such as a 4,4-dichloro-1-butynyl group, 4-fluoro-1-pentynyl group, 5-bromo-2-pentynyl group or the like;

A C3-6 halocycloalkyl group such as a 3,3-difluorocyclobutyl group or the like;

A C1-6 haloalkoxy group such as a 2-chloro-n-propoxy group, 2,3-dichlorobutoxy group, trifluoromethoxy group, 2,2,2-trifluoroethoxy group or the like;

A C2-6 haloalkenyloxy group such as a 2-chloropropenyloxy group, 3-bromobutenyloxy group or the like;

A C1-6 haloalkylcarbonyl group such as a chloroacetyl group, trifluoroacetyl group, trichloroacetyl group or the like;

A cyano group; A nitro group; an amino group;

A C1-6 alkylamino group such as a methylamino group, dimethylamino group, diethylamine group or the like;

A C6-10 arylamino group such as an aniline group, naphthylamino group or the like;

A formylamino group; A C1-6 alkylcarbonylamino group such as an acetylamine group, propanoylamino group, butyrylamino group, i-propylcarbonylamino group or the like;

A C1-6 alkoxycarbonylamino group such as a methoxycarbonylamino group, ethoxycarbonylamino group, n-propoxycarbonylamino group, i-propoxycarbonylamino group or the like;

A C1-6 alkylsulfoxyimino group such as an S,S-dimethylsulfoxyimino group or the like;

An aminocarbonyl group;

A C1-6 alkylaminocarbonyl group such as a methylaminocarbonyl group, dimethylaminocarbonyl group, ethylaminocarbonyl group, i-propylaminocarbonyl group or the like;

An imino C1-6 alkyl group such as an iminomethyl group, (1-imino) ethyl group, (1-imino)-n-propyl group or the like;

A hydroxyimino C1-6 alkyl group such as a hydroxyiminomethyl group, (1-hydroxyimino) ethyl group, (1-hydroxyimino) propyl group or the like;

A C1-6 alkoxyimino C1-6 alkyl group such as a methoxyiminomethyl group, (1-methoxyimino) ethyl group or the like;

A mercapto group;

A C1-6 alkylthio group such as a methylthio group, ethylthio group, n-propylthio group, i-propylthio group, n-butylthio group, i-butylthio group, s-butylthio group, t-butylthio group or the like;

A C1-6 haloalkylthio group such as a trifluoromethylthio group. 2,2,2-trifluoroethylthio group or the like;

A C2-6 alkenylthio group such as a vinylthio group, allylthio group or the like;

A C2-6 alkynylthio group such as an ethynylthio group, propargylthio group or the like;

A C1-6 alkylsulfinyl group such as a methylsulfinyl group, ethylsulfinyl group, t-butylsulfinyl group or the like;

A C1-6 haloalkylsulfinyl group such as a trifluoromethylsulfinyl group, 2,2,2-trifluoroethylsulfinyl group or the like;

A C2-6 alkenylsulfinyl group such as an allylsulfinyl group or the like;

A C2-6 alkynylsulfinyl group such as a propargylsulfinyl group or the like;

A C1-6 alkylsulfonyl group such as a methylsulfonyl group, ethylsulfonyl group, t-butylsulfonyl group or the like;

A C1-6 haloalkylsulfonyl group such as a trifluoromethylsulfonyl group, 2,2,2-trifluoroethylsulfonyl group or the like;

A C2-6 alkenylsulfonyl group such as an allylsulfonyl group or the like;

A C2-6 alkynylsulfonyl group such as a propargylsulfonyl group or the like;

A tri C1-6 alkylsilyl group such as a trimethylsilyl group, triethylsilyl group, t-butyldimethylsilyl group or the like;

A tri C6-10 arylsilyl group such as a triphenylsilyl group or the like;

In addition, any hydrogen atom in the "substituent" may be substituted with a group having a structure different from the "substituent".

The term "C1-6" or the like means that the number of carbon atoms in the group serving as a mother nucleus is 1 to 6. The number of carbon atoms does not include the number of carbon atoms present in the substituents. For example, an ethoxybutyl group is classified as a C2 alkoxy C4 alkyl group because the group serving as a mother nucleus is butyl group and the substituent is ethoxy group.

The electron donating group for $R^3$, $R^4$, $R^5$ or $R^6$ in formula (I) or formula (II) is an atom or atomic group having a property of donating an electron to the pyrazine ring. The Hammett's $\sigma_p$ value of the electron donating group is preferably less than 0. The Hammett's $\sigma_p$ value quantified the influence of the substituent on the reaction rate or equilibrium of the para-substituted benzene derivative. Specifically, the Hammett's $\sigma_p$ value is a value defined by one of formulas (h1) and (h2).

$$\text{Log}(k/k0)=\rho\cdot\sigma_p \quad (h1)$$

$$\text{Log}(K/K0)=\rho\cdot\sigma_p \quad (h2)$$

k is a reaction rate constant of an unsubstituted benzene derivative, $k_0$ is a reaction rate constant of a substituted benzene derivative, K is an equilibrium constant of an unsubstituted benzene derivative, $K_0$ is an equilibrium constant of a substituted benzene derivative, $\rho$ is a reaction constant determined by reaction types and conditions. For a detailed explanation of Hammett's $\sigma_p$ value and the value of each substituent, J. A. Dean ed., "Lange's Handbook of Chemistry 13th Edition", 1985, 3-132 to 3-137, McGrow-Hill can be referred.

Examples of the electron donating group for $R^3$, $R^4$, $R^5$ or $R^6$ include those groups containing a hetero atom and having a Hammett's $\sigma_p$ value of less than 0. Examples of the hetero atom include a nitrogen atom, an oxygen atom, a sulfur atom, a silicon atom, a phosphorus atom and the like. A preferred electron donating group is a group having a bond at the hetero atom or a group having a structure in which at least one of the hetero atoms is bonded to an $sp^2$ carbon atom so that a $\pi$ conjugation including the $sp^2$ carbon atom extends to the pyrazine ring.

Examples of the group having a bond at the hetero atom include a substituted or unsubstituted diarylamino group, a substituted or unsubstituted dialkylamino group, a substituted or unsubstituted alkylarylamino group, a substituted or unsubstituted cyclic amino group, a substituted or unsubstituted aryl oxy group, a substituted or unsubstituted alkyloxy group, a substituted or unsubstituted arylthio group, a substituted or unsubstituted alkylthio group, a substituted or unsubstituted triarylsilyl group, a substituted or unsubstituted alkyldiarylsilyl group, a substituted or unsubstituted dialkylarylsilyl group, a substituted or unsubstituted trialkylsilyl group, a substituted or unsubstituted cyclic silyl group, a substituted or unsubstituted diarylphosphino group, a substituted or unsubstituted dialkylphosphino group, a substituted or unsubstituted cyclic phosphino group, and the like.

The group having a structure in which at least one of the hetero atoms is bonded to an $sp^2$ carbon atom so that a $\pi$ conjugation including the $sp^2$ carbon atom extends to the pyrazine ring includes an aryl group substituted with a group having a bond at the hetero atom, a heteroaryl group substituted by a group having a bond at the heteroatom, an aryl group substituted by a group having a structure in which a hetero atom is bonded to an $sp^2$ carbon atom and having a structure in which a $\pi$ conjugation including the $sp^2$ carbon atom extends to the pyrazine ring via the aryl group, a heteroaryl group substituted by a group having a structure in which a heteroatom is bonded to an $sp^2$ carbon atom and having a structure in which a $\pi$ conjugation including the $sp^2$ carbon atom extends to the pyrazine ring via the heteroaryl group, an alkenyl group substituted by a group having a structure in which a hetero atom is bonded to an $sp^2$ carbon atom and having a structure in which a $\pi$ conjugation including the $sp^2$ carbon atom extends to the pyrazine ring via the alkenyl group, an alkynyl group substituted by a group having a structure in which a hetero atom is bonded to an $sp^2$ carbon atom and having a structure in which a $\pi$ conjugation including the $sp^2$ carbon atom extends to the pyrazine ring via the alkynyl group, and the like.

Preferable examples of the electron donating group for $R^3$, $R^4$, $R^5$ or $R^6$ include a group having a bond at a hetero atom, an aryl group substituted by a group having a bond at a hetero atom, a heteroaryl group substituted by a group having a bond at a hetero atom, an aryl group substituted by a group having a structure in which a hetero atom is bonded to an $sp^2$ carbon atom and having a structure in which a $\pi$ conjugation including the $sp^2$ carbon atom extends to the pyrazine ring via the aryl group, a heteroaryl group substituted by a group having a structure in which a heteroatom is bonded to an $sp^2$ carbon atom and having a structure in which an conjugation including the $sp^2$ carbon atom extends to the pyrazine ring via the heteroaryl group and more preferable examples include a group having a bond at a hetero atom, an aryl group substituted by a group having a bond at a hetero atom, and an aryl group substituted by a group having a structure in which a heteroatom is bonded to an $sp^2$ carbon atom and having a structure in which a $\pi$ conjugation including the $sp^2$ carbon atom extends to the pyrazine ring via the aryl group.

The aryl group which is a constituent of the electron donating group may be either monocyclic or polycyclic. In the polycyclic aryl group, as long as at least one ring is an aromatic ring, the remaining rings may be a saturated ring, an unsaturated ring or an aromatic ring. The number of carbon atoms constituting the unsubstituted aryl group is preferably from 6 to 40, more preferably from 6 to 20, even more preferably from 6 to 14.

Examples of the unsubstituted aryl group include a phenyl group, 1-naphthyl group, 2-naphthyl group, azulenyl group, indanyl group, tetralinyl group and the like.

Examples of the substituted aryl group include a 4-fluorophenyl group, 4-chlorophenyl group, 2,4-dichlorophenyl group, 3,4-dichlorophenyl group, 3,5-dichlorophenyl group, 2,6-difluorophenyl group, 4-trifluoromethylphenyl group, 4-methoxyphenyl group, 3,4-dimethoxyphenyl group, 3,4-methylenedioxyphenyl group, 4-trifluoromethoxyphenyl group, 4-methoxy-1-naphthyl group and the like.

The heteroaryl group which is a constituent of the electron donating group may be either monocyclic or polycyclic. In the polycyclic heteroaryl group, as long as at least one ring is a heteroaromatic ring, the remaining rings may be a saturated ring, an unsaturated ring or an aromatic ring. The number of atoms constituting the unsubstituted heteroaryl group is preferably from 5 to 40, more preferably from 5 to 20, even more preferably from 5 to 14.

Examples of the unsubstituted heteroaryl group include a 5-membered heteroaryl group such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, tetrazolyl group or the like; a 6-membered heteroaryl group such as a pyridyl group, pyrazinyl group, pyrimidinyl group, pyridazinyl group, triazinyl group or the like; a fused ring heteroaryl group such as an indolyl group, benzofuryl group, benzothienyl group, benzimidazolyl group, benzoxazolyl group, benzothiazolyl group, quinolyl group, isoquinolyl group, quinoxalinyl group or the like; and the like.

The alkenyl group which is a constituent of the electron donating group has at least one carbon-carbon double bond in the molecule. Examples of the alkenyl group include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, i-methyl-2-butenyl group, 2-methyl-2-butenyl group, 1-hexenyl group, 2-hexenyl group, 3-hexenyl group, 4-hexenyl group, 5-hexenyl group and the like.

The alkynyl group which is a constituent of the electron donating group has at least one carbon-carbon triple bond in the molecule. Examples of the alkynyl group include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butyryl group and the like.

The electron donating group for $R^3$, $R^4$, $R^5$ or $R^6$ is preferably at least one selected from the group consisting of the groups represented by formulas (d1) to (d7), and more preferably at least one selected from the group consisting of the groups represented by formulas (d2), (d3) and (d6).

[Chemical formula 27]

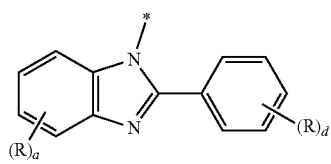
(d1)

[Chemical formula 28]

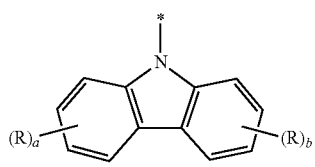
(d2)

[Chemical formula 29]

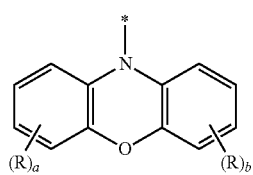
(d3)

[Chemical formula 30]

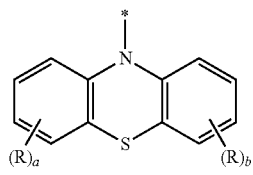
(d4)

[Chemical formula 31]

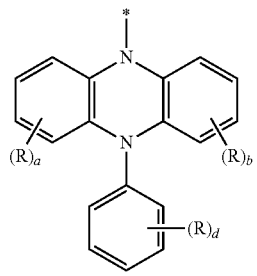
(d5)

[Chemical formula 32]

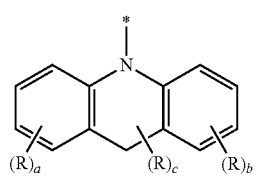
(d6)

[Chemical formula 33]

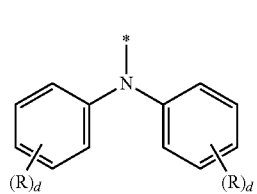
(d7)

(In formulas (d1) to (d7), R represents a substituent, a and b each independently represent a number of R in the parenthesis and are an integer of 0 to 4, preferably 0 or 1, and more preferably 0. c represents a number of R in the parentheses and is an integer from 0 to 2, and preferably 0. d represents a number of R in the parentheses and is an integer of 0 to 5, and preferably 0. When there is a plurality of R, they may be the same substituents or different substituents. Two adjacent Rs may bond together to form a ring with the carbon atoms to which Rs are bonded. * represents a bonding site.)

Preferable examples of R include a hydroxy group, halogeno group, C1-20 alkyl group, C1-20 alkoxy group, C1-20 alkylthio group, C1-20 alkyl substituted amino group, C6-40 aryl-substituted amino group, C6-40 aryl group, 5- to 40-membered heteroaryl group, C2-10 alkenyl group, C2-10 alkynyl group, C2-20 alkylamido group, C6-20 arylamide group and tri C1-10 alkylsilyl group; and more preferable examples include a C1-20 alkyl group, C1-20 alkoxy group, C1-20 alkylthio group, C1-20 alkyl-substituted amino group, C6-40 aryl-substituted amino group, C6-40 aryl group and 5- to 40-membered heteroaryl group; and even more preferable examples include a C6-40 aryl group.

Examples of the ring formed by bonding two adjacent Rs include a benzene ring, naphthalene ring, pyridine ring, pyridazine ring, pyrimidine ring, pyrazine ring, pyrrole ring, imidazole ring, pyrazole ring, imidazoline ring, oxazole ring, isoxazole ring, thiazole ring, isothiazole ring, cyclohexadiene ring, cyclohexene ring, cyclopentene ring, cycloheptatriene ring, cycloheptadiene ring, cycloheptene ring and the like.

The substituted or unsubstituted aryl group for $R^4$ or $R^6$ may be either monocyclic or polycyclic. In the polycyclic aryl group, as long as at least one ring is an aromatic ring, the remaining rings may be a saturated ring, an unsaturated ring or an aromatic ring. The number of carbon atoms constituting the unsubstituted aryl group is preferably from 6 to 40, more preferably from 6 to 20, and even more preferably from 6 to 14.

Examples of the unsubstituted aryl group include a phenyl group, 1-naphthyl group, 2-naphthyl group, azulenyl group, indanyl group, tetralinyl group and the like.

Examples of the substituted aryl group include a 4-fluorophenyl group, 4-chlorophenyl group, 2,4-dichlorophenyl group, 3,4-dichlorophenyl group, 3,5-dichlorophenyl group, 2,6-difluorophenyl group, 4-trifluoromethylphenyl group, 4-methoxyphenyl group, 3,4-dimethoxyphenyl group, 3,4-methylenedioxyphenyl group, 4-trifluoromethoxyphenyl group, 4-methoxy-1-naphthyl group and the like.

The substituted or unsubstituted arylene group for $L^3$, $L^4$, $L^5$ or $L^6$ may be monocyclic or polycyclic. In the polycyclic arylene group, as long as at least one ring is an aromatic ring, the remaining rings may be a saturated ring, an unsaturated ring or an aromatic ring. The number of carbon atoms constituting the unsubstituted arylene group is preferably from 6 to 40, more preferably from 6 to 20, and even more preferably from 6 to 14.

Examples of the arylene group include a phenylene group, naphthylene group, azulenylene group, indanylene group, tetralinylene group and the like, and among these examples, a phenylene group is particularly preferable.

The substituted or unsubstituted heteroarylene group for $L^3$, $L^4$, $L^5$ or $L^6$ may be monocyclic or polycyclic. In the polycyclic heteroarylene group, as long as at least one ring is a heteroaromatic ring, the remaining rings may be a saturated ring, an unsaturated ring or an aromatic ring. The number of atoms constituting the unsubstituted heteroarylene group is preferably from 5 to 40, more preferably from 5 to 20, and even more preferably from 5 to 14.

Examples of the heteroarylene group include a 5-membered heteroarylene group such as a pyrrolylene group, furylene group, thienylene group, imidazolylene group, pyrazolylene group, oxazolylene group, isoxazolylene group, thiazolylene group, isothiazolylene group, triazolylene group, oxadiazolylene group, thiadiazolylene group, tetrazolylene group or the like; a 6-membered heteroarylene group such as a pyridylene group, pyrazinylene group, pyrimidinylene group, pyridazinylene group, triazinylene group or the like; a fused ring heteroarylene group such as an indolylene group, benzofurylene group, benzothienylene group, benzimidazolylene group, benzoxazolylene group, benzothiazolylene group, quinolylene group, isoquinolylene group, quinoxalinylene group or the like; and the like.

Examples of the ring formed by bonding $L^3$ and $L^4$ include a benzene ring, naphthalene ring, pyridine ring, pyridazine ring, pyrimidine ring, pyrazine ring, pyrrole ring, imidazole ring, pyrazole ring, imidazoline ring, oxazole ring, isoxazole ring, thiazole ring, isothiazole ring, cyclohexadiene ring, cyclohexene ring, cyclopentene ring, cycloheptatriene ring, cycloheptadiene ring, cycloheptene ring and the like.

Specific examples of the dicyanopyrazine compound of the present invention include the following compounds. However, these compounds are merely examples, and the present invention is not limited to these exemplified compounds (I-1) to (I-13) and (II-1) to (II-9).

[Chemical formula 34]

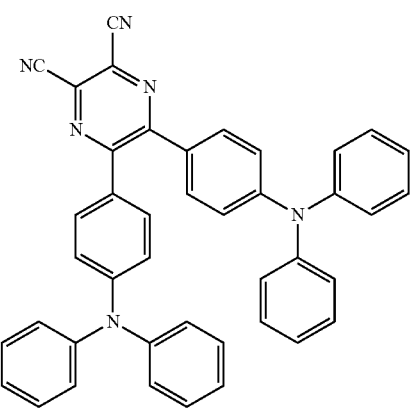

(I-1)

[Chemical formula 35]

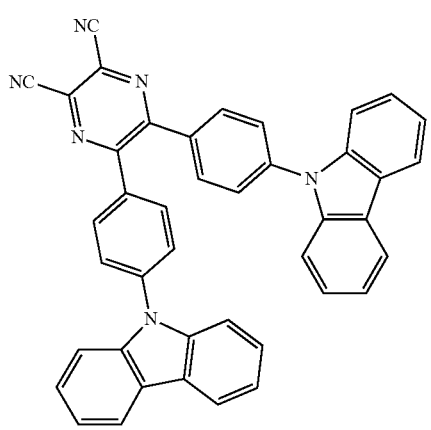

(I-2)

[Chemical formula 36]

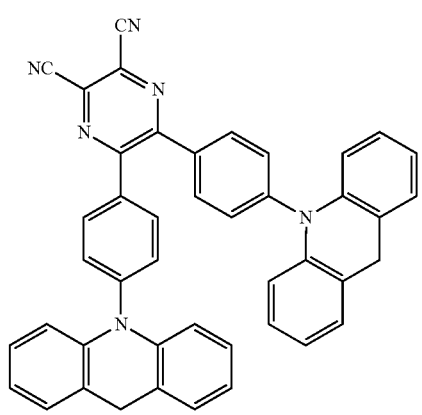

(I-3)

-continued
[Chemical formula 37]
(I-4)
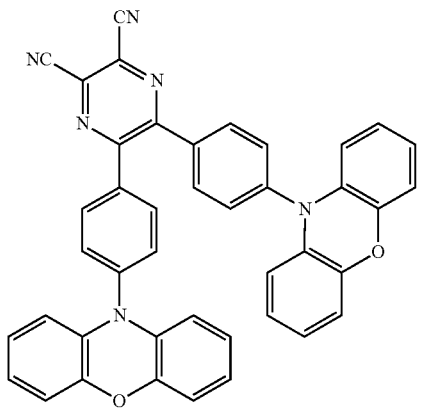
[Chemical formula 38]
(I-5)
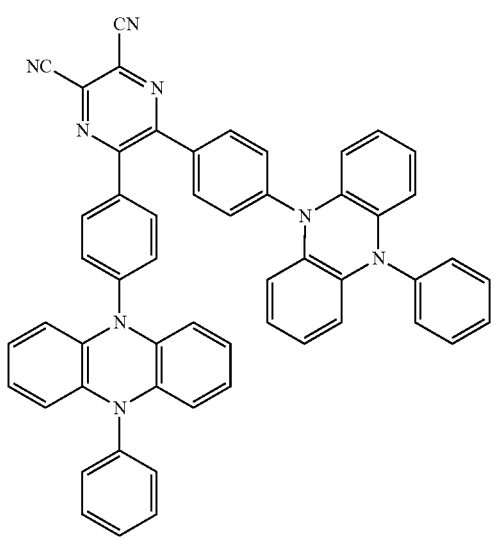
[Chemical formula 39]
(I-6)
[Chemical formula 40]
(I-7)
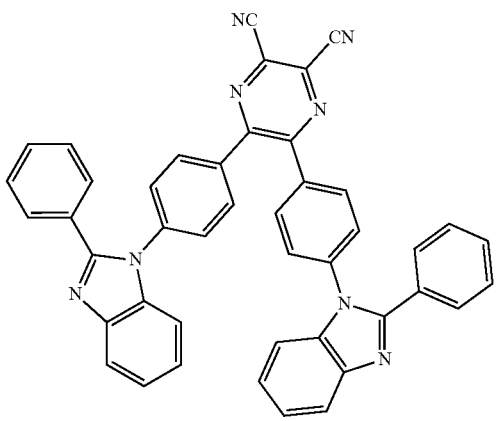
[Chemical formula 41]
(I-8)
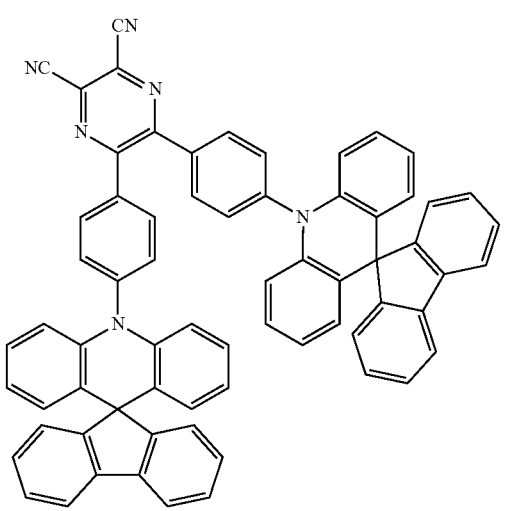
[Chemical formula 42]
(I-9)
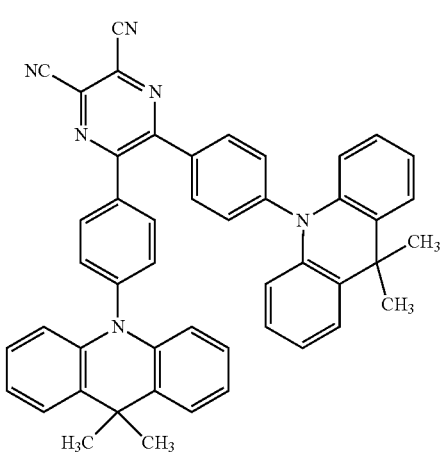

[Chemical formula 43]
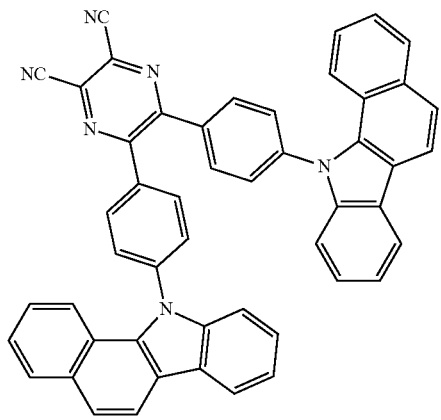
(I-10)
[Chemical formula 44]
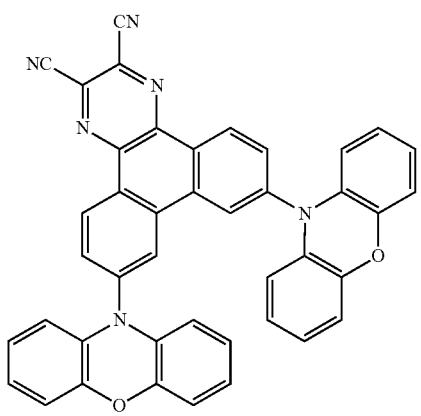
(I-11)
[Chemical formula 45]
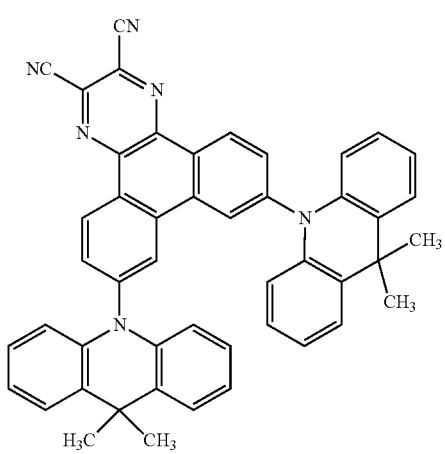
(I-12)
[Chemical formula 46]
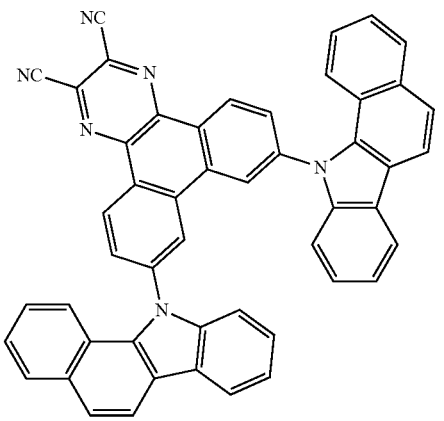
(I-13)
[Chemical formula 47]
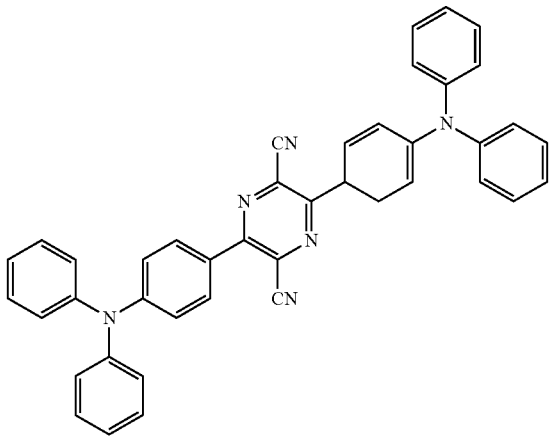
(II-1)
[Chemical formula 48]
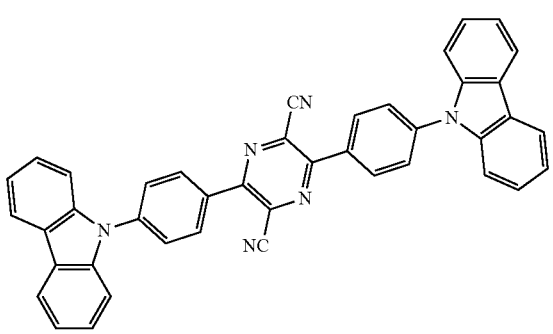
(II-2)

[Chemical formula 49]
(II-3)
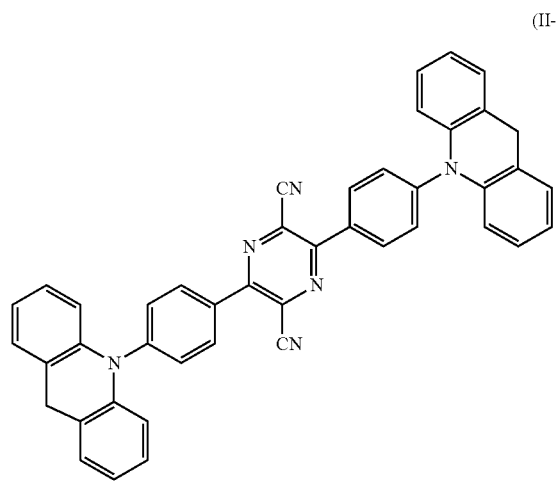
[Chemical formula 50]
(II-4)
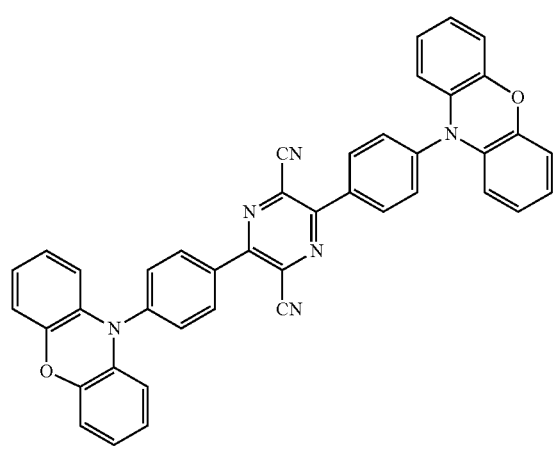
[Chemical formula 51]
(II-5)
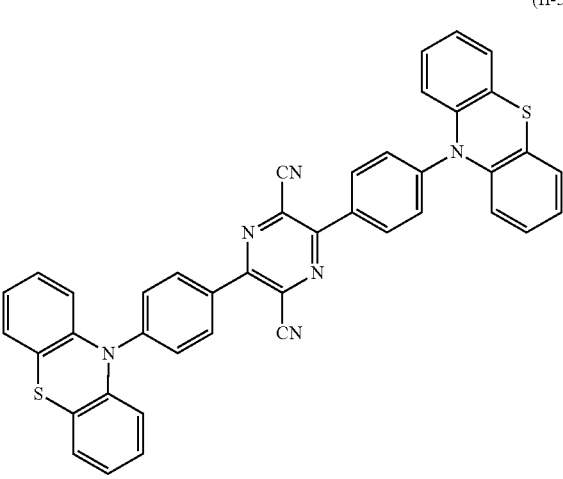
[Chemical formula 52]
(II-6)
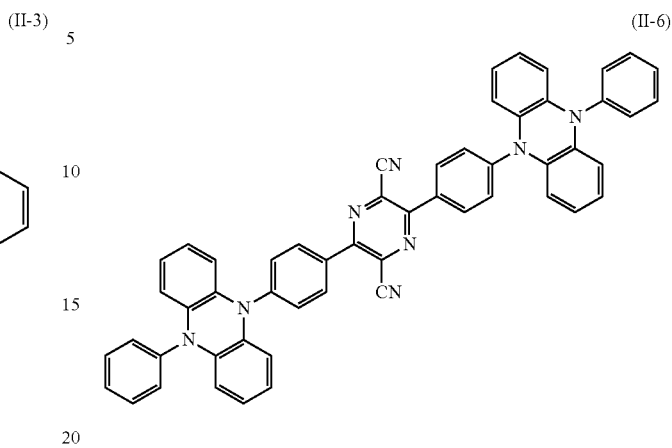
[Chemical formula 53]
(II-7)
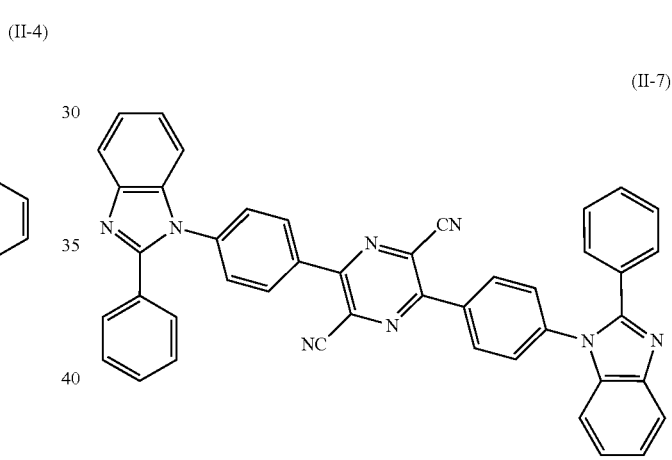
[Chemical formula 54]
(II-8)
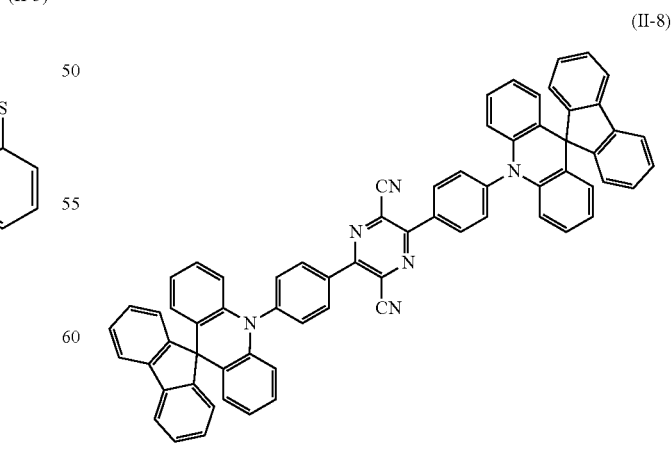

[Chemical formula 55]

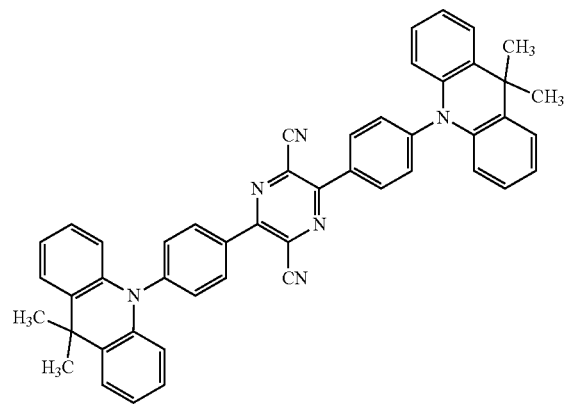

(II-9)

The dicyanopyrazine compound of the present invention can be obtained by performing known synthetic reactions (for example, coupling reaction, substitution reaction, etc.) in combination.

For example, the compound represented by formula (I) can be obtained by reacting a diacetyl compound with a diaminomaleonitrile as shown in the following formula.

EXAMPLE I-1

[Chemical formula 56]

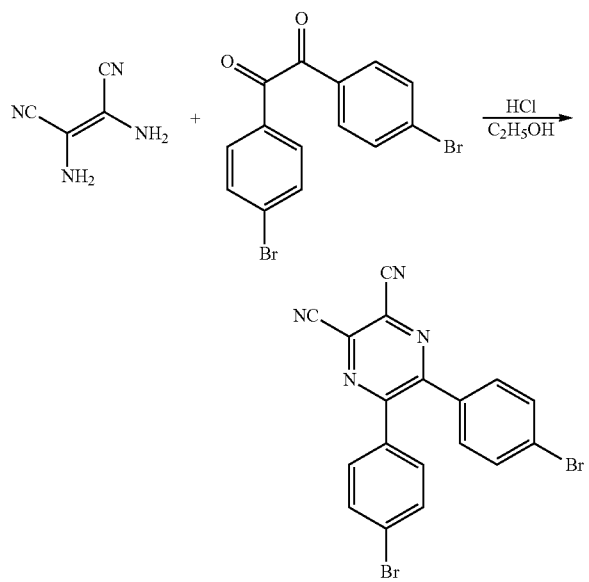

Diamino maleonitrile (0.88 g, 8.2 mmol), 1,2-bis (4-bromophenyl) ethane-1,2-dione (3.0 g, 8.2 mmol) and hydrochloric acid (36%, 1.5 g) were reacted in 60 ml of ethanol at 60° C. for 3 hours in a nitrogen atmosphere. After cooling to room temperature, the reaction product was extracted with 100 ml of dichloromethane and 100 ml of water. The separated organic phase was dried over anhydrous magnesium sulfate and then filtered and evaporated to obtain 5,6-bis (4-bromophenyl) pyrazine-2,3-dicarbonitrile (3.2 g, yield of 90%), which is a mauve solid.

$^1$H NMR (500 MHz, CDCl$_3$, δ): 7.58 (dd, 4H), 7.46 (dd, 4H); MS (MALDI-TOF) m/z: [M]$^+$ calcd for C$_{18}$H$_8$Br$_2$N$_4$, 437.91; found, 437.70.

A substituent such as an electron donating group or the like can be introduced by a substitution reaction of a halogeno group on a benzene ring, or the like.

EXAMPLE I-2

[Chemical formula 57]

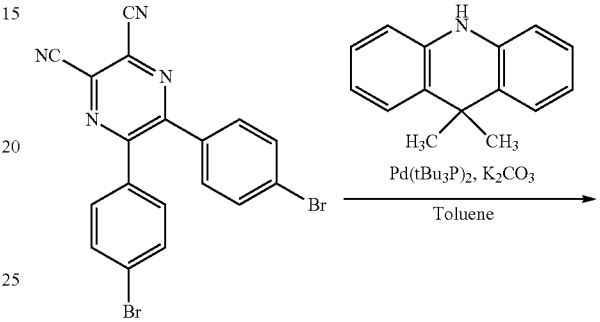

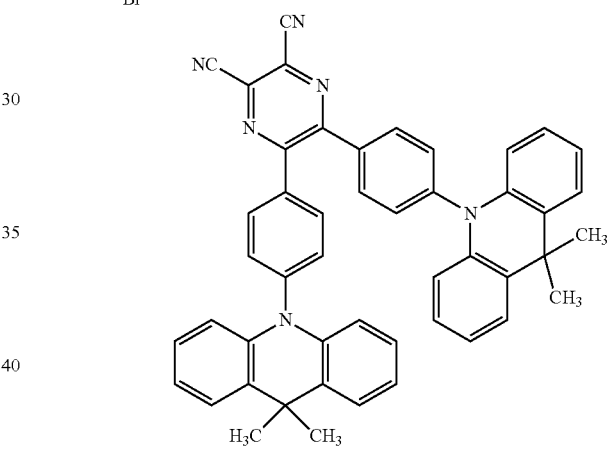

5,6-bis (4-bromophenyl) pyrazine-2,3-dicarbonitrile (1.0 g, 2.3 mmol), 9,9-dimethyl-9,10-dihydroacridine (1.05 g, 5.1 mmol), bis (tri-t-butylphosphine) palladium (0) (0.012 g, 0.023 mmol) and potassium carbonate (0.95 g, 6.9 mmol) were stirred in 30 ml of toluene, while refluxing under a nitrogen atmosphere for 72 hours. The resulting mixture was cooled to room temperature, filtered through celite, and the solvent was removed under reduced pressure. Purification by silica gel column chromatography was performed to obtain 5,6-bis (4-(9,9-dimethyl-9,10-dihydroacridin-10-yl)-phenyl) pyrazine-2,3-dicarbonitrile (0.60 g, 40%), which is an orange solid.

$^1$H NMR (500 MHz, CDCl$_3$, δ): 7.87 (dt, J=8.5 Hz, 2 Hz, 4H), 7.47-7.43 (m, 8H), 6.97-6.90 (m, 8H), 6.35 (dd, J=7.6 Hz, 1.3 Hz, 4H), 1.66 (s, 12H); $^{13}$C NMR (125 MHz, CDCl$_3$, δ): 154.77, 144.69, 140.35, 134.21, 132.3, 131.42, 130.84, 130.16, 126.48, 125.28, 121.48, 114.64, 113.04, 36.18, 30.66; MS (MALDI-TOF) m/z: [M]$^+$ calcd for C$_{48}$H$_{36}$N$_6$, 696.30; found, 696.49. Anal. calcd for C$_{48}$H$_{36}$N$_6$: C, 82.73; H, 5.21; N, 12.06; found: C, 82.21; H, 5.16; N, 11.85.

EXAMPLE I-3

[Chemical formula 58]

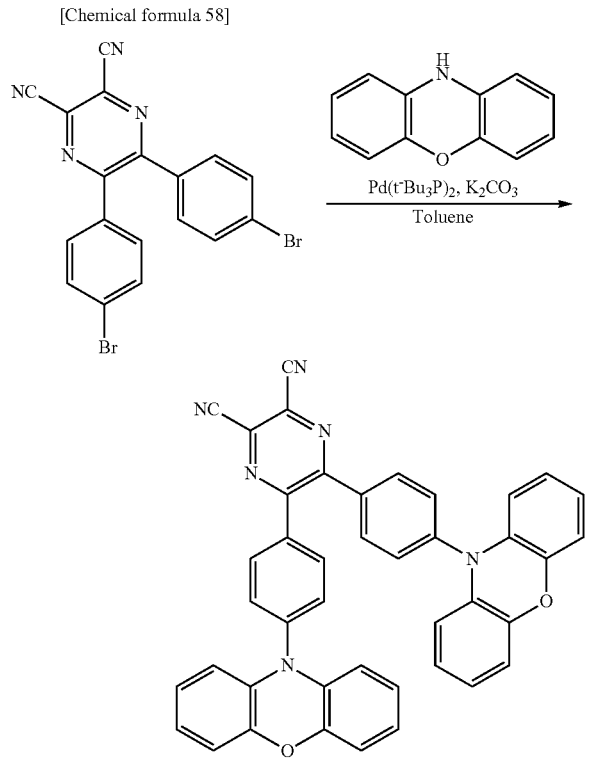

5,6-bis (4-bromophenyl) pyrazine-2,3-dicarbonitrile (1.0 g, 2.3 mmol), 10H-phenoxazine (0.92 g, 5.1 mmol), bis (tri-t-butylphosphine) palladium (0) (0.012 g, 0.023 mmol) and potassium carbonate (0.95 g, 6.9 mmol) were stirred in 30 mol of toluene, while refluxing under a nitrogen atmosphere for 72 hours. Purification by silica gel column chromatography was performed to obtain 5,6-bis (4-(10H-phenoxazin-10-yl)-phenyl) pyrazine-2,3-dicarbonitrile (1.03 g, 70%), which is a red solid.

$^1$H NMR (500 MHz, CDCl$_3$, δ): 7.82 (dt, J=8.5 Hz, 2 Hz, 4H), 7.45 (d, J=8.5 Hz, 4H), 6.75-7.71 (m, 4H), 6.70 (td, J=7.5 Hz, 1 Hz, 4H), 6.59 (td, J=8.0 Hz, 1.5 Hz, 4H), 5.97 (dd, J=8.0 Hz, 1 Hz, 4H); $^{13}$C NMR (125 MHz, CDCl$_3$, δ): 154.52, 144.15, 140.34, 134.21, 133.43, 132.48, 131.33, 123.38, 122.15, 115.91, 113.24, 122.85; MS (MALDI-TOF) m/z: [M]$^+$ calcd for C$_{42}$H$_{24}$N$_6$O$_2$, 644.21; found, 644.43. Anal. calcd for C$_{42}$H$_{24}$N$_6$O$_2$: C, 78.25; H, 3.75; N, 13.04; O, 4.96; found: C, 78.33; H, 3.65; N, 13.13.

EXAMPLE I-4

[Chemical formula 59]

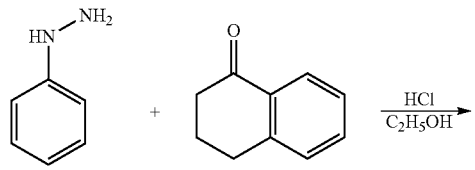

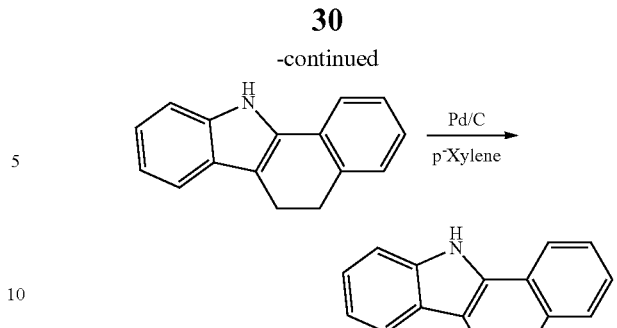

Phenylhydrazine (10.0 g, 92.5 mmol), α-tetralone (13.5 g, 92.5 mmol) and ethanol (100 mL) were stirred at room temperature under a nitrogen atmosphere and then hydrochloric acid (35%, 15 mL) was added thereto. The resulting mixture was stirred at 60° C. under a nitrogen atmosphere for 3 hours. Then, the resulting mixture was cooled to room temperature, and solids were filtered. 6,11-dihydro-5H-benzo [a] carbazole (18.2 g, 90%), which is a white solid was obtained.

$^1$H NMR (500 MHz, CDCl3): 8.20 (br s, 1H), 7.56 (d, J=8.0 Hz, 1H), 7.39 (d, J=8.0 Hz, 1H), 7.34 (d, J=7.5 Hz, 1H), 7.28-7.25 (m, 2H), 7.20-7.15 (m, 2H), 7.14 (td, J=8.0 Hz, 1.0 Hz, 1H), 3.09-2.97 (m, 4H). MS (MALDI-TOF): m/z 219.32 [M]$^-$; calcd 219.10.

6,11-dihydro-5H-benzo [a] carbazole (10.0 g, 45.6 mmol) and p-xylene (100 mL) were stirred at room temperature under a nitrogen atmosphere. Palladium (10 wt %, 0.49 g, 4.56 mmol) carried on carbon was slowly added thereto. The resulting mixture was refluxed for 24 hours under a nitrogen atmosphere. The resulting product was cooled to room temperature, filtered through celite, and the solvent was removed under reduced pressure. The resulting product was then washed with methanol to obtain 11H-benzo [a] carbazole (8.92 g, 90%), which is a white solid.

$^1$H NMR (500 MHz, CDCl$_3$): 8.81 (br s, 1H), 8.16 (t, J=8.5 Hz, 3H), 8.03 (d, J=8.0 Hz, 1H), 7.68 (d, J=8.0 Hz, 1H), 7.63 (td, J=6.7 Hz, 1.25 Hz, 1H), 7.56 (td, J=8.0 Hz, 1.25 Hz, 1H), 7.46 (td, J=7.2 Hz, 1.25 Hz, 1.1H), 7.33 (td, J=8.0 Hz, 1.25 Hz, 0.8H). MS (MALDI-TOF): m/z 217.57 [M]$^+$; calcd 217.09.

[Chemical formula 60]

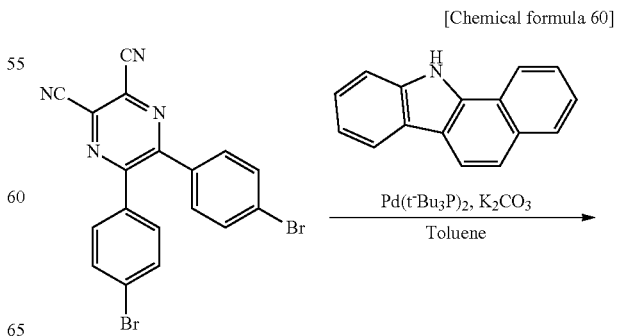

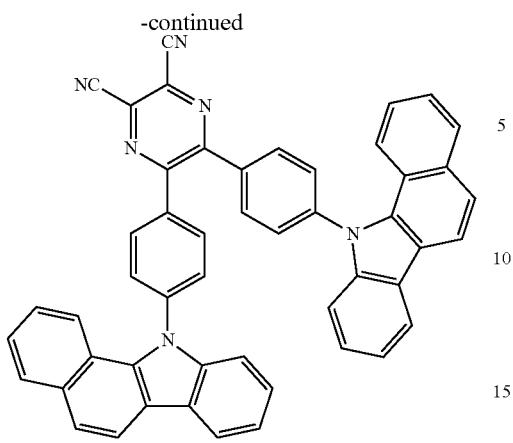

5,6-bis (4-bromophenyl) pyrazine-2,3-dicarbonitrile (1.0 g, 2.3 mmol), 11H-benzo [a] carbazole (1.11 g, 5.1 mmol), bis (tri-t-butylphosphine) palladium (0) (0.012 g, 0.023 mmol) and potassium carbonate (0.95 g, 6.9 mmol) were stirred in 30 ml of toluene, while refluxing for 72 hours under a nitrogen atmosphere. The resulting mixture was cooled to room temperature, filtered through celite, and the solvent was removed under reduced pressure. Purification by silica gel-column chromatography was performed to obtain 5,6-bis (4-(11H-benzo [a] carbazol-11-yl)-phenyl) pyrazine-2,3-dicarbonitrile (0.50 g, 31%), which is an orange solid.

Anal. calcd for $C_{48}H_{36}N_6$: C, 84.25; H, 3.96; N, 11.79; found: C, 84.21; H, 3.96; N, 11.07.

EXAMPLES I-5

The compound represented by formula (I) can be obtained by reacting a diamino maleonitrile with a phenanthrene-9,10-dione compound as shown in the following formula.

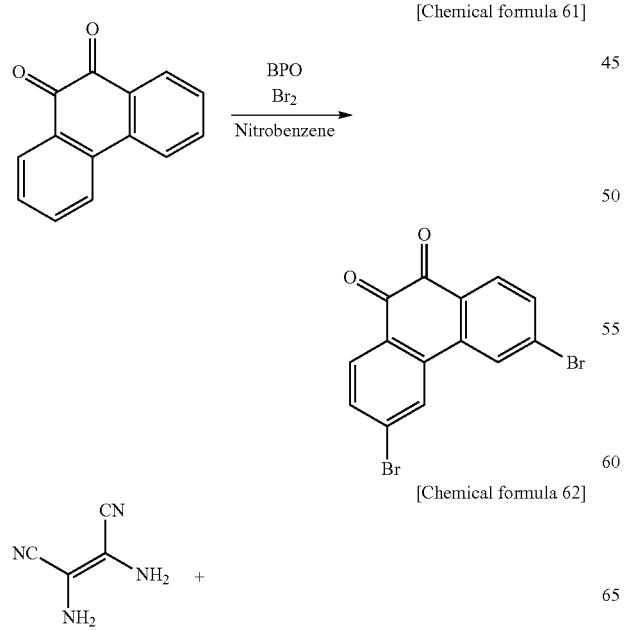

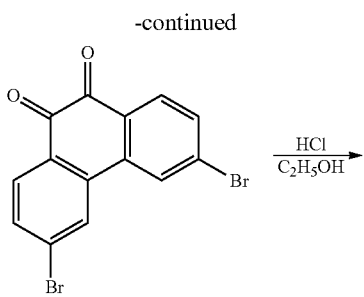

A substituent such as an electron donating group or the like can be introduced by a substitution reaction of a halogeno group on a benzene ring or the like.

EXAMPLE I-6

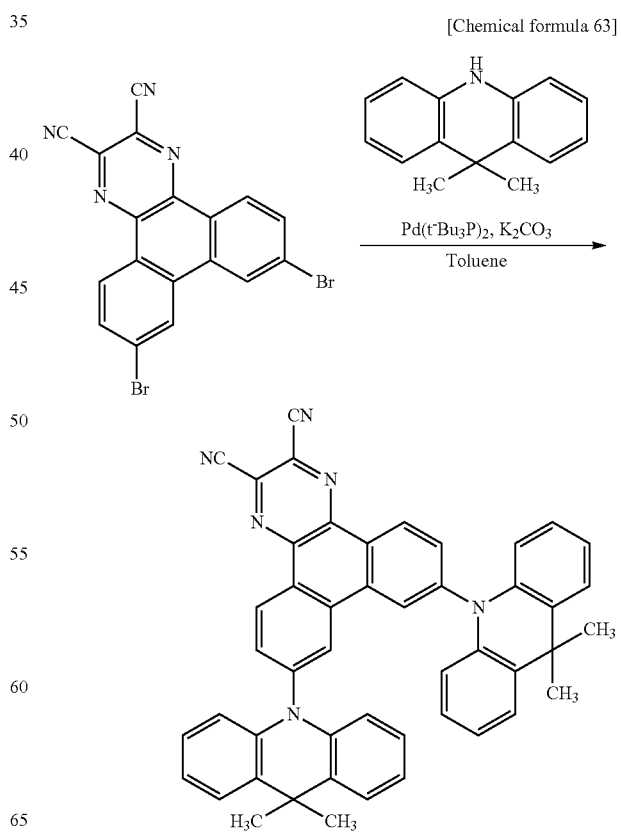

EXAMPLE I-7
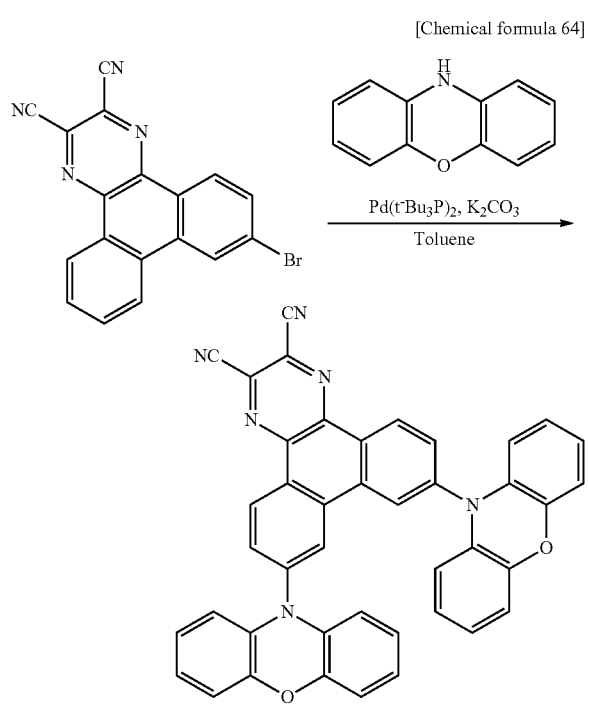
EXAMPLE I-8
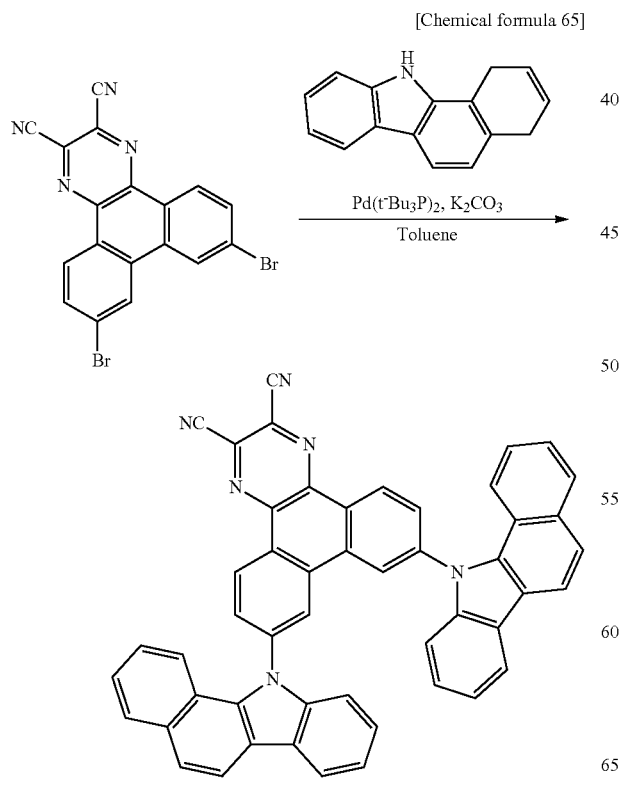
EXAMPLE II-1
The compound represented by formula (II) can be obtained by reacting 2,5-dicyano-3,6-dibromopyrazine with a compound having an electron donating group as shown in the following formula. 2,5-dicyano-3,6-dibromopyrazine can be obtained by, for example, the method described in Non-Patent Document 1 and the like.
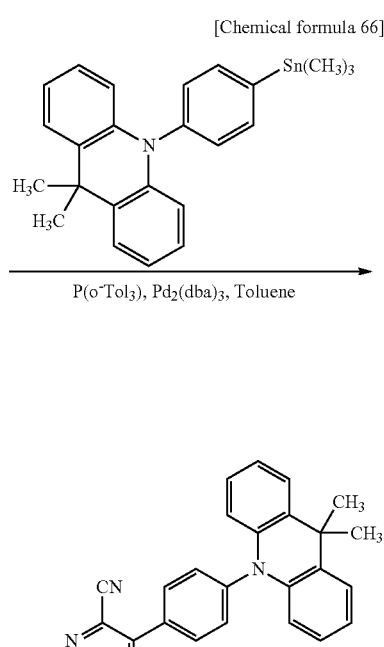
EXAMPLE II-2
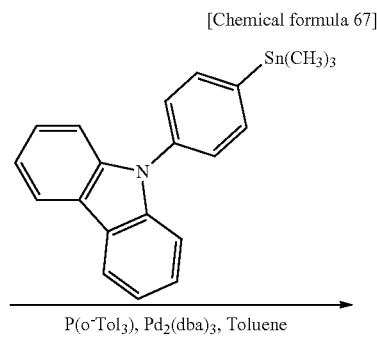

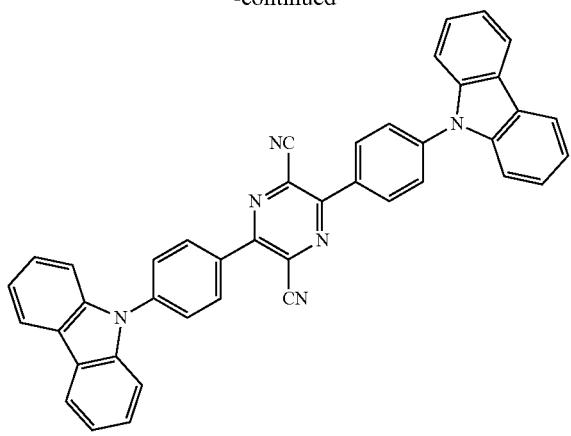

Purification of these compounds can be carried out by purification by column chromatography, adsorption purification with silica gel, activated carbon, activated clay or the like, extraction with a solvent, recrystallization or crystallization method or the like. The structure of the compound can be determined by comparing the spectra of IR, NMR, Mass etc. to known structural isomers.

The method for producing a 2,5-dicyano-3,6-dihalogenopyrazine of the present invention includes:

(1st Step) reacting (2E)-2,3-diamino-3-(substituted sulfanyl)-2-propenenitrile in the presence of oxygen under acidic conditions to obtain 2,5-dicyano-3,6-diaminopyrazine.

(2nd Step) subjecting the 2,5-dicyano-3,6-diaminopyrazine to a halogenation reaction in the presence of nitrous acid or nitrite in a solvent.

[Chemical formula 68]

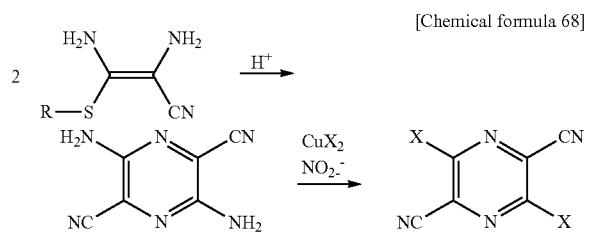

In the formula, X represents a halogen atom, R represents a substituted or unsubstituted aryl group, a substituted or unsubstituted alkyl group, a substituted or unsubstituted aralkyl group, or a substituted or unsubstituted alkenyl group. R is preferably a substituted or unsubstituted aryl group, and more preferably a phenyl group.

(2E)-2,3-diamino-3-(substituted sulfanyl)-2-propenenitrile (for example, a compound represented by formula (9)) which is a raw material can be easily synthesized by a method described in Patent Document 10 or the like. (2E)-2,3-diamino-3-(substituted sulfanyl)-2-propenenitrile may be in the form of an acidic salt in an acidic solution.

Therefore, the reaction in the first step can be carried out (a) by dissolving (2E)-2,3-diamino-3-(substituted sulfanyl)-2-propenenitrile in an acidic solution, or (b) by dissolving an acidic salt of (2E)-2,3-diamino-3-(substituted sulfanyl)-2-propenenitrile in a solvent.

The reaction (a) is usually carried out in the presence of an organic solvent or a mixed type of an organic solvent and water, in the presence of an acid for adjusting the pH or a buffer solution, while blowing air according to need, at around 0 to 30° C. for 1 to a few hour under atmospheric pressure.

Examples of the organic solvent include hydrocarbons s as a benzene, toluene, xylene or the like, nitrites such as an acetonitrile or the like, halogenated hydrocarbons such as a chloroform and methylene chloride or the like, esters such as an ethyl acetate or the like, alcohols such as a methanol, ethanol or the like, ketones such as an acetone, methyl ethyl ketone or the like, ethers such as a diethyl ether, tetrahydrofuran, dioxane, 1,2-dimethoxyethane (DME), dimethylformamide, dimethyl sulfoxide (DMSO), and the like. These organic solvents may be used alone or in combination of two or more.

The pH, which is an index of acidity, is preferably 1 to 5, more preferably 2 to 4. For adjusting the pH, although any acid such as an inorganic acid or organic acid can be used, it is preferable to use various buffers.

In addition, the reaction in the first step is considered to be an oxidative dimerization condensation reaction. Therefore, it is necessary to make the system an oxidizing atmosphere. Normally, it is only necessary to bring it into contact with atmospheric oxygen, but it is preferable that air, oxygen or the like is actively blown into the reaction system.

In the reaction (b), a solvent capable of dissolving the acidic salt of the compound represented by formula (1), for example, a polar solvent such as an acetonitrile, alcohols, dimethylformamide, dimethylsulfoxide or the like, or a mixed solvent thereof can be used. These solvents may contain water. Although the reaction can be carried out at room temperature for 2 to 12 hours, it is desirable to make the reaction system an oxidizing atmosphere by blowing air or the like as in the reaction (a).

Examples of the acidic salt of the compound represented by formula (1) include inorganic acid salts such as a hydrochloride, sulfate, nitrate, perchlorate or the like, organic acid salts such as a p-toluenesulfonate, oxalate, picrate, trifluoroacetate or the like, and the like.

By the reaction of the first step, 2,5-dicyano-3,6-diaminopyrazine is produced. After completion of the reaction in the first step, 5-dicyano-3,6-diaminopyrazine can be isolated according to need by carrying out usual post-treatments.

Examples of the nitrite used in the reaction in the second step include metal nitrites such as a sodium nitrite, potassium nitrite or the like; nitrite esters such as an n-butyl nitrite, t-butyl nitrite, isobutyl nitrite, amyl nitrite, isoamyl nitrite, hexyl nitrite, isoamyl nitrite or the like, and the like. From the viewpoint of purification, nitrite esters are preferable. Generally, it is said that diazotization of an amino group proceeds by the action of nitrous acid or nitrite to form a diazonium salt. Although the amount of nitrous acid or nitrite to be used is not particularly limited, it is preferably 2 mol or more, and more preferably 2.5 to 5 mol, with respect to 1 mol of 2,5-dicyano-3,6-diaminopyrazine.

Examples of the halogenating agent include tetrafluoroboric acid, copper (I) bromide, copper (II) bromide, copper (I) chloride, copper (II) chloride, potassium iodide and the like. The amount of the halogenating agent to be used is not particularly limited as long as it is an amount sufficient for brominating two amino groups in 2,5-dicyano-3,6-diaminopyrazine.

Examples of the reaction solvent include hydrocarbons such as a benzene, toluene, xylene or the like, nitriles such as an acetonitrile or the like, halogenated hydrocarbons such as a chloroform, methylene chloride or the like, esters such as an ethyl acetate or the like, alcohols such as a methanol, ethanol or the like, ketones such as acetone, methyl ethyl ketone or the like, ethers such as a diethyl ether, tetrahydrofuran, dioxane, 1,2-dimethoxyethane (DME) or the like, dimethylformamide, dimethylsulfoxide (DMSO), and these solvents can be mixed to use.

In the reaction of the second step, 2,5-dicyano-3,6-diaminopyrazine may be added to a solution containing a halogenating agent and nitrous acid or nitrite; or nitrite or nitrite may be added to a solution containing 2,5-dicyano-3,6-diaminopyrazine and a halogenating agent; or other addition orders may be used. However, since it is easy to control the heat generation and foaming during the reaction, it is preferable to add nitrous acid or nitrite to a solution containing 2,5-dicyano-3,6-diaminopyrazine and a halogenating agent to carry out the reaction. The addition is preferably carried out slowly to suppress sudden heat generation or foaming.

Although the temperature during the reaction in the second step is not particularly limited, it is preferably 10 to 80° C., more preferably 20 to 70° C., and even more preferably 30 to 60° C. The reaction in the second step is almost complete when 2,5-dicyano-3,6-diaminopyrazine, halogenating agent, and nitrite or nitrite coexist in one reaction system, specifically at the end of the addition. If the reaction is kept at a high temperature even after completion of the reaction, the product may decompose. Therefore, in order to suppress decomposition of the product after completion of the reaction, it is preferable to cool down to room temperature or lower.

By the reaction in the second step, 2,5-dicyano-3,6-dihalogenopyrazine is produced. After completion of the reaction in the second step, 2,5-dicyano-3,6-dihalogenopyrazine can be isolated according to need by carrying out usual post-treatments.

The compound of the present invention can be used as a luminescent material. The luminescent material of the present invention can provide a luminescence device such as an organic photoluminescence device or an organic electroluminescence device. Since the compound of the present invention has a function of assisting luminescence of other luminescent materials (host material), it can be doped with other luminescent materials to use.

The organic photoluminescence device of the present invention is provided with a luminescent layer containing the luminescent material of the present invention on a substrate. The luminescent layer can be obtained by a coating method such as a spin coating or the like, a printing method such as an inkjet printing method or the like, a vapor deposition method, or the like.

The organic electroluminescence device of the present invention includes an organic layer provided between an anode and a cathode. The term "organic layer" in the present invention means a layer located between an anode and a cathodes and substantially composed of an organic substance, and these layers may contain an inorganic substance within a range not impairing the performance of the luminescence device of the present invention.

As a structure of one embodiment of the organic electroluminescence device of the present invention, a structure in which an anode, a hole injection layer, a hole transport layer, an electron blocking layer, a luminescent layer, a hole blocking layer, an electron transport layer, and a cathode are formed on a substrate in this order, and a structure having an electron injection layer between the electron transport layer and the cathode can be mentioned. In these multilayer structures, it is possible to omit several layers of the organic layers. For example, it can be a structure forming an anode, a hole transport layer, a luminescent layer, an electron transport layer, an electron injection layer and a cathode on a substrate in this order, or a structure forming an anode, a hole transport layer, a luminescent layer, an electron transport layer and a cathode on a substrate in this order. The luminescent material of the present invention may be doped in not only the luminescent layer but also the hole injection layer, the hole transport layer, the electron blocking layer, the hole blocking layer, the electron transport layer, or the electron injection layer.

The substrate serves as a support of the luminescence device, and a silicon plate, a quartz plate, a glass plate, a metal plate, a metal foil, a resin film, a resin sheet or the like can be used. In particular, a glass plate and a transparent synthetic resin plate such as polyester, polymethacrylate, polycarbonate, polysulfone or the like are preferable. When a synthetic resin substrate is used, it is necessary to pay attention to gas barrier properties. If the gas barrier property of the substrate is too low, the luminescence device may be deteriorated by the outside air passing through the substrate. Therefore, it is preferable to provide a dense silicon oxide film or the like on either side or both sides of the synthetic resin substrate to ensure gas barrier properties.

The substrate is provided with an anode. In general, a material having a high work function is used for the anode. Examples of materials for the anode include metals such as aluminum, gold, silver, nickel, palladium and platinum or the like; metal oxides such as indium oxide, tin oxide, ITO, zinc oxide, $In_2O_3$—ZnO, IGZO or the like; halogenated metals such as copper iodide or the like, carbon black, conductive polymers such as poly (3-methylthiophene), polypyrrole, polyaniline or the like, and the like. In general, in many cases, the formation of the anode is performed by a sputtering method, a vacuum evaporation method, or the like. Further, when metal fine particles such as silver or the like, fine particles such as copper iodide or the like, carbon black, conductive metal oxide fine particles, conductive polymer fine powder and the like are used, the anode can also be formed by dispersing them in an appropriate binder resin solution and coating it on a substrate. Furthermore, when a conductive polymer is used, it is also possible to form a thin film directly on the substrate by electropolymerization, or to form an anode by coating a conductive polymer on the substrate.

It is also possible to form the anode by laminating two or more different substances. The thickness of the anode depends on a transparency to be required. In the case where a transparency is required, it is desirable that a transmittance of visible light is usually 60% or more, preferably 80% or more, and in this case, the thickness is usually from 10 to 1000 nm, preferably from 10 to 200 nm. If it can be opaque, the anode may be as thick as the substrate. The sheet resistance of the anode is preferably several hundred Ω/□ or more.

As the hole injection layer provided as necessary, naphthalenediamine derivatives, starburst type triphenylamine derivatives, triphenylamine trimers and tetramers such as arylamine compounds having three or more triphenylamine structures connected by a single bond or by a divalent group not containing a hetero atom, acceptor heterocyclic compounds such as a hexacyanoazatriphenylene and a coating type polymer material can be used in addition to porphyrin compounds typified by copper phthalocyanine. Other than the vapor deposition method, these materials can be formed into thin films by a known method such as a spin coating method or an ink jet method.

As the hole transport material used for the hole transport layer provided as necessary, it is preferable that the hole injection efficiency from the anode is high and that the injected holes can be efficiently transported. To that end, it is preferable that the ionization potential is small, the transparency to visible light is high, the hole mobility is high, the stability is excellent, and impurities which become traps are hardly generated at the time of production or use. In addition to the above general requirement, when considering the application for on-vehicle display, it is preferable that the device has higher heat resistance. Therefore, a material having a Tg value of 70° C. or higher is desirable.

Examples of the hole transport layer provided as necessary include triazole derivatives, oxadiazole derivatives, imidazole derivatives, carbazole derivatives, indolocarbazole derivatives, polyarylalkane derivatives, pyrazoline derivatives, pyrazolone derivatives, phenylenediamine derivatives, arylamine derivatives, amino substituted chalcone derivatives, oxazole derivatives, styryl anthracene derivative, fluorenone derivative, hydrazone derivatives, stilbene derivatives, silazane derivatives, aniline type copolymer, conductive polymer oligomer and the like. More specifically, a compound containing an m-carbazolylphenyl group, N,N'-diphenyl-N, N'-di(m-tolyl)-benzidine (hereinafter abbreviated as TPD), N,N'-diphenyl-N,N'-di(α-naphthyl)-benzidine (hereinafter abbreviated as NPD), benzidine derivatives such as N,N,N',N'-tetrabiphenylyl benzidine or the like, 1,1-bis [(di-4-tolylamino) phenyl] cyclohexane (hereinafter abbreviated as TAPC), various triphenylamine trimers, tetramers, carbazole derivatives or the like, and the like. These can be used alone or in combination of two or more. The hole transport layer may be a film of a single layer structure or a film of a laminate structure. In addition, as a hole injection transport layer, a coating type polymer material such as poly (3,4-ethylenedioxythiophene) (hereinafter abbreviated as PEDOT)/poly (styrene sulfonate) (hereinafter abbreviated as PSS) can be used. In addition to the vapor deposition method, these materials can be formed into thin films by a known method such as a spin coating method or an ink jet method.

Further, in the hole injection layer or the hole transport layer, a P-doped tris bromophenylamine hexachloroantimony, a polymer compound having the structure of PD in its partial structure, and the like can be used other than the materials commonly used for the above layer. Carbazole derivatives such as CBP, TCTA, mCP and the like can be used as a host material of the hole injection/transport.

Compounds (hi1) to (hi7) which can be preferably used as the hole injection material are listed below.

[Chemical formula 69]

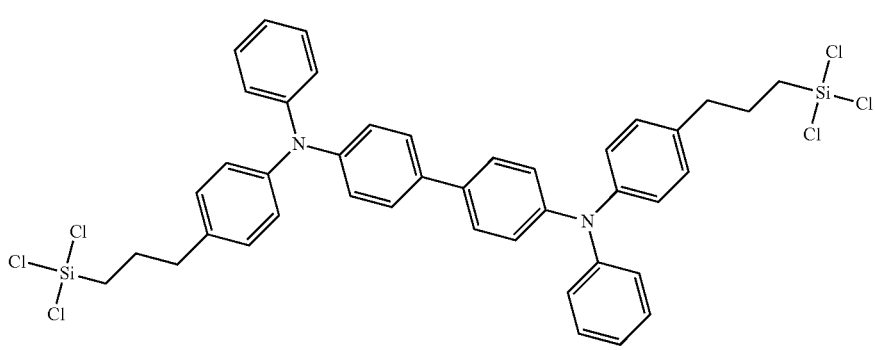

(hi1)

[Chemical formula 70]

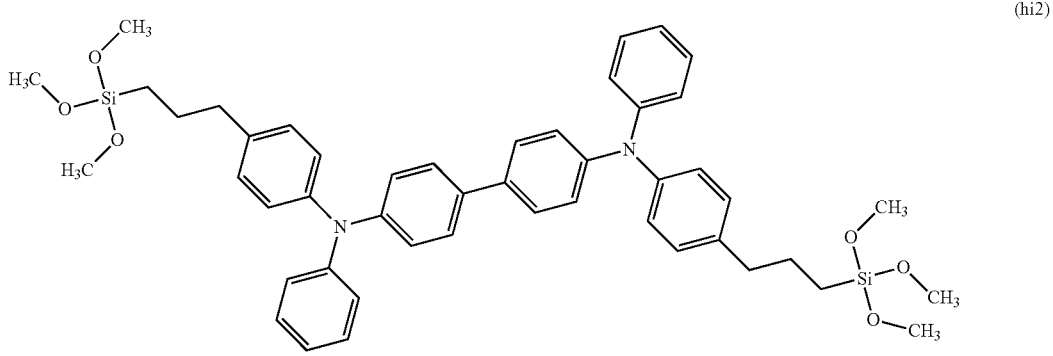

(hi2)

[Chemical formula 71]
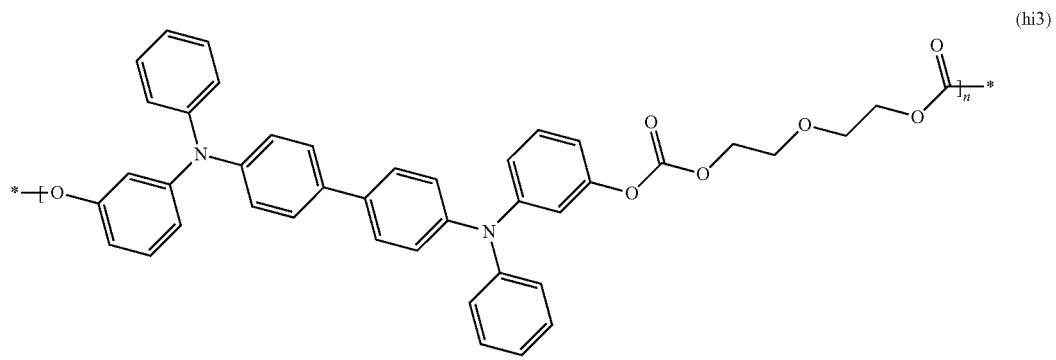
(hi3)
[Chemical formula 72]
(hi4)
[Chemical formula 73]
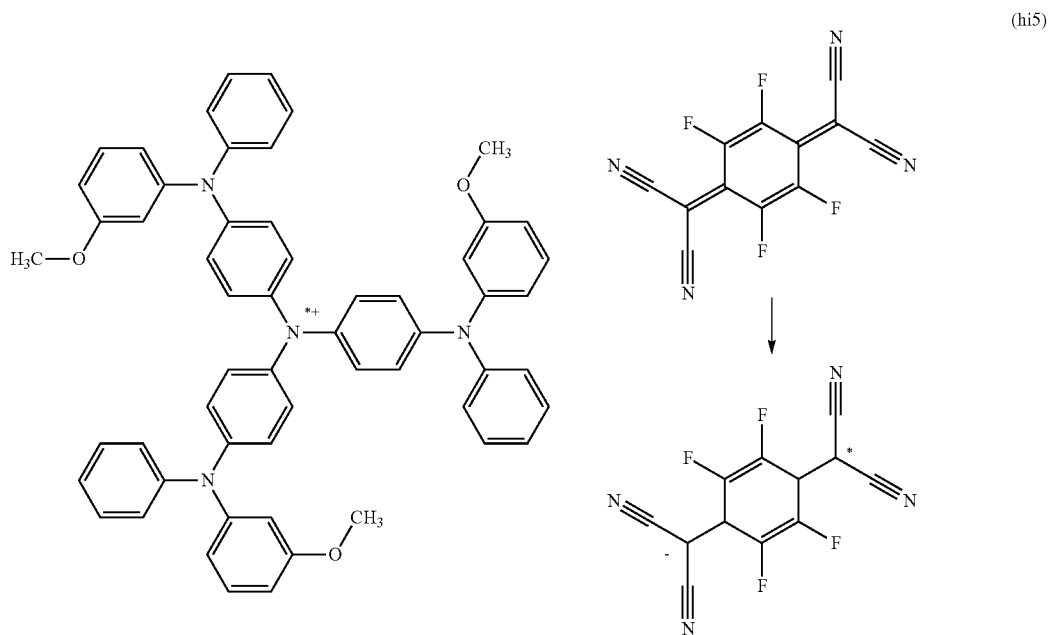
(hi5)

[Chemical formula 74]
(hi6)
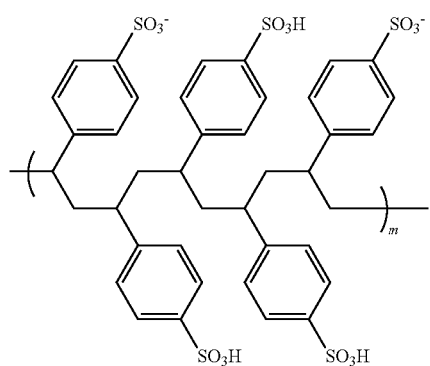
[Chemical formula 75]
(hi7)
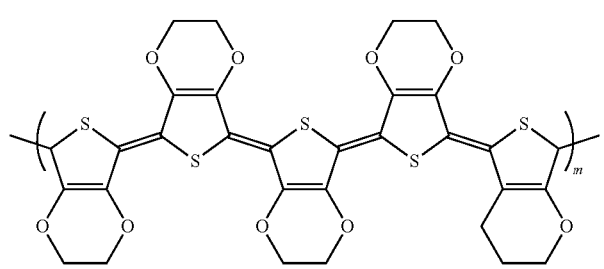
Compounds (ht1) to (ht38) which can be preferably used as the hole transport material are listed below.
[Chemical formula 76]
(ht1)
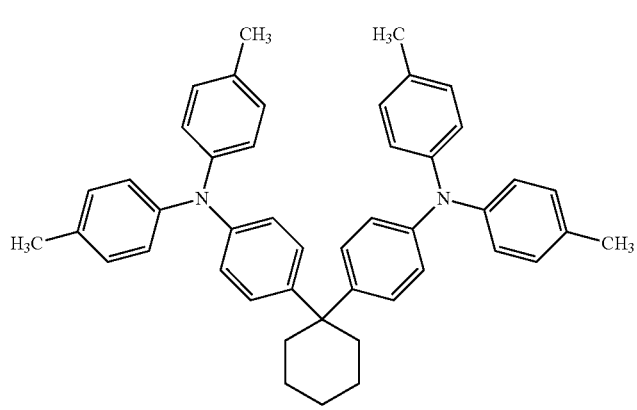
[Chemical formula 77]
(ht2)
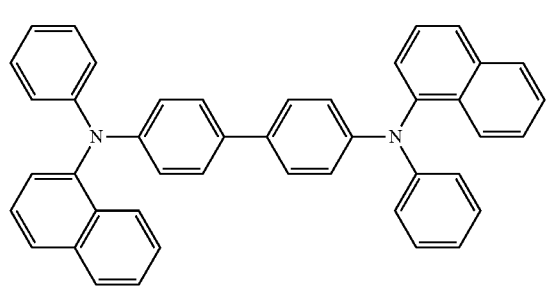

-continued
[Chemical formula 78]
(ht3)
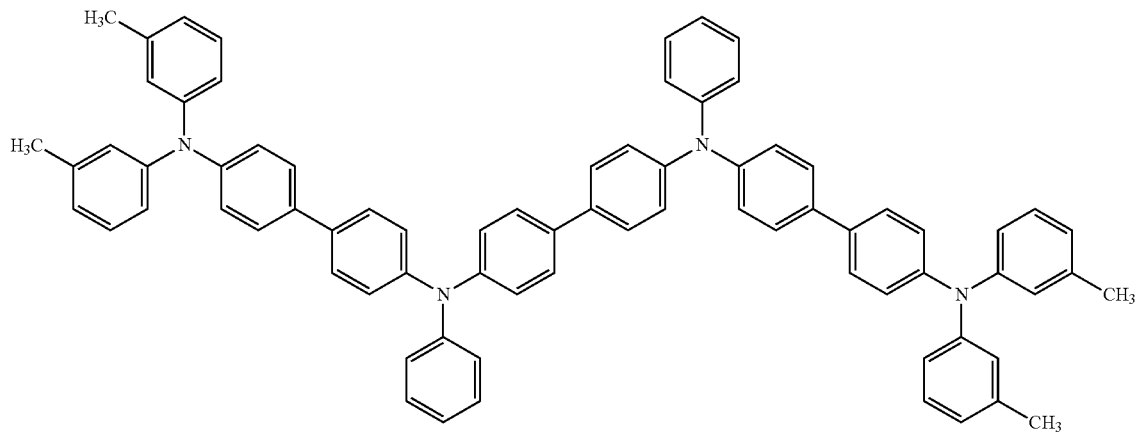
[Chemical formula 79]
(ht4)
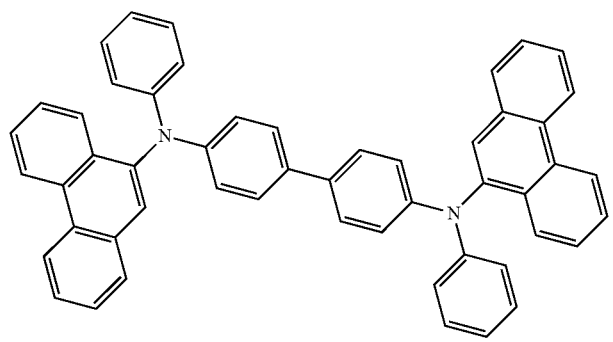
[Chemical formula 80]
(ht5)
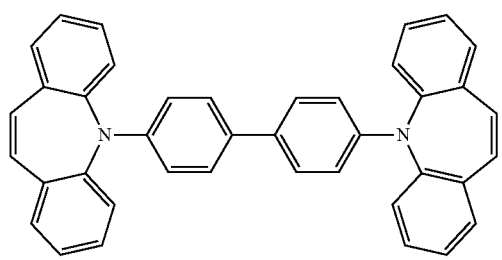
[Chemical formula 81]
(ht6)
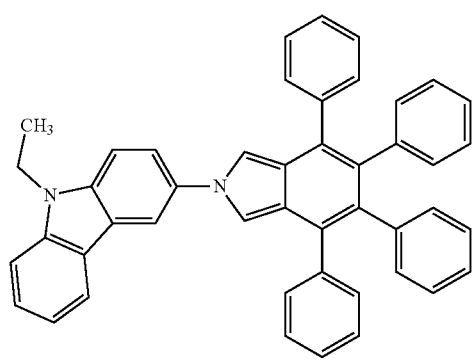

-continued
[Chemical formula 82]
(ht7)
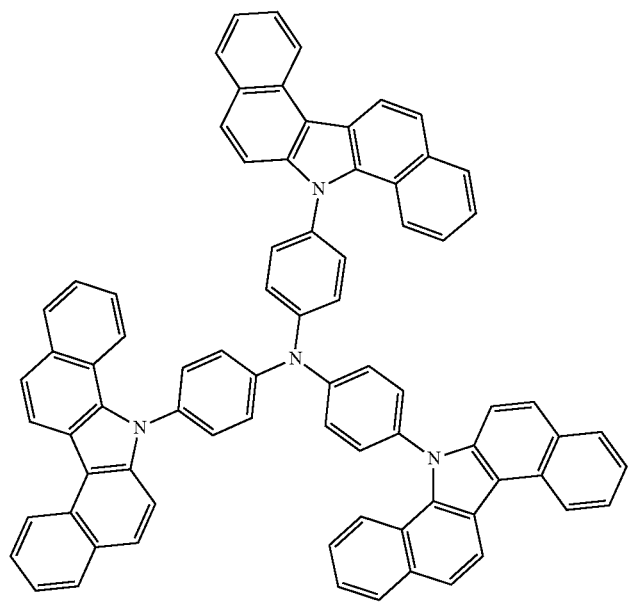
[Chemical formula 83]
(ht8)
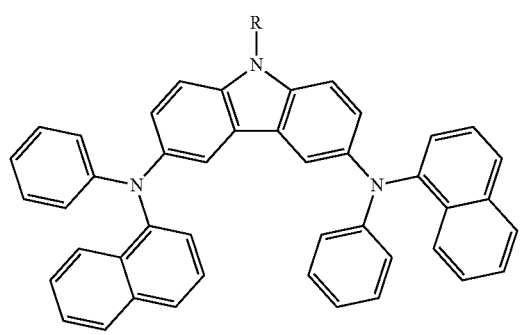
[Chemical formula 84]
(ht9)
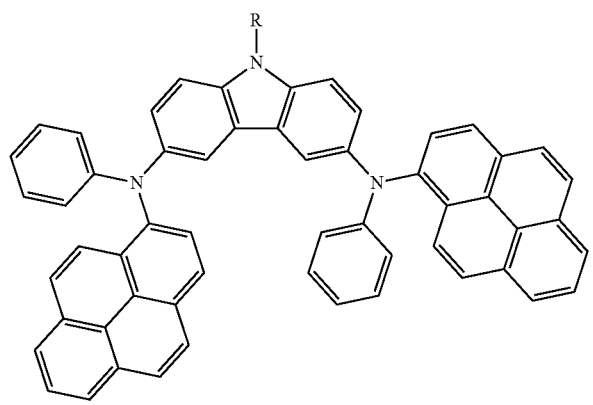

[Chemical formula 85]
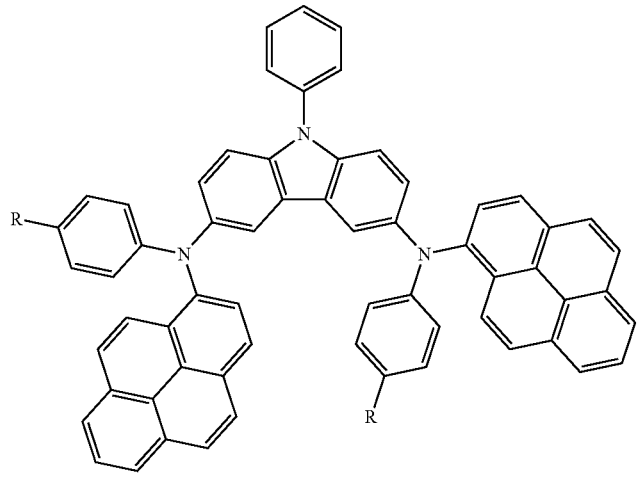
(ht10)
[Chemical formula 86]
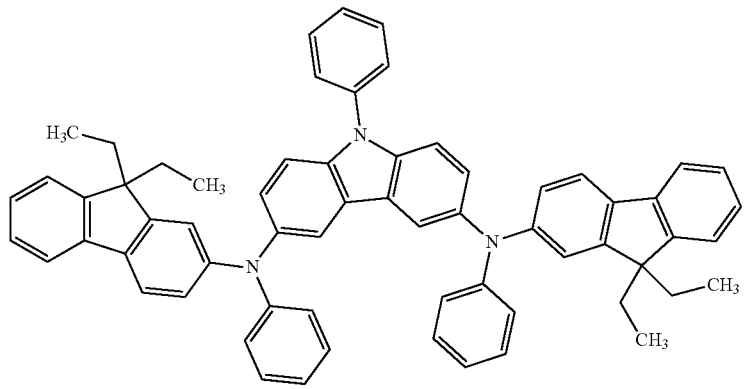
(ht11)
[Chemical formula 87]
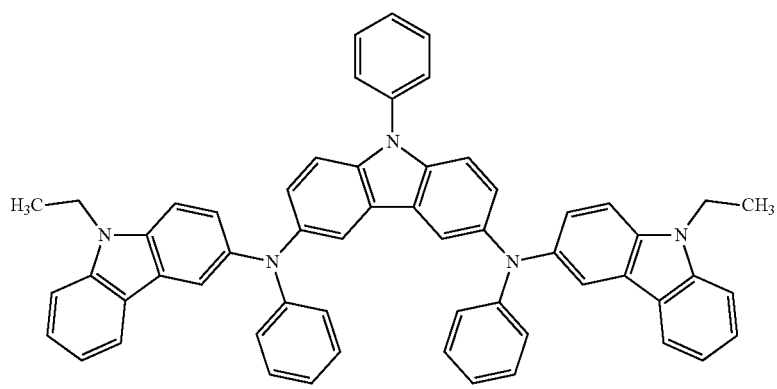
(ht12)

[Chemical formula 88]
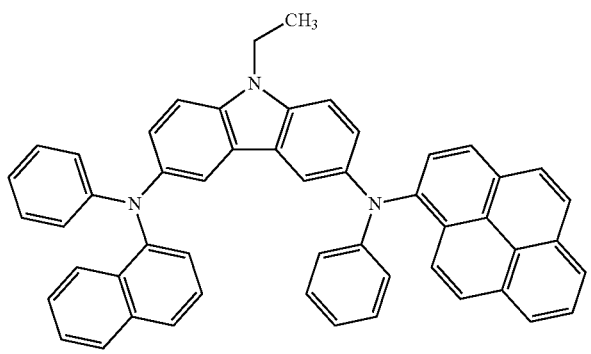
(ht13)
[Chemical formula 89]
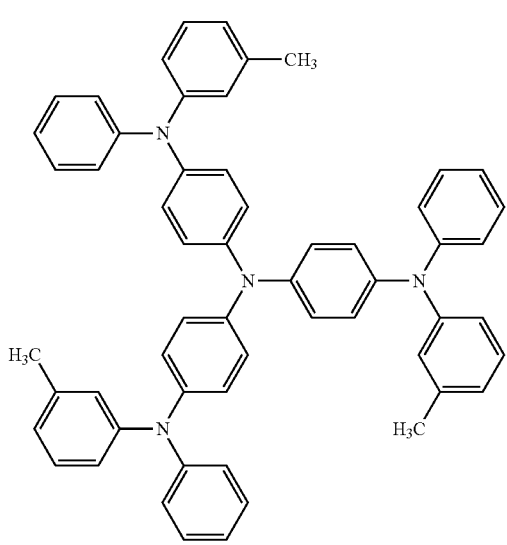
(ht14)
[Chemical formula 90]
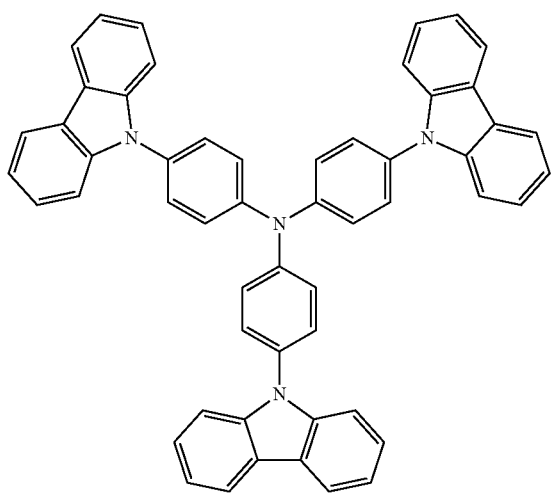
(ht15)

[Chemical formula 91]
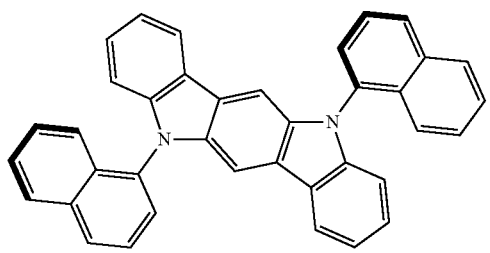
(ht16)
[Chemical formula 92]
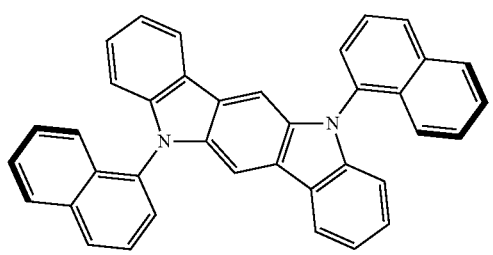
(ht17)
[Chemical formula 93]
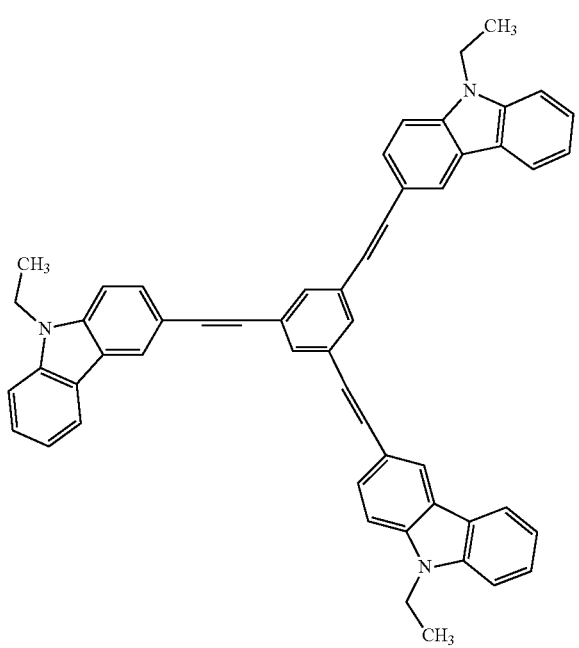
(ht18)

[Chemical formula 94]
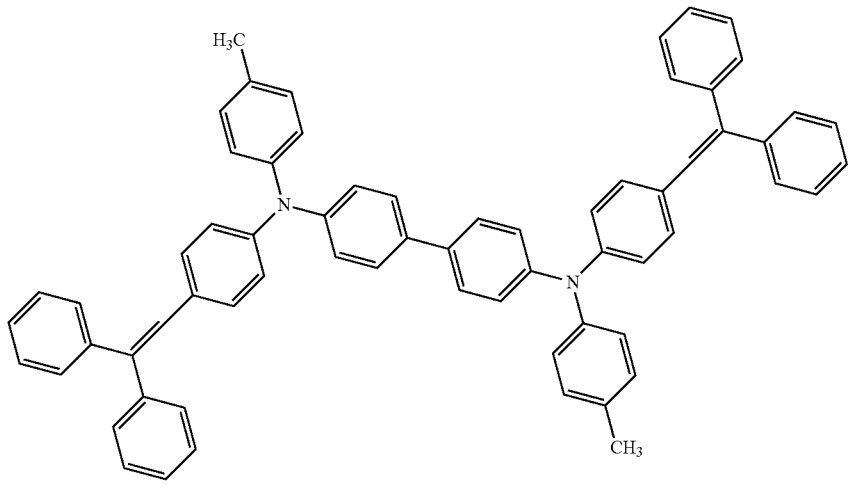
(ht19)
[Chemical formula 95]
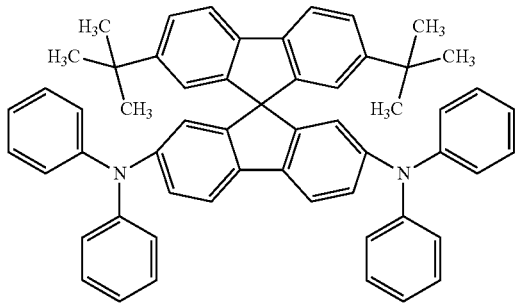
(ht20)
[Chemical formula 96]
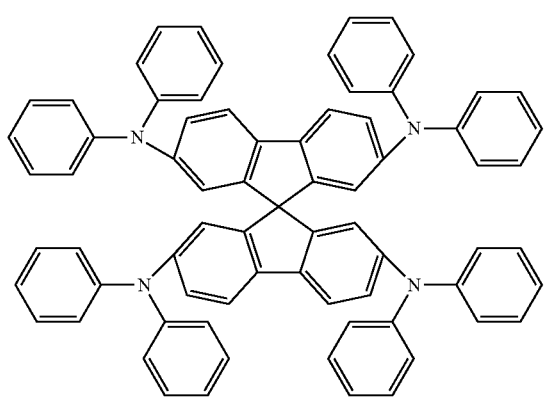
(ht21)

[Chemical formula 97]
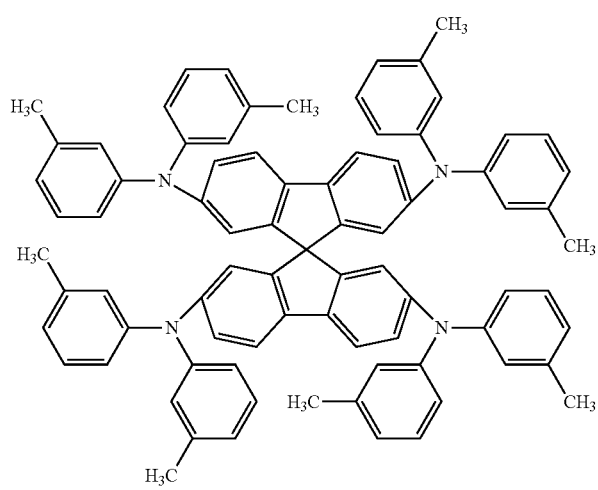
(ht22)
[Chemical formula 98]
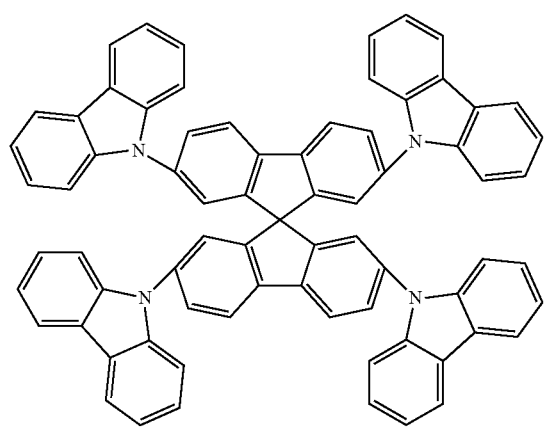
(ht23)
[Chemical formula 99]
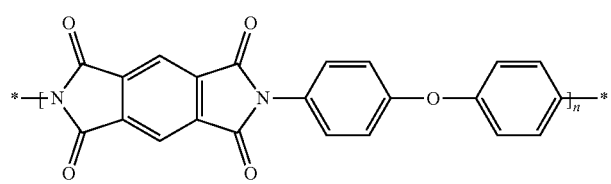
(ht24)
[Chemical formula 100]
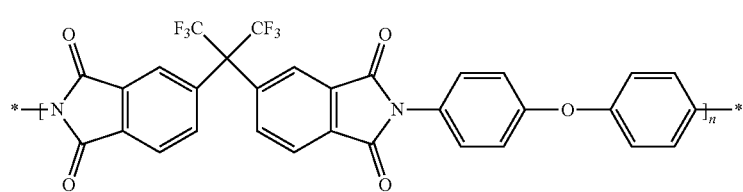
(ht25)

-continued
[Chemical formula 101]
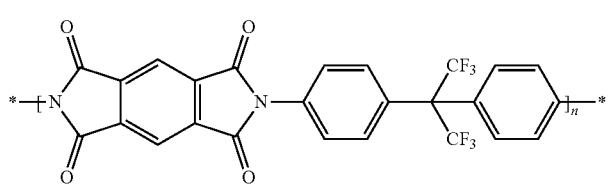
(ht26)
[Chemical formula 102]
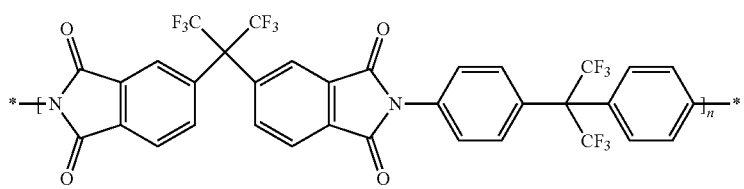
(ht27)
[Chemical formula 103]
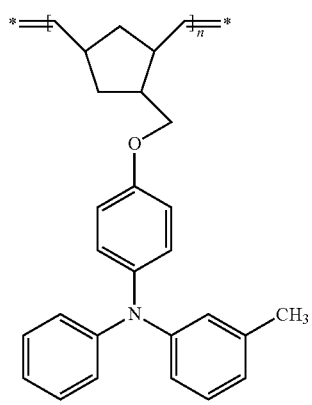
(ht28)
[Chemical formula 104]
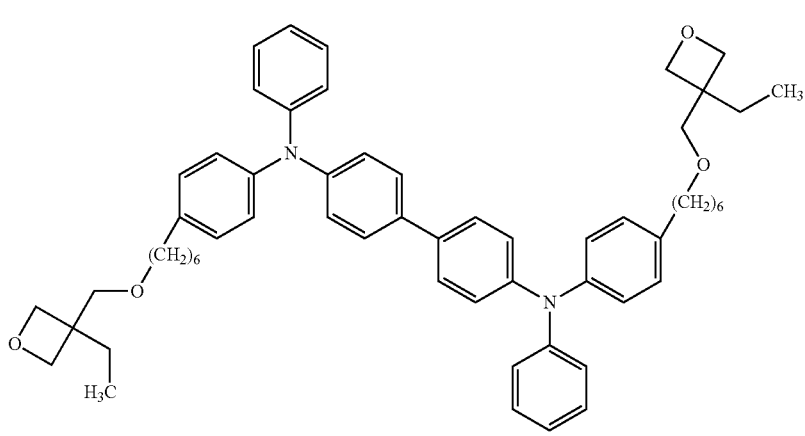
(ht29)

[Chemical formula 105]
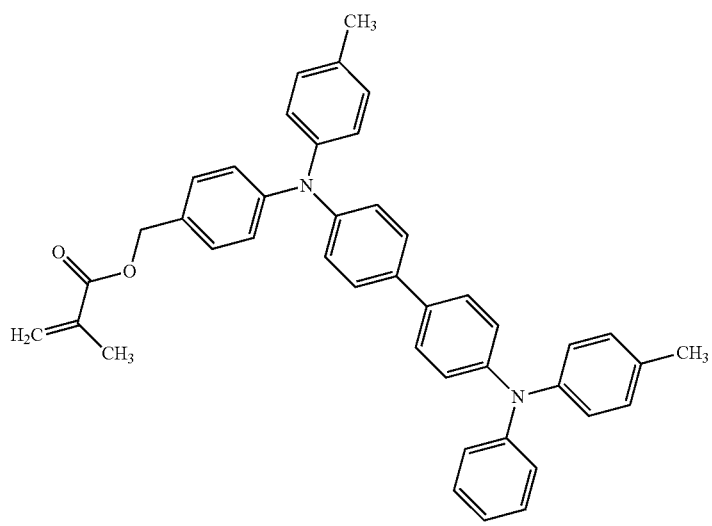
(ht30)
[Chemical formula 106]
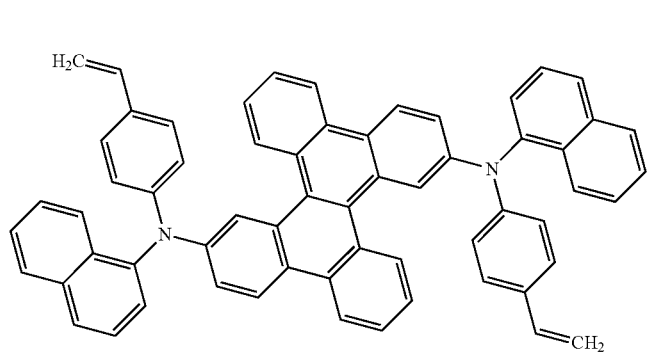
(ht31)
[Chemical formula 107]
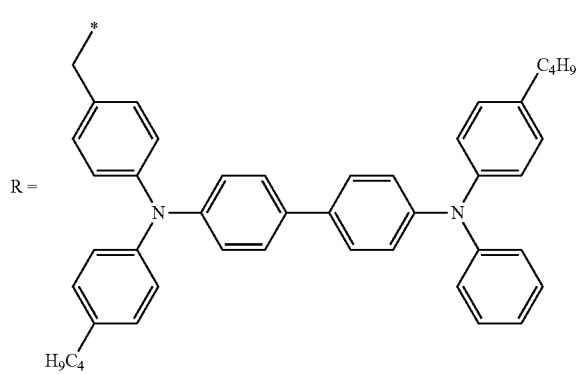
(ht32)

[Chemical formula 108]
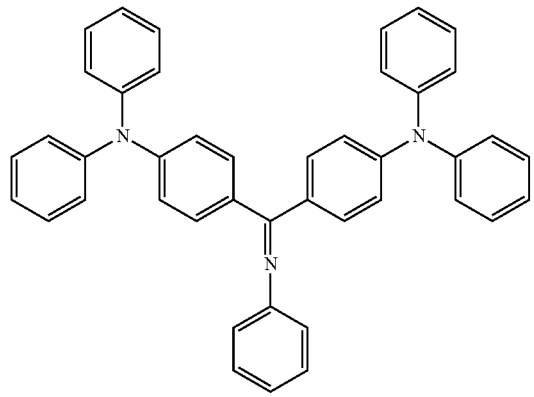
(ht33)
[Chemical formula 109]
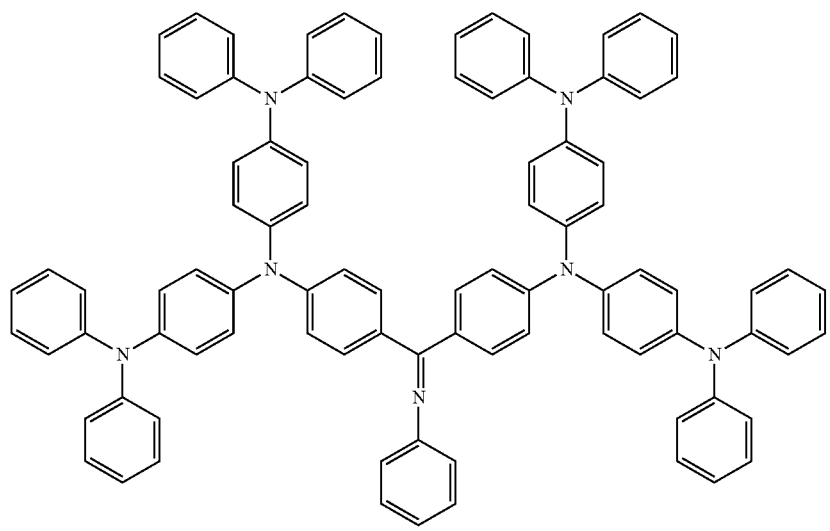
(ht34)
[Chemical formula 110]
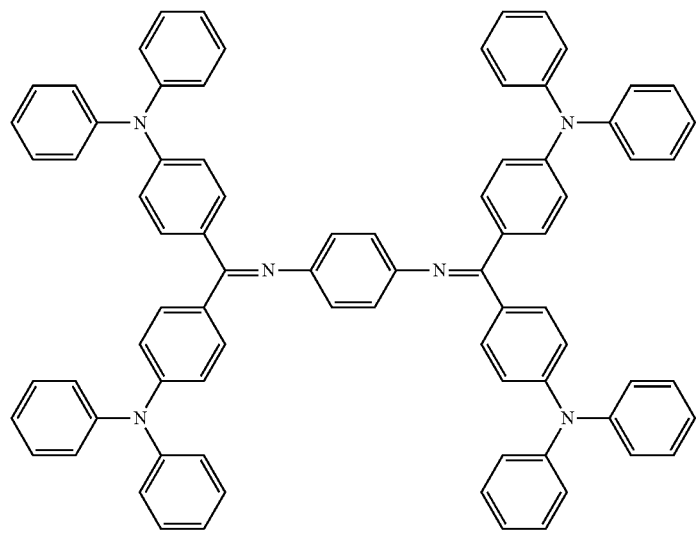
(ht35)

[Chemical formula 111]
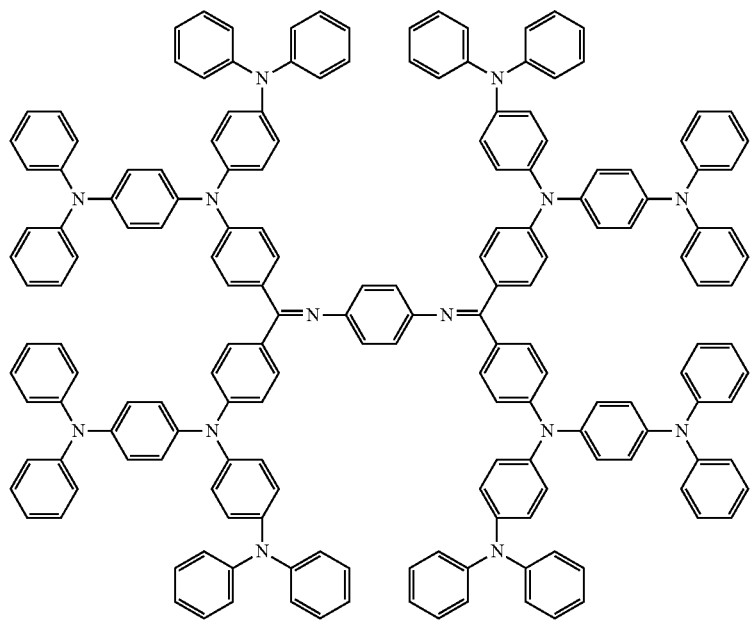
(ht36)
[Chemical formula 112]
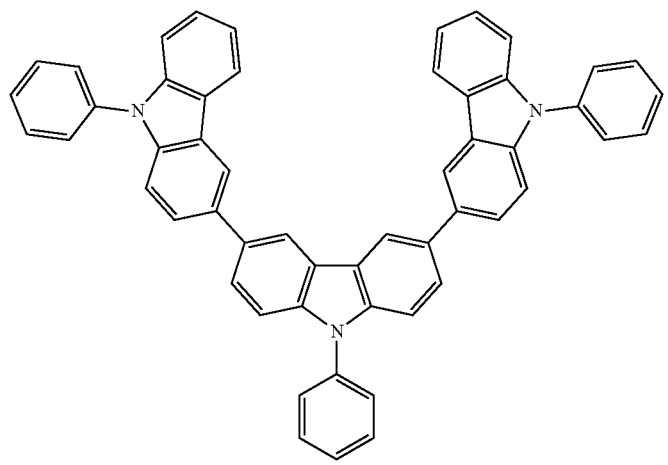
(ht37)
[Chemical formula 113]
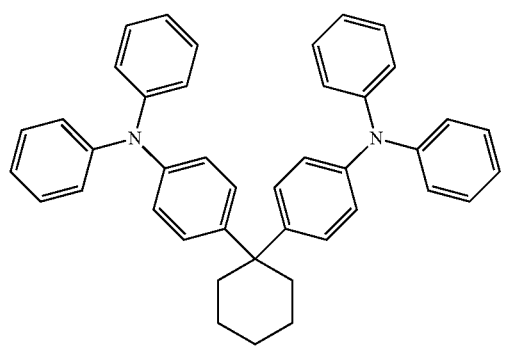
(ht38)

As the electron blocking layer provided as necessary, compounds having an electron blocking action, for example, carbazole derivatives such as 4,4',4"-tri (N-carbazolyl) triphenylamine (hereinafter abbreviated as TCTA), 9,9-bis[4-(carbazol-9-yl) phenyl] fluorene, 1,3-bis (carbazol-9-yl) benzene (hereinafter abbreviated as mCP), 2,2-bis (4-carbazol-9-ylphenyl) adamantane (hereinafter abbreviated as Ad-Cz) or the like, compounds having a triphenylsilyl group typified by 9-[4-(carbazol-9-yl) phenyl]-9-[4-(triphenylsilyl) phenyl]-9H-fluorene and a triarylamine structure can be used. These can be used alone or in combination of two or more. The electron blocking layer may be a film of a single layer structure or a film of a laminated structure. In addition to the vapor deposition method, these materials can be formed into thin films by a known method such as a spin coating method, an ink jet method or the like.

Compounds (es1) to (es5) which can be preferably used as the electron blocking material are listed below.

[Chemical formula 114]

(es1)

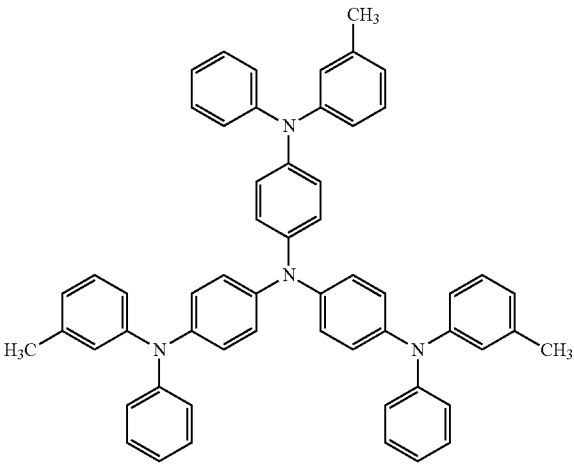

[Chemical formula 115]

(es2)

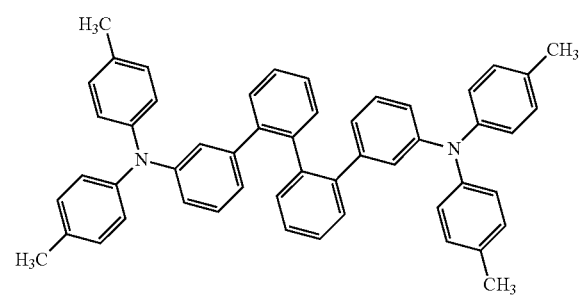

[Chemical formula 116]

(es3)

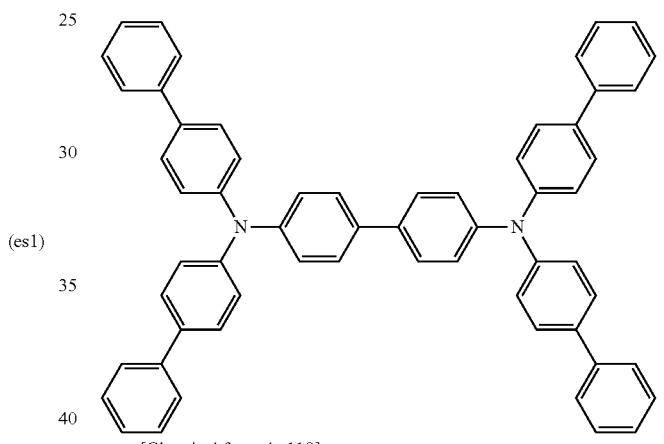

[Chemical formula 117]

(es4)

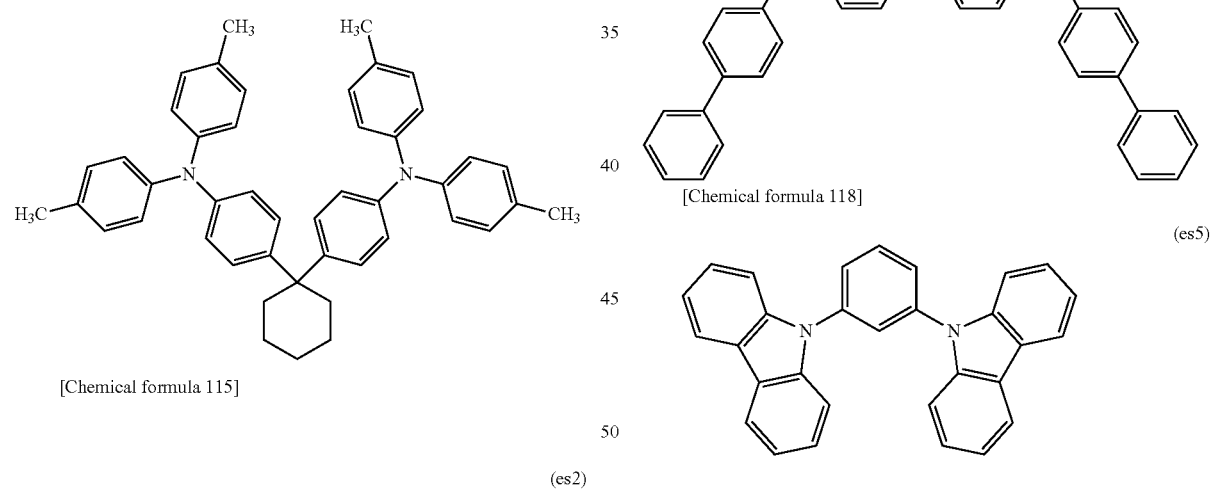

[Chemical formula 118]

(es5)

The luminescent layer is a layer having a function of generating excitons by recombination of the holes and the electrons injected from the anode and the cathode respectively to emit light. The luminescent layer may be formed of the luminescent material of the present invention alone, or may be formed by doping the luminescent material of the present invention in a host material. Examples of the host material include metal complexes of quinolinol derivatives such as a tris (8-hydroxyquinoline) aluminum (hereinafter abbreviated as Alq 3), an anthracene derivative, a bisstyrylbenzene derivative, a pyrene derivative, an oxazole derivatives, a polyparaphenylene vinylene derivative, a compound having a bipyridyl group and an orthopterphenyl structure, mCP, a thiazole derivative, a benzimidazole derivative, a polydialkylfluorene derivative and the like. The luminescent layer may contain a known dopant. As the dopant, a quinacridone, coumarin, rubrene, anthracene, perylene and derivatives thereof, benzopyran derivatives, rhodamine derivatives, aminostyryl derivatives and the like can be mentioned. In addition, a phosphorescent luminescent body, for example, a green phosphorescent luminescent body such as Ir(ppy)3 or the like, a blue phosphorescent luminescent body such as FIrpic, FIr 6 or the like, or a red phosphorescent luminescent body such as Btp2Ir (acac) or the like may be used. These can be used alone or in combination of two or more. The luminescent layer may be a film of a single layer structure or a film of a laminated structure. In addition to the vapor deposition method, these materials can be formed into thin films by a known method such as a spin coating method or an ink jet method.

In the case of using a host material, the lower limit of the amount of the luminescent material of the present invention that can be contained in the luminescent layer is preferably 0.1% by mass, more preferably 1% by mass, and the upper limit is preferably 50% by mass, more preferably 20% by mass, and even more preferably 10% by mass.

Compounds (el1)-(el40) which can be preferably used as the host material of the luminescent layer are listed below.

[Chemical formula 119]

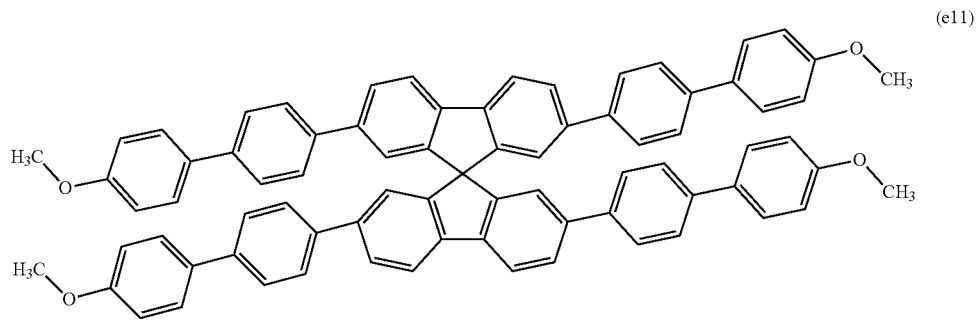

(el1)

[Chemical formula 120]

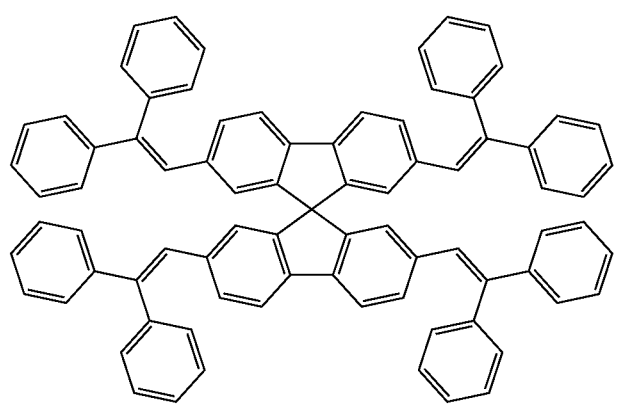

(el2)

[Chemical formula 121]

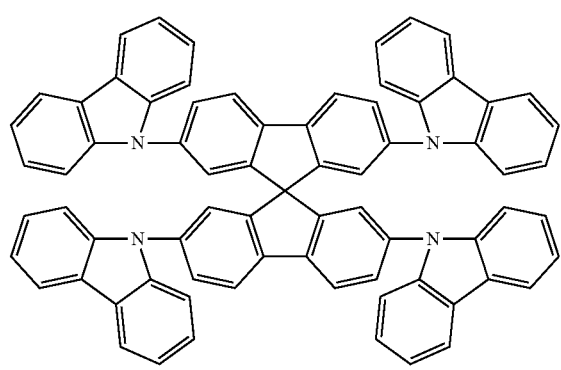

(el3)

[Chemical formula 122]
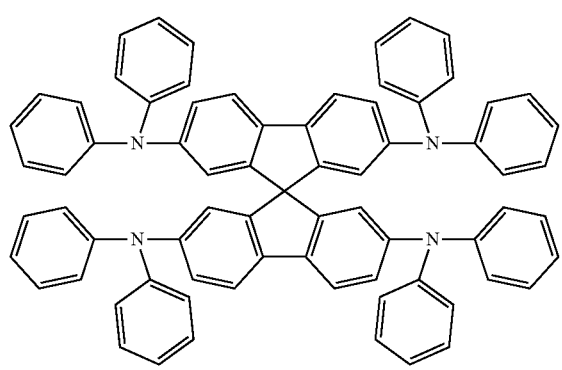
(e14)
[Chemical formula 123]
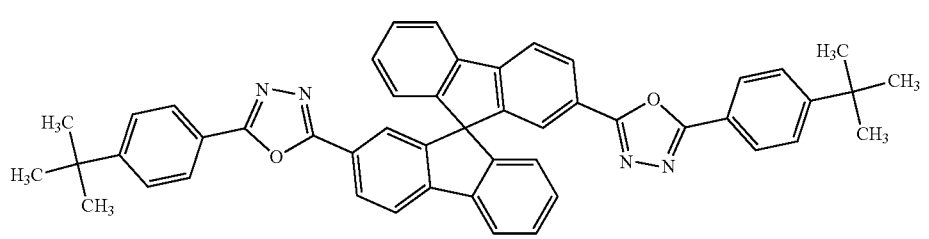
(e15)
[Chemical formula 124]
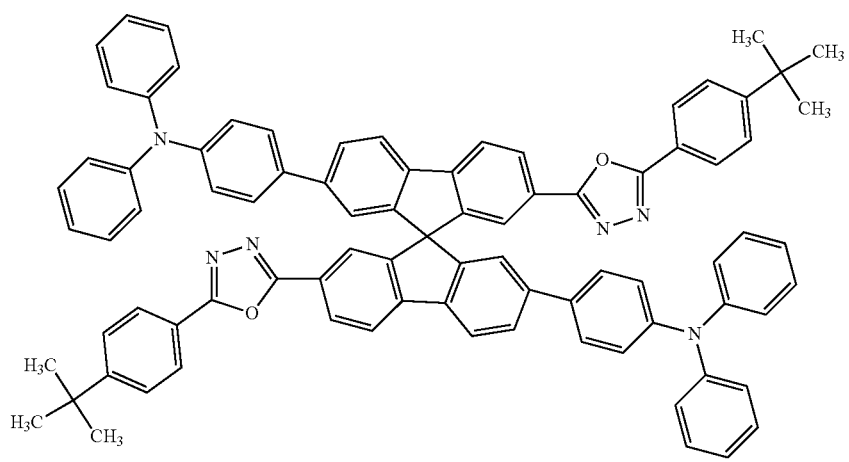
(e16)
[Chemical formula 125]
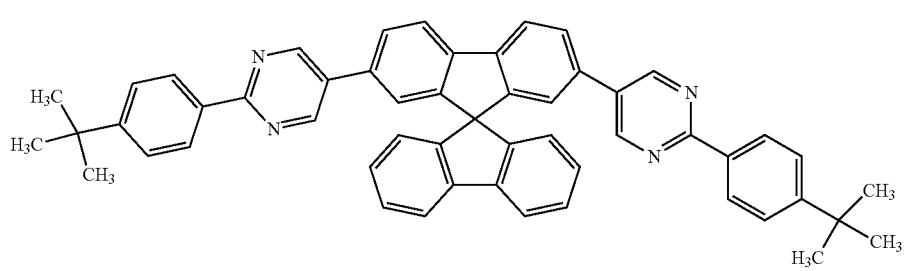
(e17)

[Chemical formula 126]
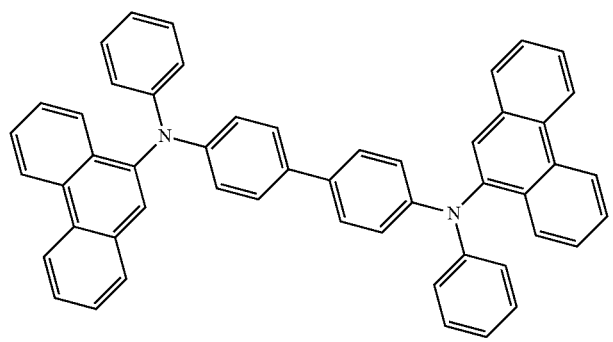
(e18)
[Chemical formula 127]
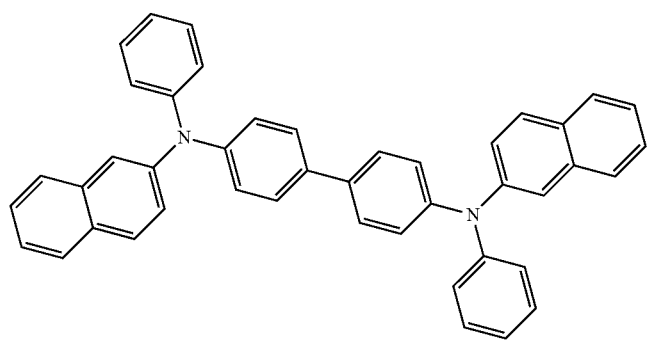
(e19)
[Chemical formula 128]
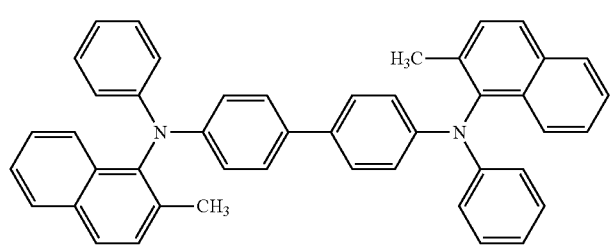
(e110)
[Chemical formula 129]
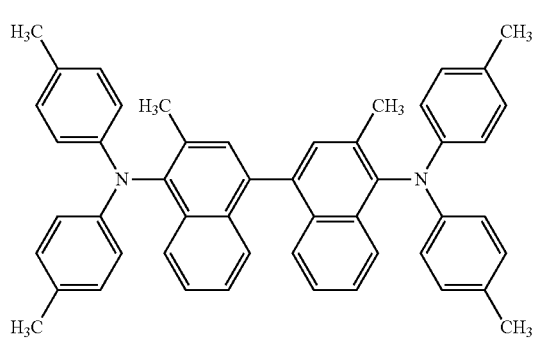
(e111)

[Chemical formula 130]
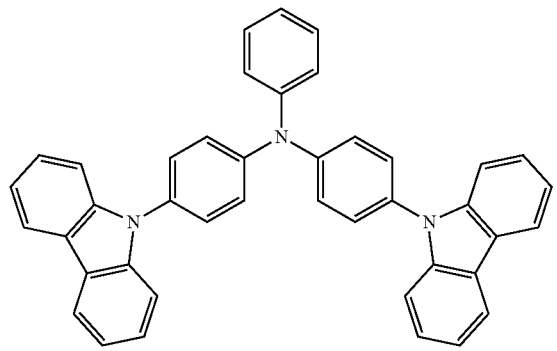
(e112)
[Chemical formula 131]
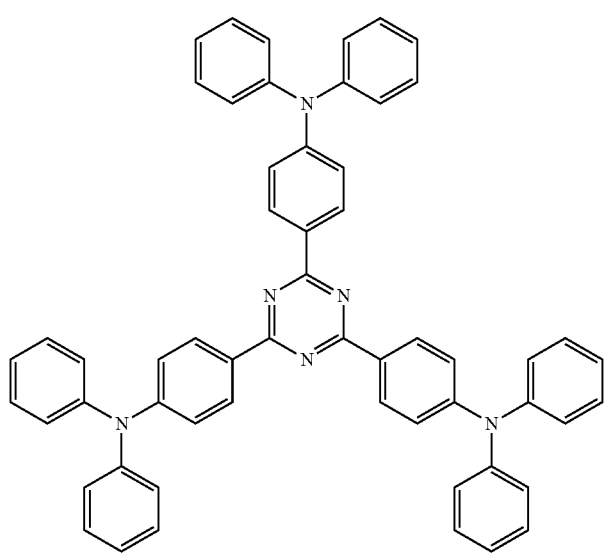
(e113)
[Chemical formula 132]
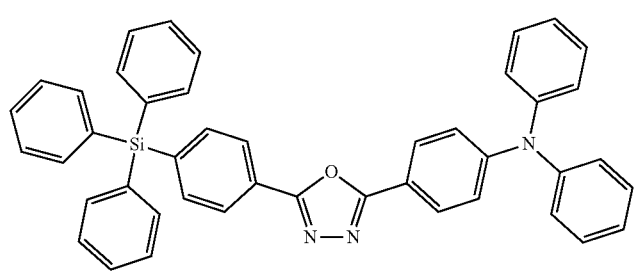
(e114)

[Chemical formula 133]
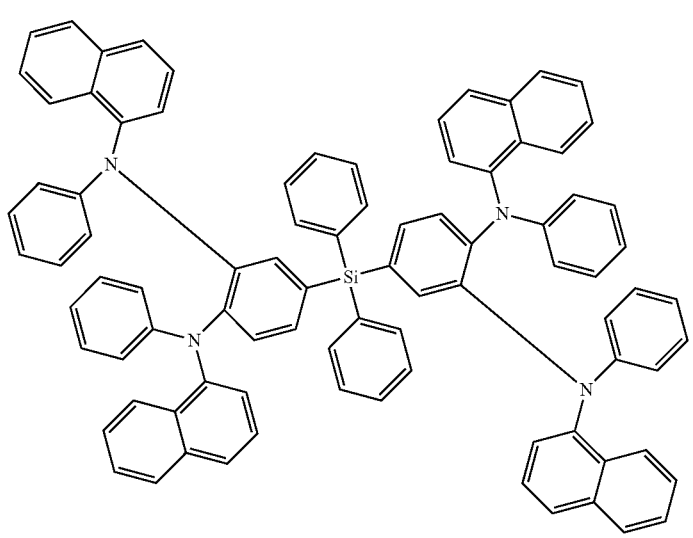
(e115)
[Chemical formula 134]
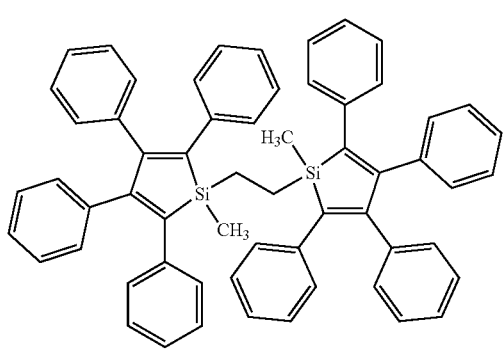
(e116)
[Chemical formula 135]
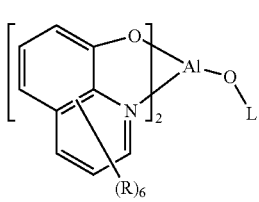
(e117)
[Chemical formula 136]
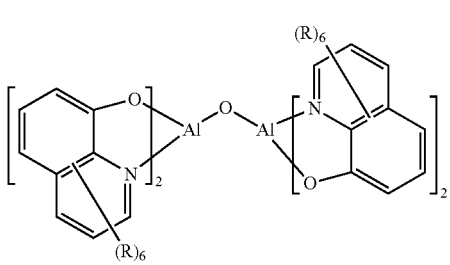
(e118)

-continued
[Chemical formula 137]
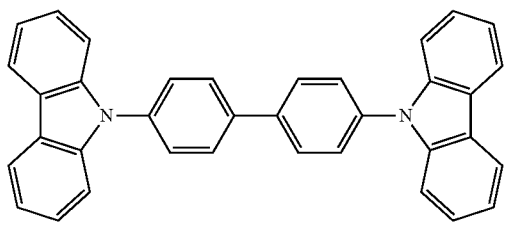
(e119)
[Chemical formula 138]
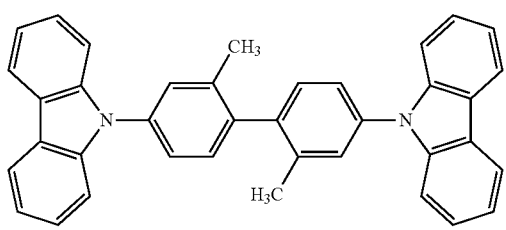
(e120)
[Chemical formula 139]
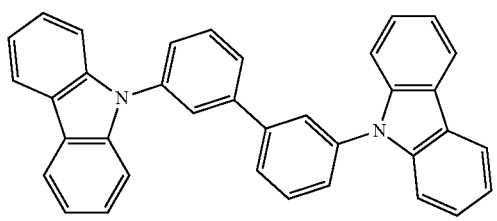
(e121)
[Chemical formula 140]
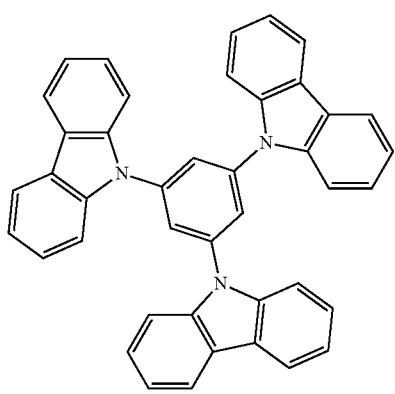
(e122)
[Chemical formula 141]
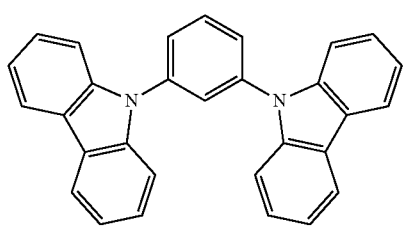
(e123)

[Chemical formula 142]
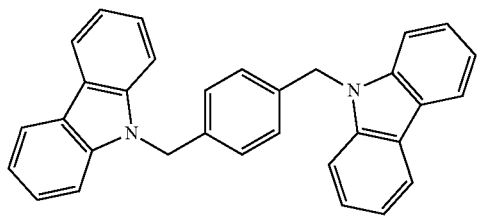
(e124)
[Chemical formula 143]
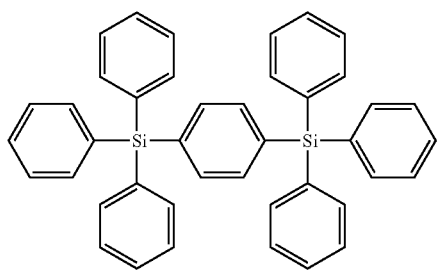
(e125)
[Chemical formula 144]
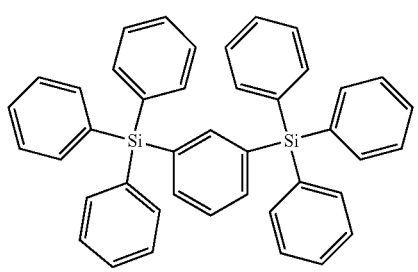
(e126)
[Chemical formula 145]
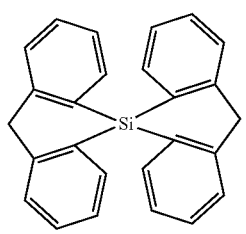
(e127)
[Chemical formula 146]
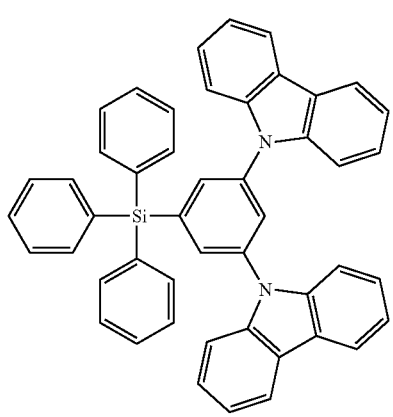
(e128)

-continued
[Chemical formula 147]
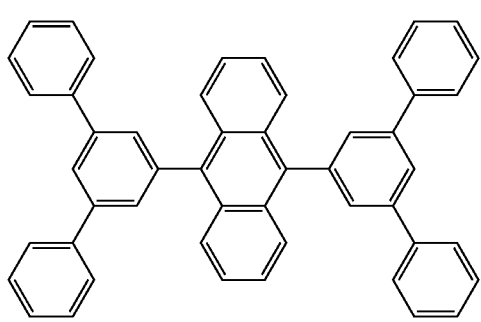
(e129)
[Chemical formula 148]
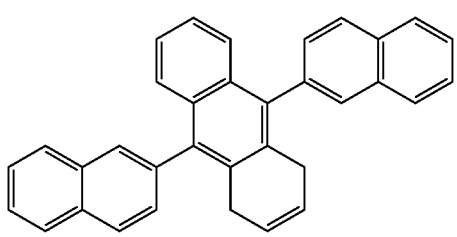
(e130)
[Chemical formula 149]
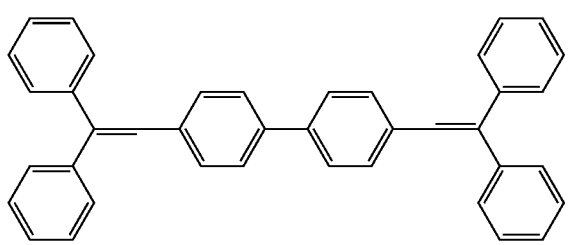
(e131)
[Chemical formula 150]
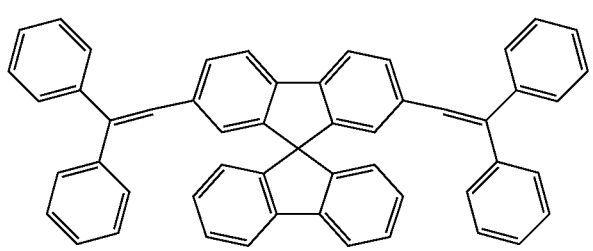
(e132)

[Chemical formula 151]
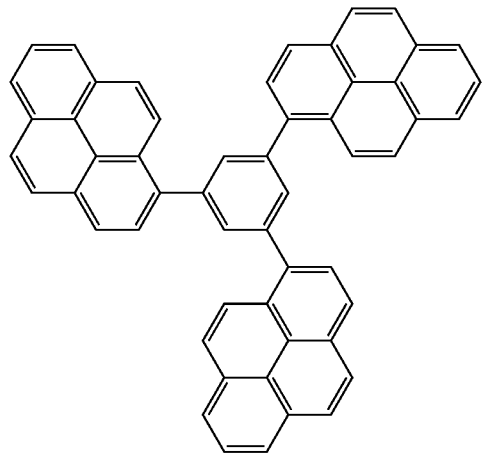
(e133)
[Chemical formula 152]
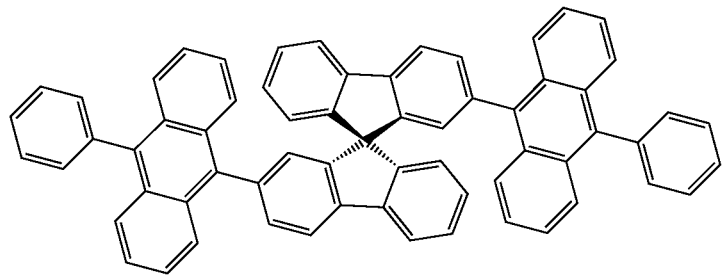
(e134)
[Chemical formula 153]
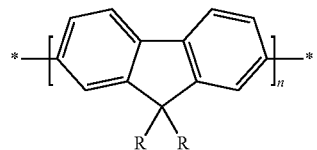
(e135)
[Chemical formula 154]
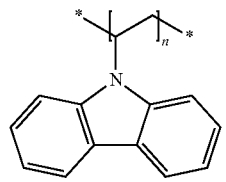
(e136)

[Chemical formula 155]

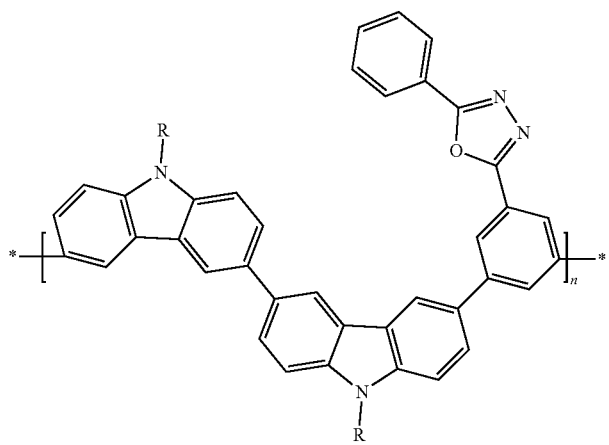
(e137)

[Chemical formula 156]

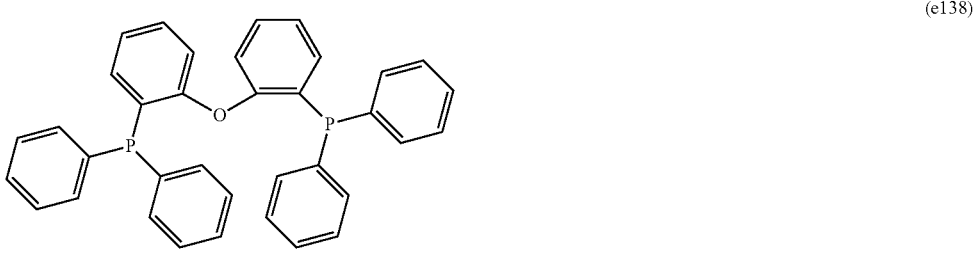
(e138)

[Chemical formula 157]

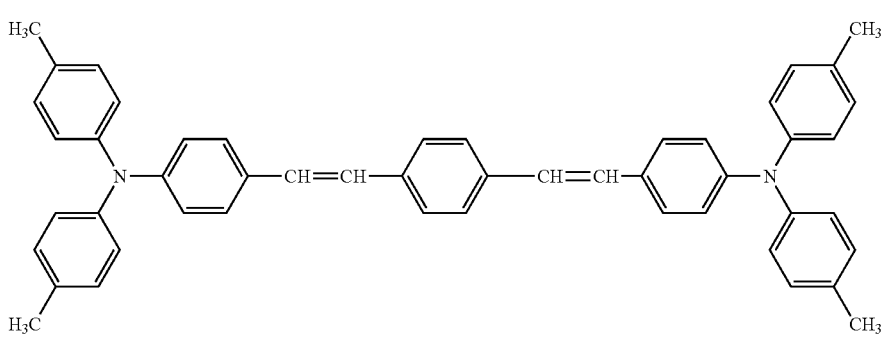
(e139)

[Chemical formula 158]

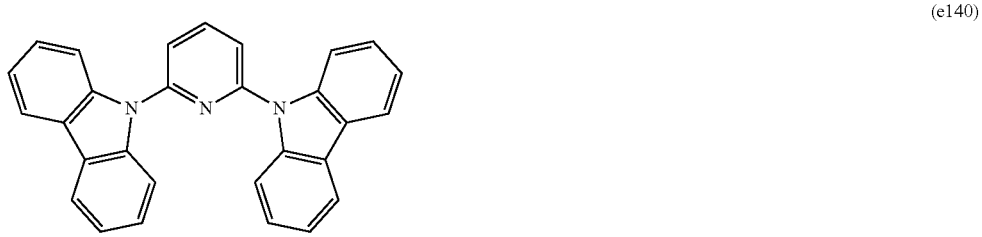
(e140)

Examples of the hole blocking layer provided as necessary include a compound having a hole blocking action, for example, a compound having a bipyridyl group and an orthoterphenyl structure, a phenanthroline derivative such as a bathocuproin (hereinafter abbreviated as BCP), a metal complex of a quinolinol derivative such as an aluminum (III) bis(2-methyl-8-quinolinato)-4-phenylphenolate (hereinafter abbreviated to BAlq), various rare earth complexes, an oxazole derivative, a triazole derivative, a triazine derivative, and the like. These materials may also serve as the material of the electron transport layer. These can be used alone or in combination of two or more. The hole blocking layer may be a film of a single layer structure or a film of a laminated structure. In addition to the vapor deposition method, these materials can be formed into thin films by a known method such as a spin coating method or an ink jet method.

Compounds (hs1) to (hs11) which can be preferably used as a hole blocking material are listed below.
[Chemical formula 159]
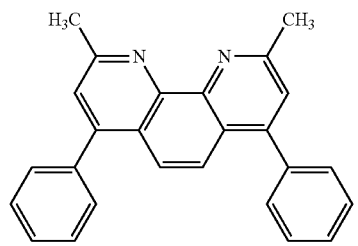
(hs1)
[Chemical formula 160]
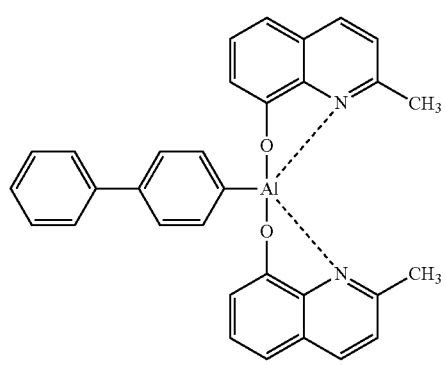
(hs2)
[Chemical formula 161]
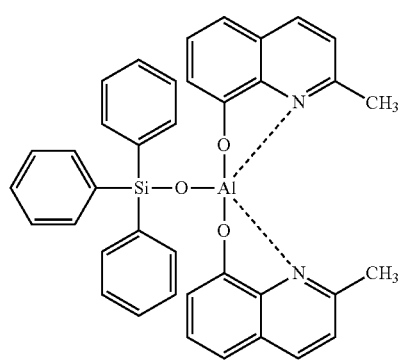
(hs3)
[Chemical formula 162]
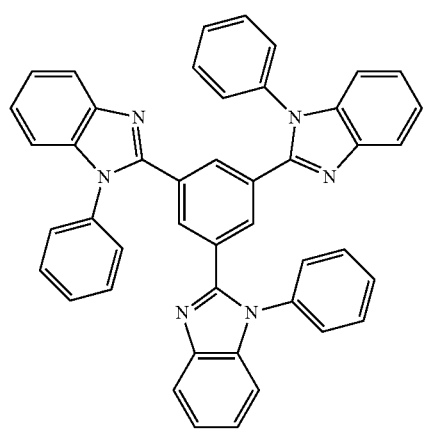
(hs4)
[Chemical formula 163]
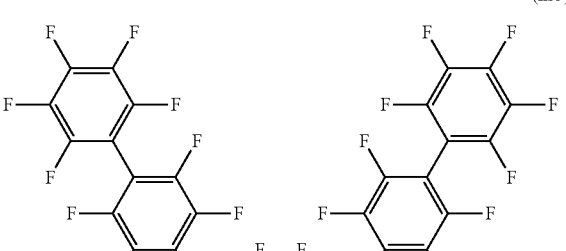
(hs5)
[Chemical formula 164]
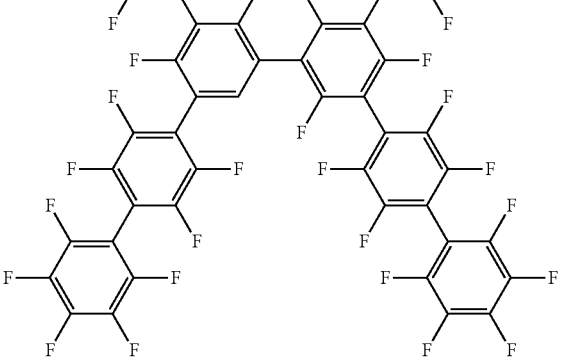
(hs6)
[Chemical formula 165]
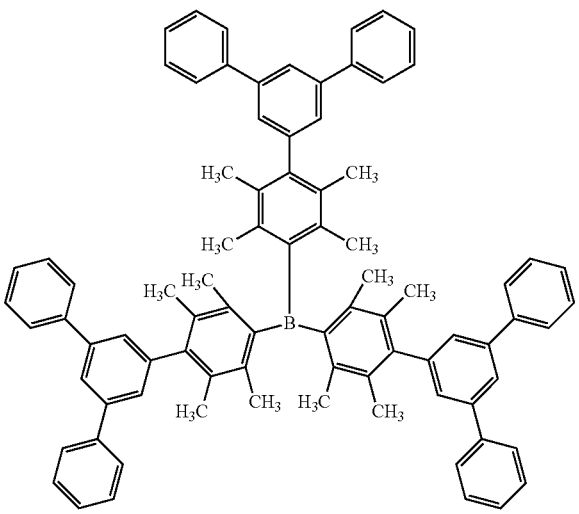
(hs7)
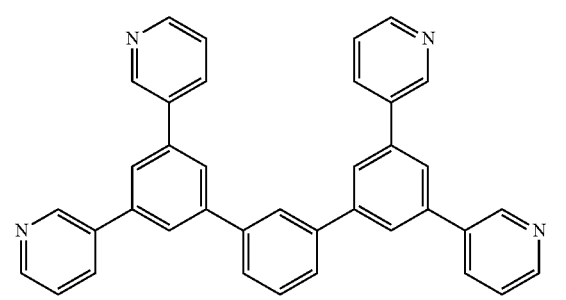

[Chemical formula 166]

(hs8)

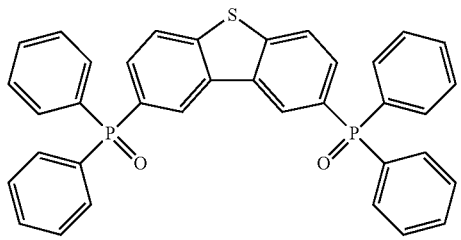

[Chemical formula 167]

(hs9)

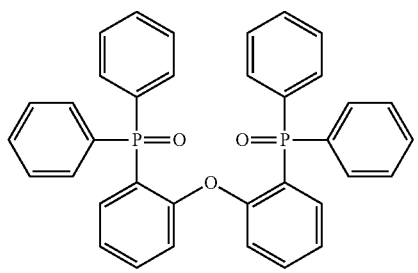

[Chemical formula 168]

(hs10)

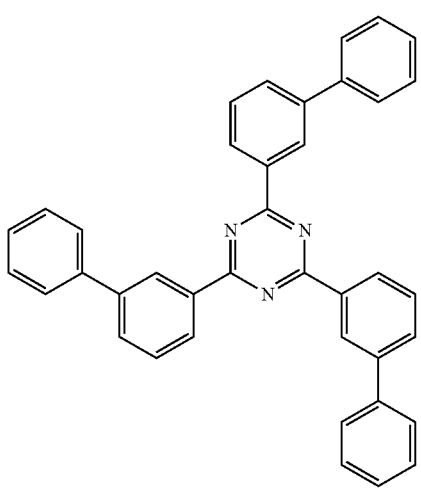

[Chemical formula 169]

(hs11)

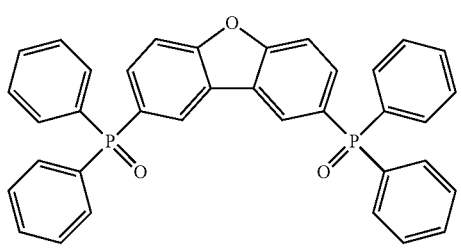

As the electron transport layer provided as necessary, various metal complexes, triazole derivatives, triazine derivatives, oxadiazole derivatives, thiadiazole derivatives, carbodiimide derivatives, quinoxaline derivatives, phenanthroline derivatives, silole derivatives and the like can be used, in addition to metal complexes of quinolinol derivatives such as Alq3 and Balq. These can be used alone or in combination of two or more. The electron transport layer may be a film of a single layer structure or a film of a laminated structure. In addition to the vapor deposition method, these materials can be formed into thin films by a known method such as a spin coating method or an ink jet method.

As the electron injection layer provided as necessary, although an alkali metal salt such as lithium fluoride, cesium fluoride or the like, an alkaline earth metal salt such as magnesium fluoride or the like, a metal oxide such as aluminum oxide or the like can be used, it is preferably to be omitted in the electron transport layer and the cathode.

In the electron injection layer or the electron transport layer, an N-doped metal such as N-doped cesium or the like may be used, in addition to the material ordinarily used for the above described layers.

Compounds (et1) to (et30) that can be preferably used as the electron transport materials are listed below.

[Chemical formula 170]

(et1)

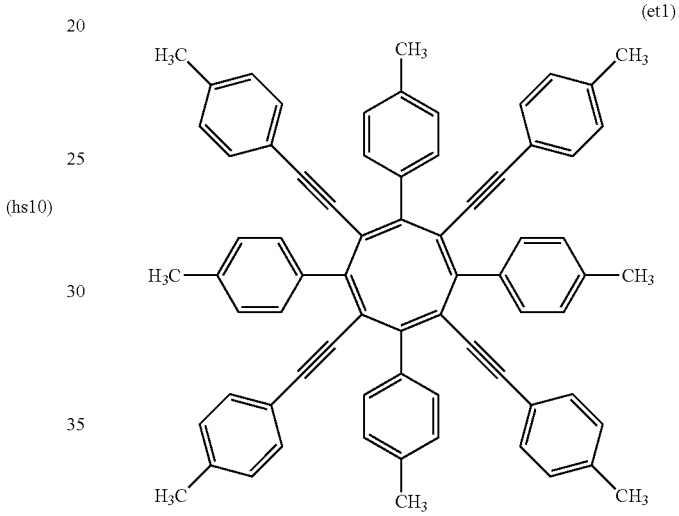

[Chemical formula 171]

(et2)

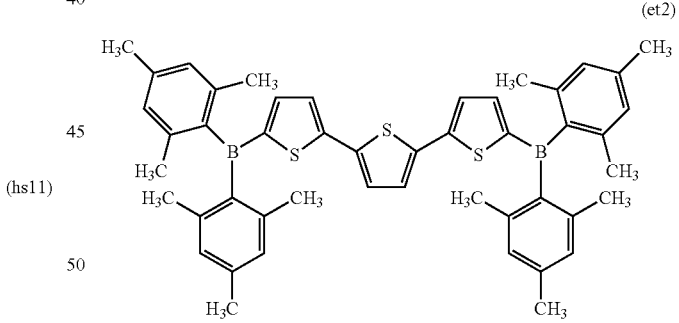

[Chemical formula 172]

(et3)

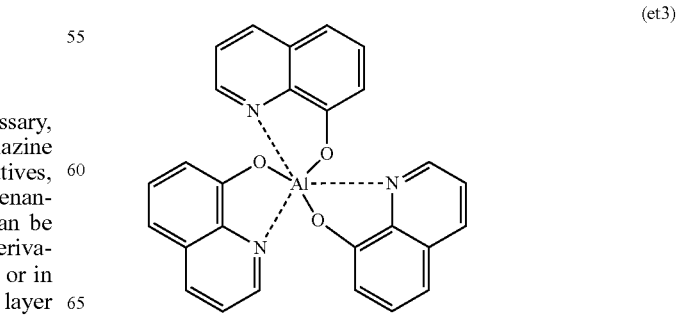

[Chemical formula 173]
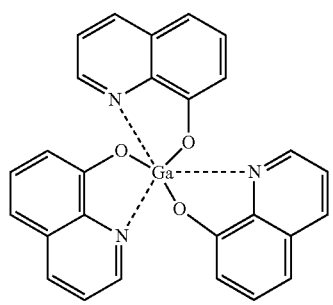
(et4)
[Chemical formula 174]
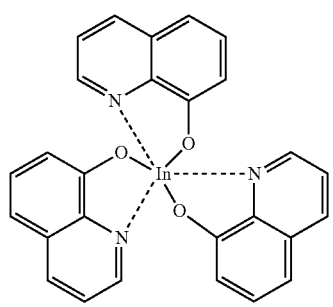
(et5)
[Chemical formula 175]
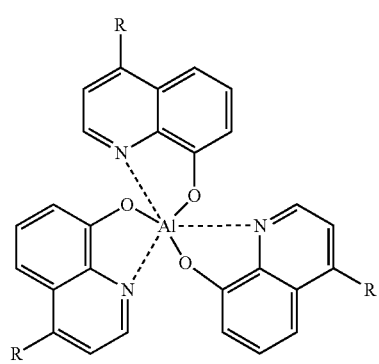
[Chemical formula 176]
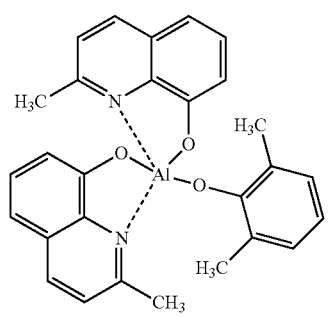
(et7)
[Chemical formula 177]
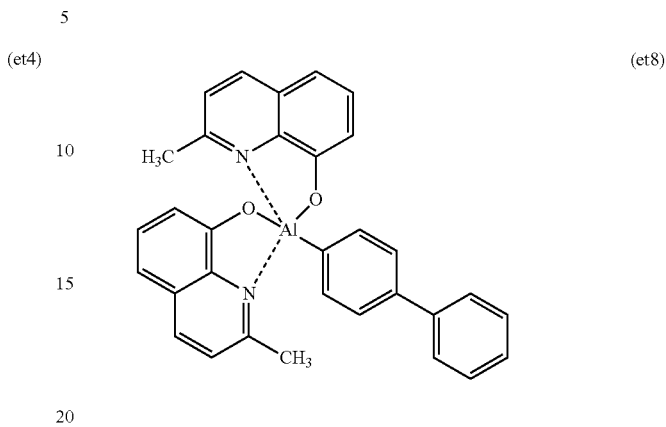
(et8)
[Chemical formula 178]
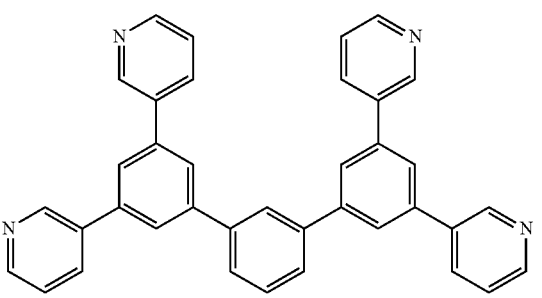
(et9)
[Chemical formula 179]
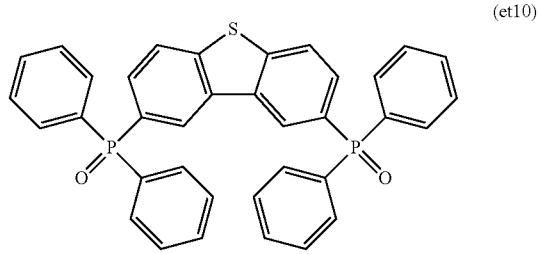
(et10)
[Chemical formula 180]
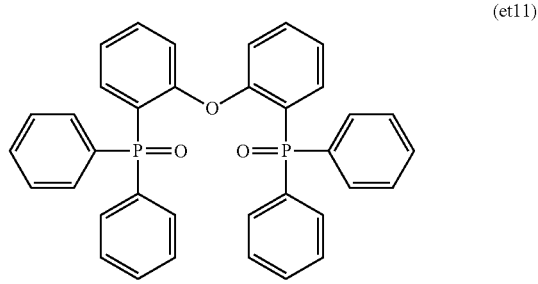
(et11)

[Chemical formula 181]
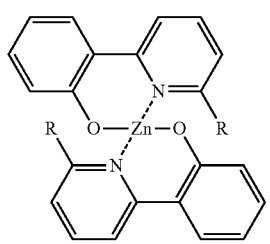
R = *—H
*—O—C(=O)—CH₃ (as drawn)
*—NH—C(=O)—CH₃ (as drawn)
*—CN
(et12)
[Chemical formula 182]
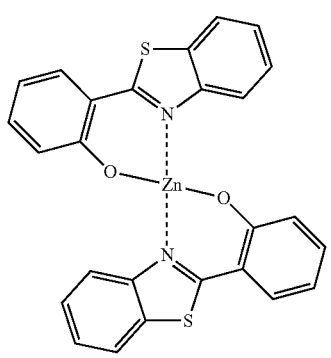
(et13)
[Chemical formula 183]
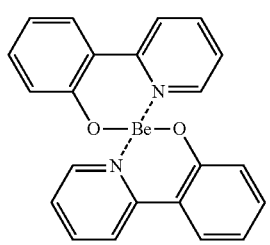
(et14)
[Chemical formula 184]
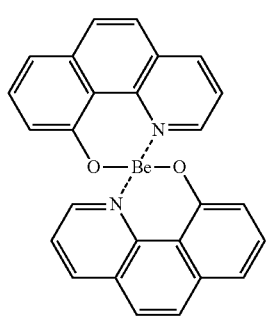
(et15)
[Chemical formula 185]
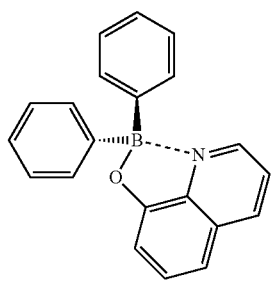
(et16)
[Chemical formula 186]
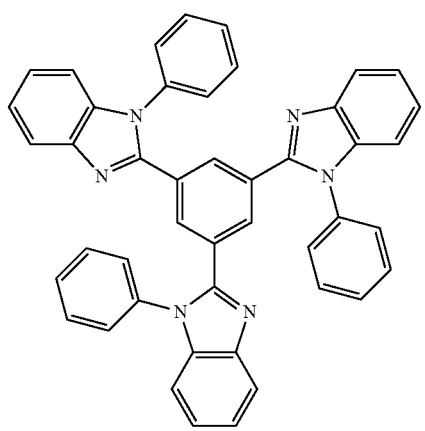
(et17)
[Chemical formula 187]
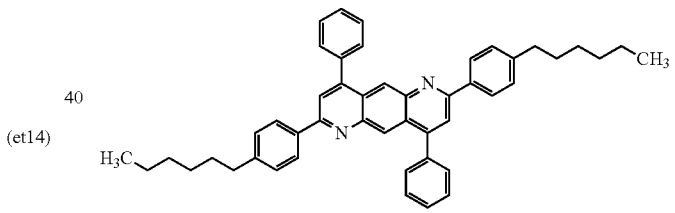
(et18)
[Chemical formula 188]
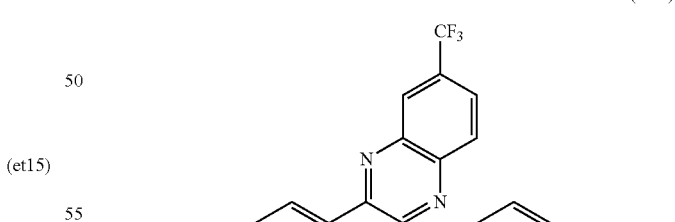
(et19)

[Chemical formula 189]
(et20)
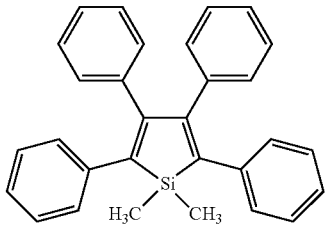
[Chemical formula 190]
(et21)
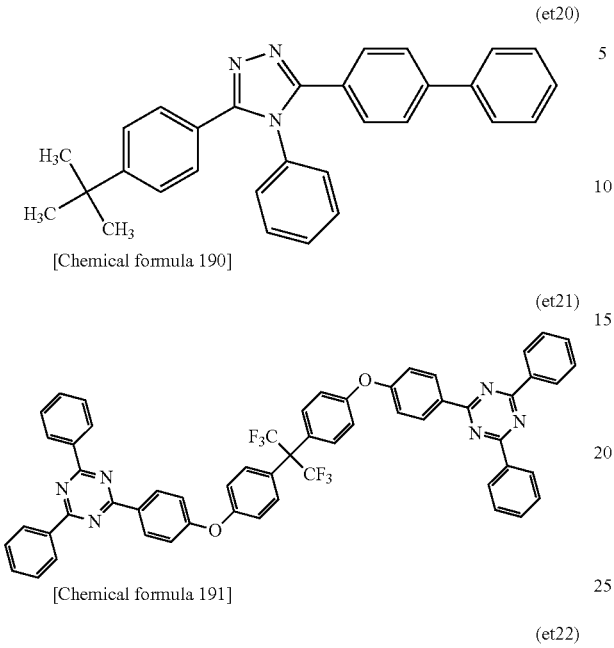
[Chemical formula 191]
(et22)
[Chemical formula 192]
(et23)
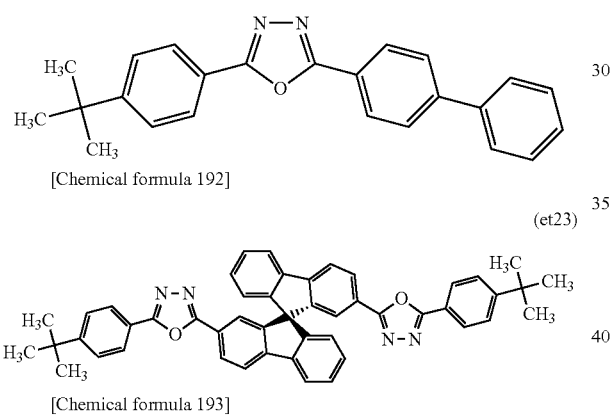
[Chemical formula 193]
(et24)
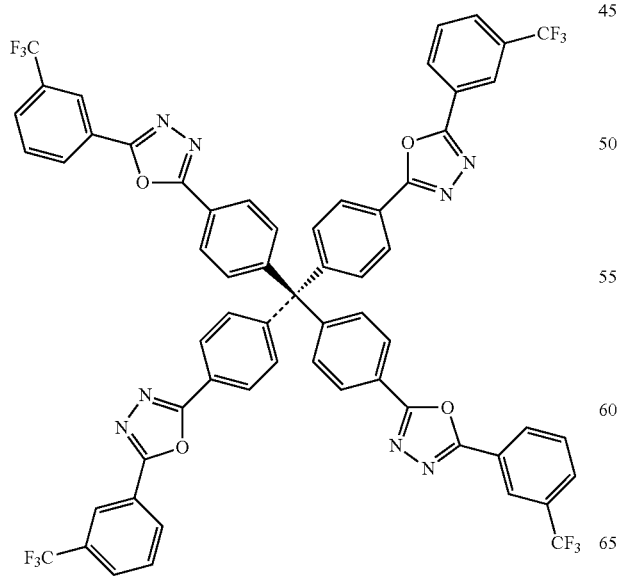
[Chemical formula 194]
(et25)
[Chemical formula 195]
(et26)
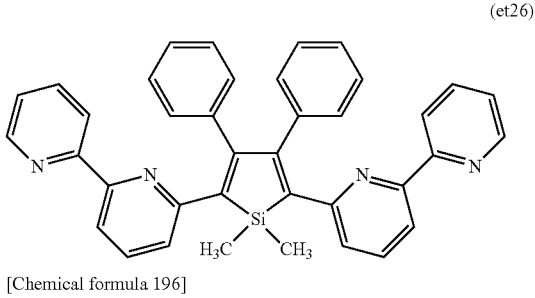
[Chemical formula 196]
(et27)
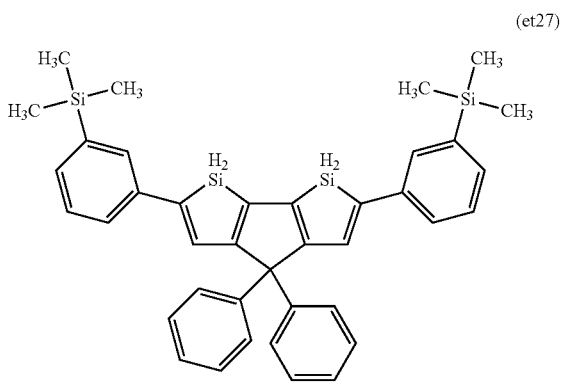
[Chemical formula 197]
(et28)
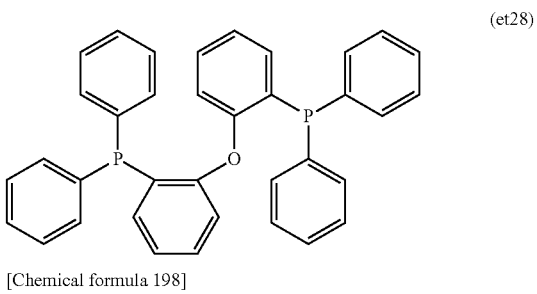
[Chemical formula 198]
(et29)
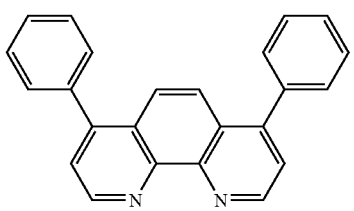

[Chemical formula 199]

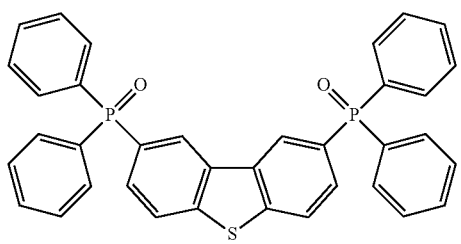
(et30)

Compounds (ei1) to (ei4) which can be preferably used as the electron injecting material are listed below.

[Chemical formula 200]

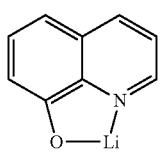
(ei1)

[Chemical formula 201]

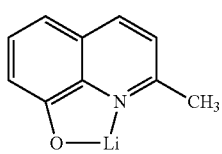
(ei2)

[Chemical formula 202]

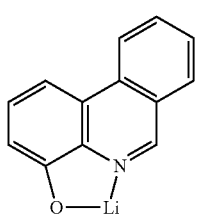
(ei3)

[Chemical formula 203]

(ei4)

Compounds (st1) to (st5) which can be preferably used as the stabilizing material are listed below

[Chemical formula 204]

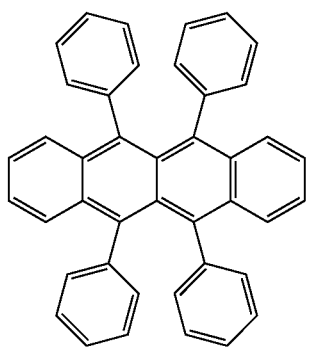
(st1)

[Chemical formula 205]

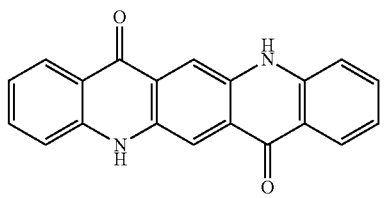
(st2)

[Chemical formula 206]

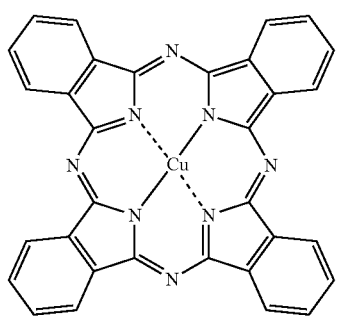
(st3)

[Chemical formula 207]

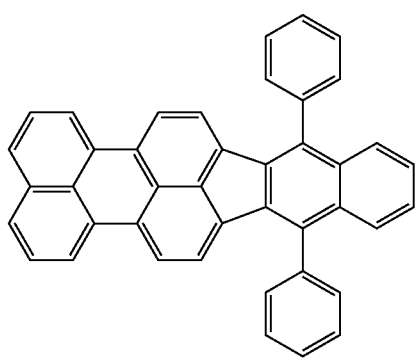
(st4)

[Chemical formula 208]

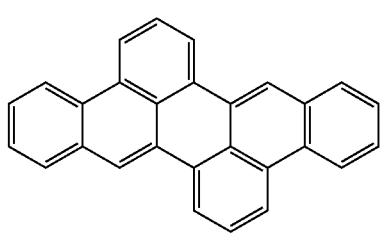
(st5)

For the cathode, a material with a small work function is generally used. For example, sodium, sodium-potassium alloy, lithium, tin, magnesium, magnesium/copper mixture, magnesium/aluminum mixture, magnesium/indium mixture, aluminum/aluminum oxide mixture, indium, calcium, aluminum, silver, lithium/aluminum mixture, magnesium silver alloy, magnesium indium alloy, aluminum magnesium alloy and the like can be used. By using a transparent conductive material, it is possible to obtain a transparent or translucent cathode. The thickness of the cathode is usually 10 to 5000 nm, preferably 50 to 200 nm. The sheet resistance of the cathode is preferably several hundred Ω/□ or more.

When a metal layer having a high work function and stable to the atmosphere, such as aluminum, silver, nickel, chromium, gold, platinum or the like, is further laminated thereon for the propose of protecting the cathode made of a low work function metal, the stability of the device increases and thus it is preferable. Further, in order to improve contact between the cathode and an adjacent organic layer (for example, an electron transport layer or an electron injection layer), a cathode interface layer may be provided between the cathode and the organic layer. As a material used for the cathode interface layer, an aromatic diamine compound, a quinacridone compound, a naphthacene derivative, an organosilicon compound, an organophosphorus compound, a compound having an N-phenylcarbazole skeleton, an N-vinylcarbazole polymer and the like can be exemplified.

The luminescence device of the present invention can be applied to either a single device, a device having a structure arranged in an array, or a structure in which an anode and a cathode are arranged in X-Y matrix form.

The effect of the embodiment of the present invention will be described below.

Organic photoluminescence devices and organic electroluminescence devices were fabricated using the luminescent materials of the present invention, and light emission characteristics were evaluated.

Evaluation of the luminescent materials was performed using a source meter (manufactured by Keithley Instruments Inc., 2400 series), a semiconductor parameter analyzer manufactured by Agilent Technologies, E5273 A), an optical power meter measuring apparatus (manufactured by Newport KK, 1930C), an optical spectrometer (manufactured by Ocean Optics Co., Ltd., USB 2000), a spectroradiometer (manufactured by TOPCON CORPORATION, SR-3), and a streak camera (manufactured by Hamamatsu Photonics KK, 04334 model).

Next, the present invention will be described in more detail by showing examples. The present invention is not limited by these examples. Additions, omissions, substitutions, and other changes in the configuration are possible within a range not exceeding the significance of the present invention.

EXAMPLE 1

A toluene solution A (concentration: $10^{-4}$ mol/l) of Ac-CNP was prepared in a glove box under an argon atmosphere.

An organic photoluminescence device B including a thin film having a thickness of 100 nm was obtained by depositing on a quartz substrate using Ac-CNP as a vapor deposition source under a condition of vacuum degree of $10^{-4}$ Pa or less.

An organic photoluminescence device C including a thin film having Ac-CNP concentration of 6.0 wt % and a thickness of 100 nm was obtained by depositing on a quartz substrate using Ac-CNP and mCBP respectively as a vapor deposition source under a condition of $10^{-4}$ Pa or less.

For the toluene solution A, the organic photoluminescence device B and the organic photoluminescence device C, the emission spectrum and the absorption spectrum with 310 nm excitation light were measured. The results are shown in FIG. 1.

The photoluminescence quantum efficiency was 20.4% in the toluene solution A with nitrogen bubbling, 9.3% in the toluene solution A without nitrogen bubbling, and 67.4% in the organic photoluminescence device C.

Figure 2:
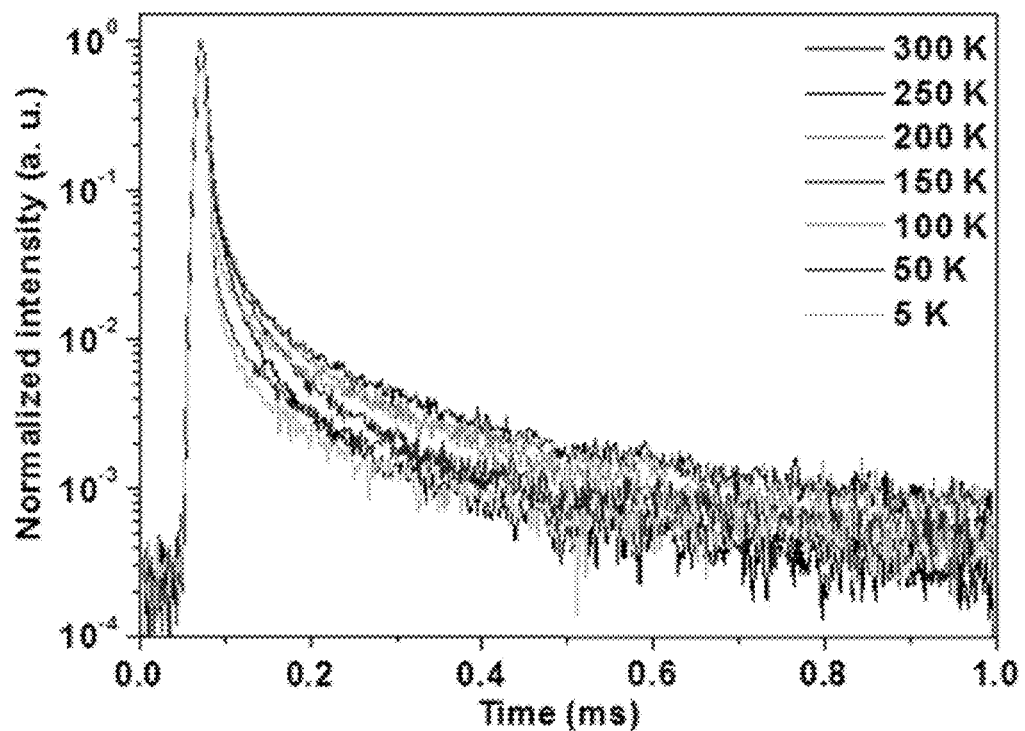
FIG. 2 shows a transient decay curve of Ac-CNP organic photoluminescence device C.

Transient decay curves of the organic photoluminescence device C at 5 K, 50 K, 100 K, 150 K, 200 K, 250 K, and 300 K are shown in FIG. 2. In this transient decay curve, a linear component (fluorescence component) is observed at the beginning, but a component (delay component) deviating from linearity is observed after several μ seconds. From this result, it can be seen that Ac-CNP is a luminescent body ($\tau_{prompt}$=45 nanoseconds, $\tau_{delayed}$=71 microseconds) including a delay component in addition to the fluorescence component. In addition, it can be seen that Ac-CNP is a thermally activated delayed fluorescent material (TADF) because there is a change in the lifetime of the delay component depending on the temperature.

Figure 3:
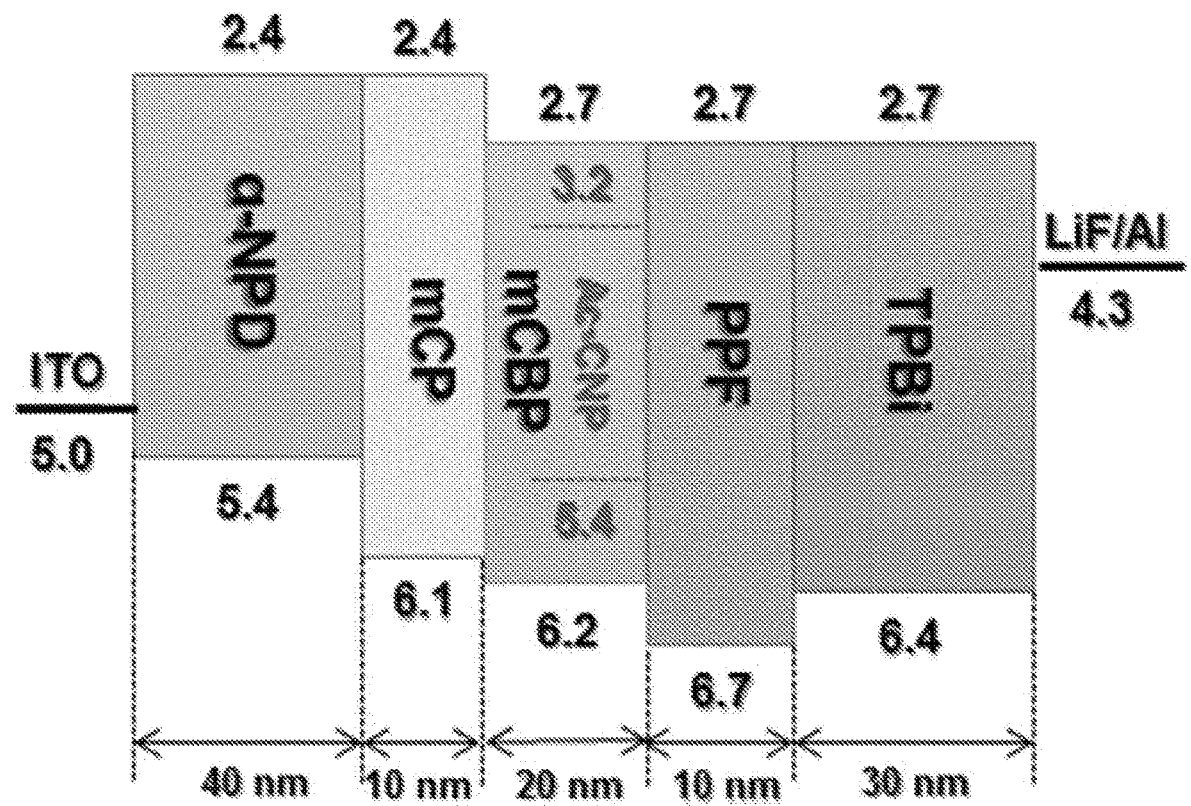
FIG. 3 shows a film configuration of Ac-CNP organic electroluminescence device.

On a glass substrate on which an anode made of indium-tin oxide (ITO) and having a film thickness of 110 nm was formed, a hole transport layer with a thickness of 40 nm, an electron blocking layer with a thickness of 10 nm, a luminescent layer with a thickness of 20 nm, a hole blocking layer with a thickness of 10 nm and an electron transport layer with a thickness of 30 nm were laminated in this order by a vacuum vapor deposition method ($5.0 \times 10^{-4}$ Pa or less) (see FIG. 3).

α-NPD was used as the material of the hole transport layer.

[Chemical formula 209]

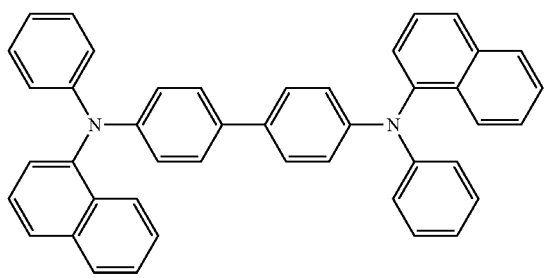

(α-NPD)

mCP was used as the material of the electron blocking layer.

[Chemical formula 210]

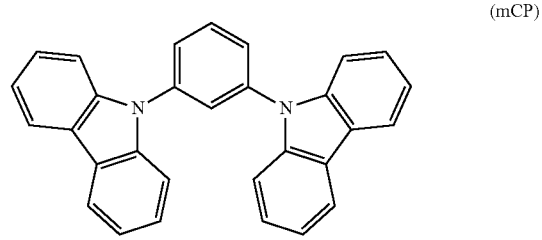

(mCP)

mCBP was used as the host material of the luminescent layer.

[Chemical formula 211]

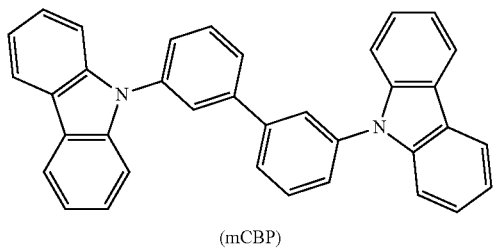

(mCBP)

Ac-CNP was used as the doping material for the luminescent layer. Ac-CNP concentration was set to 6.0% by weight.

[Chemical formula 212]

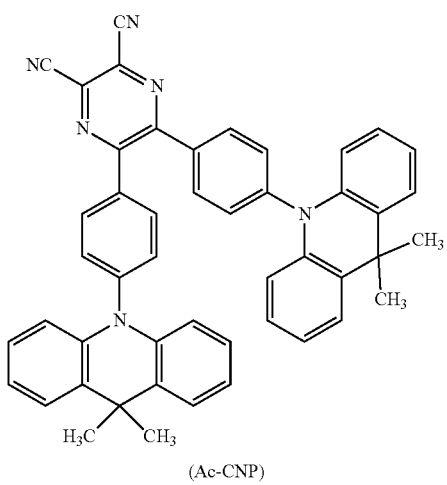

(Ac-CNP)

PPF was used as the material of the hole blocking layer.

[Chemical formula 213]

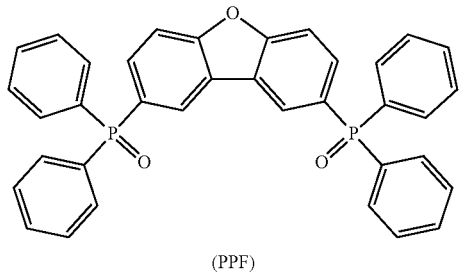

(PPF)

TPBi was used as the material for the electron transport layer.

[Chemical formula 214]

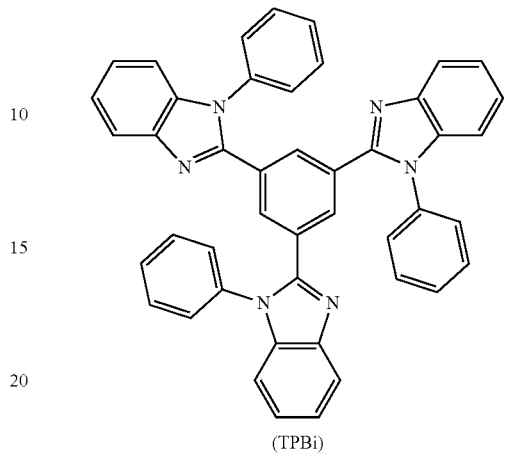

(TPBi)

Subsequently, a lithium fluoride film having a thickness of 0.8 nm and an aluminum film having a thickness of 80 nm were laminated in this order by a vacuum vapor deposition method to form a cathode, thereby obtaining an organic electroluminescence device.

Figure 4:
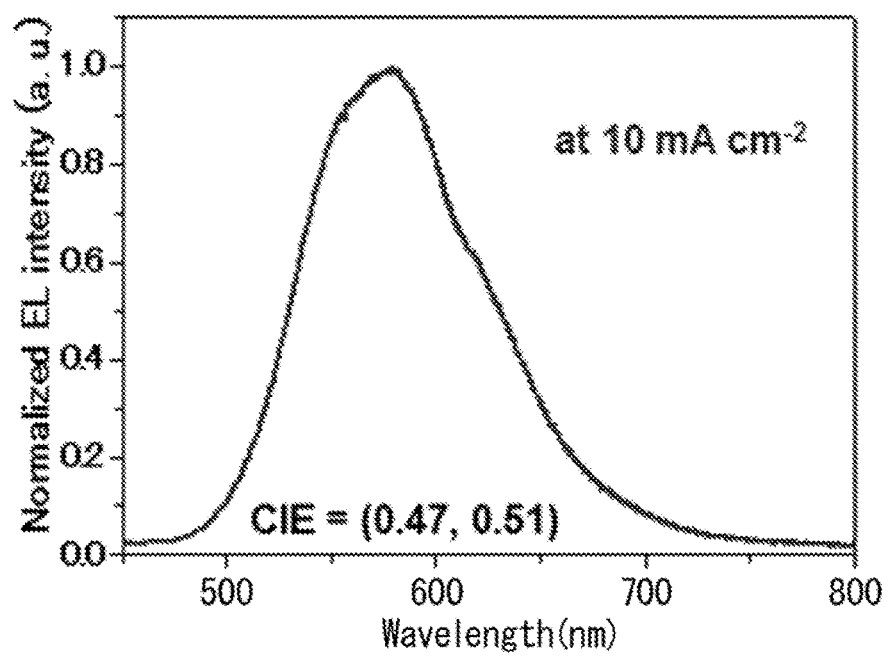
FIG. 4 shows a light emission spectrum of Ac-CNP organic electroluminescence device.
Figure 5:
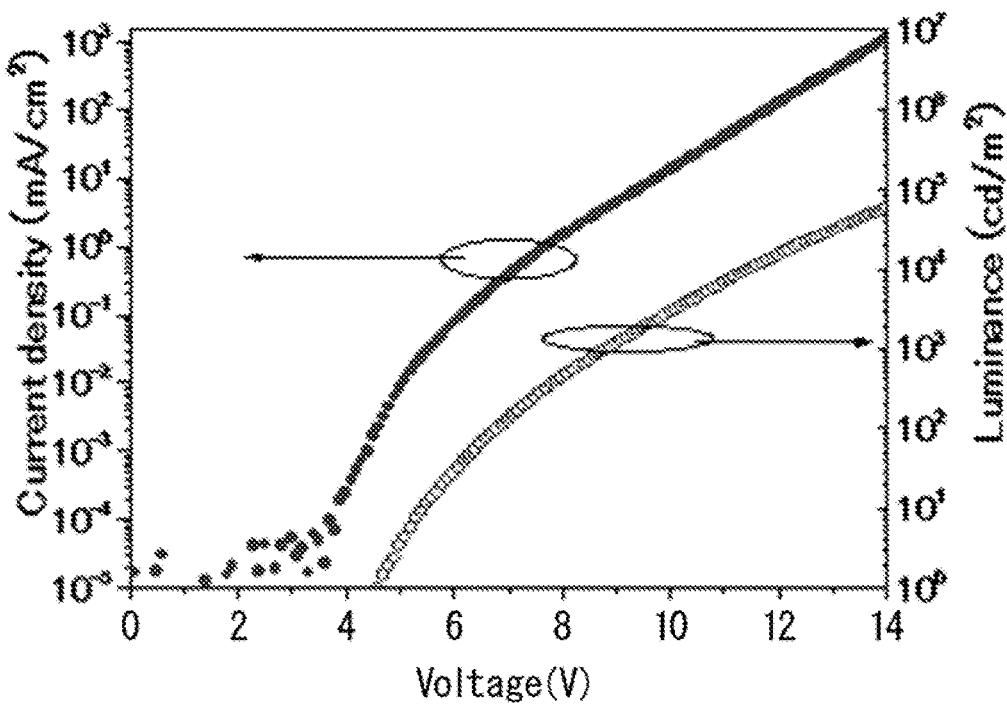
FIG. 5 shows a voltage-current density-light emission intensity characteristic of Ac-CNP organic electroluminescence device.
Figure 6:
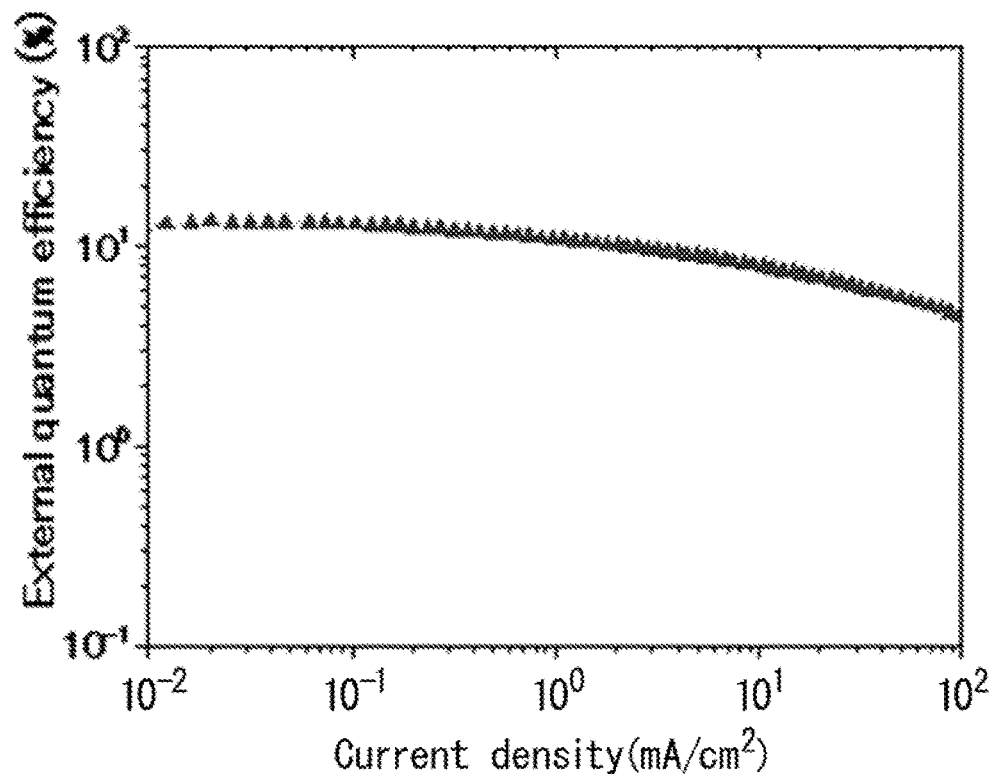
FIG. 6 shows a current density-external quantum efficiency characteristic of Ac-CNP organic electroluminescence device.

The characteristics of the organic electroluminescence device were measured. FIG. 4 shows the emission spectrum. The emission spectrum was in a range of about 500 nm to about 700 nm. FIG. 5 shows voltage-current density-emission intensity characteristics. The data indicated by the leftward arrow indicates the voltage-current density characteristic, and the data indicated by the rightward arrow indicates the voltage-emission intensity characteristic. FIG. 6 shows the current density-external quantum efficiency characteristic. The maximum external quantum efficiency was 13.3%. Since the theoretical limit value of the external quantum efficiency of an organic electroluminescence device using a fluorescent material is 5 to 7.5%, the organic electroluminescence device of the present invention obtained by using Ac-CNP realizes a high external quantum efficiency exceeding the theoretical limit.

EXAMPLE 2

Figure 7:
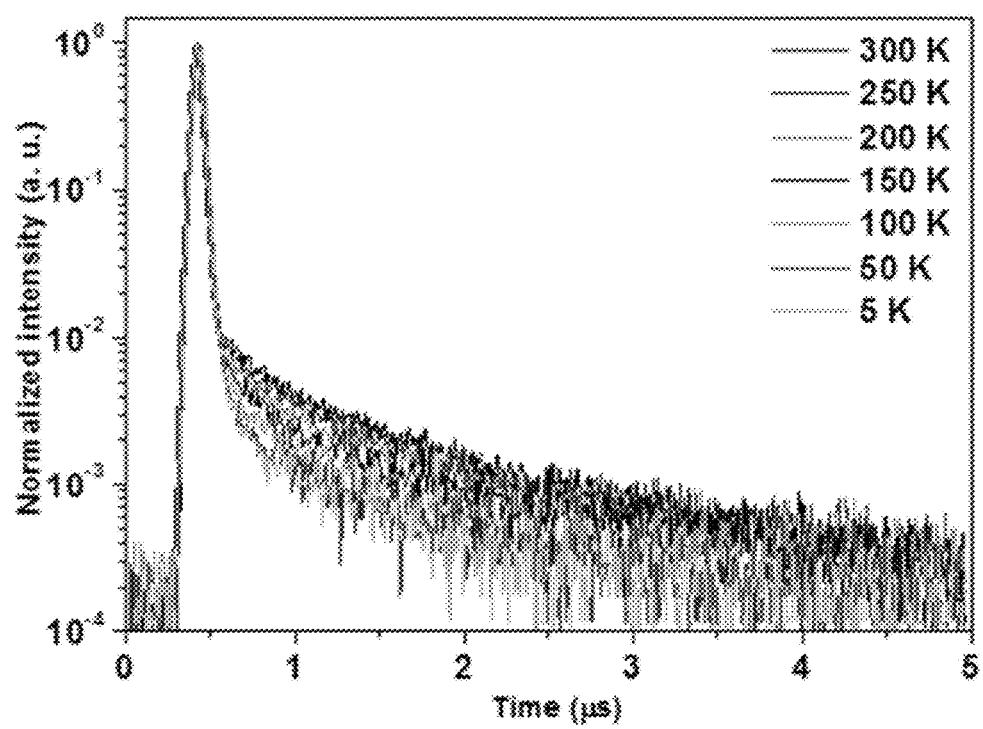
FIG. 7 shows a transient decay curve of Px-CNP organic photoluminescence device C.

The characteristics were evaluated in the same manner as in Example 1 except that Px-CNP was used instead of Ac-CNP. In the toluene solution, light emission in the visible region could not be observed. The photoluminescence quantum efficiency was 15.1% in the organic photoluminescence device C. From the transient decay curve, it can be seen that Px-CNP is a luminescent body ($\tau_{prompt}$=21 nanoseconds, $\tau_{delayed}$=1.5 microseconds) including a delay component in addition to the fluorescence component (see FIG. 7). Also, since there is a change in the lifetime of the delay component depending on the temperature, it can be seen that Px-CNP is a thermally activated delayed fluorescent material (TADF).

Figure 8:
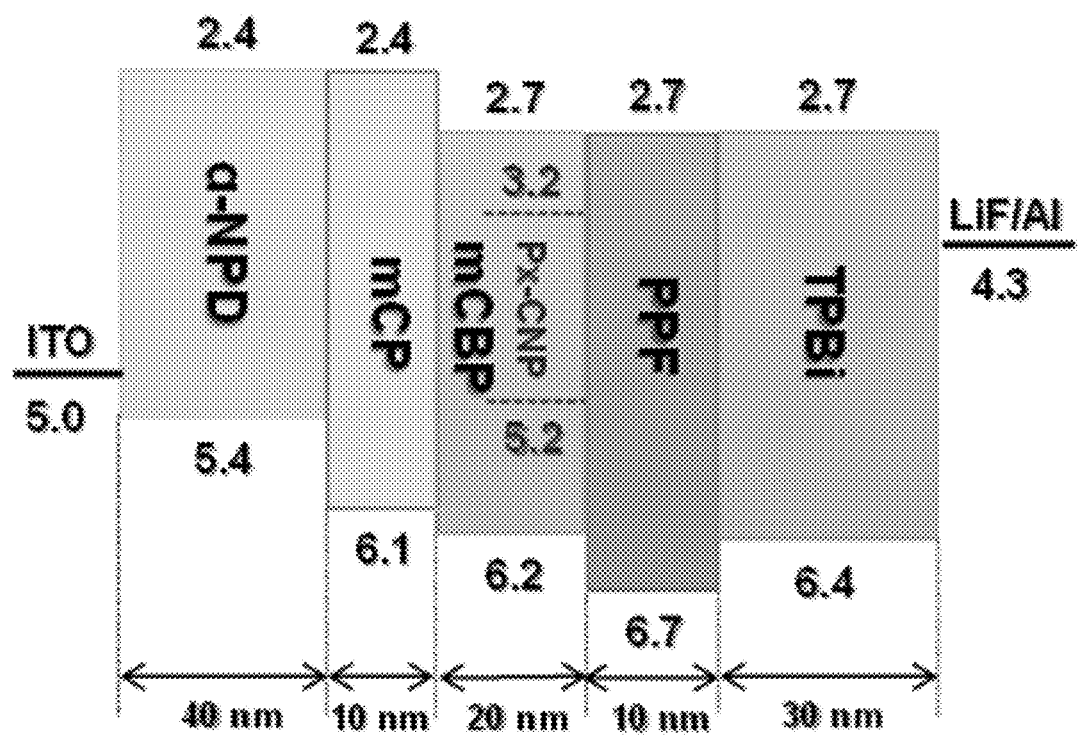
FIG. 8 shows a film configuration of Px-CNP organic electroluminescence device.
Figure 9:
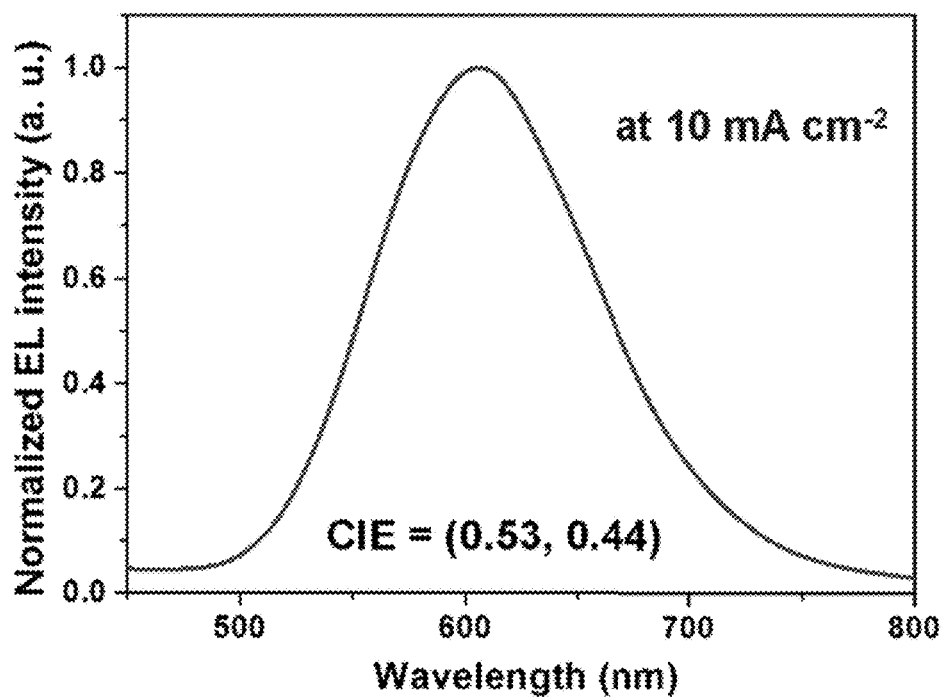
FIG. 9 shows a light emission spectrum of Px-CNP organic electroluminescence device.
Figure 10:
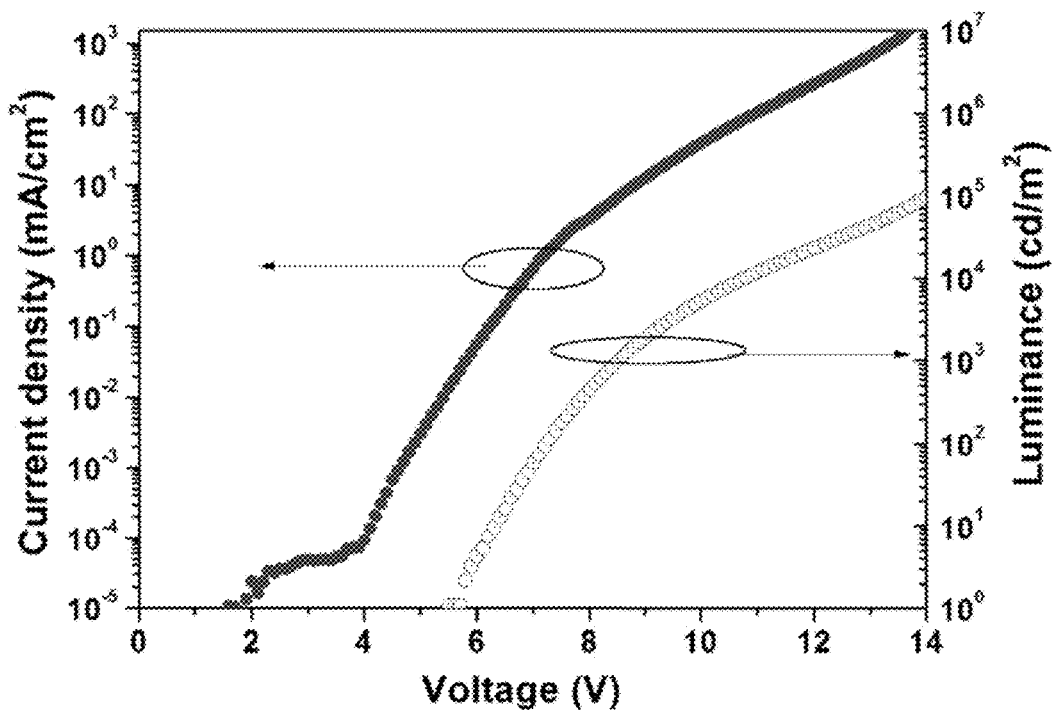
FIG. 10 shows a voltage-current density-emission intensity characteristic of Px-CNP organic electroluminescence device.
Figure 11:
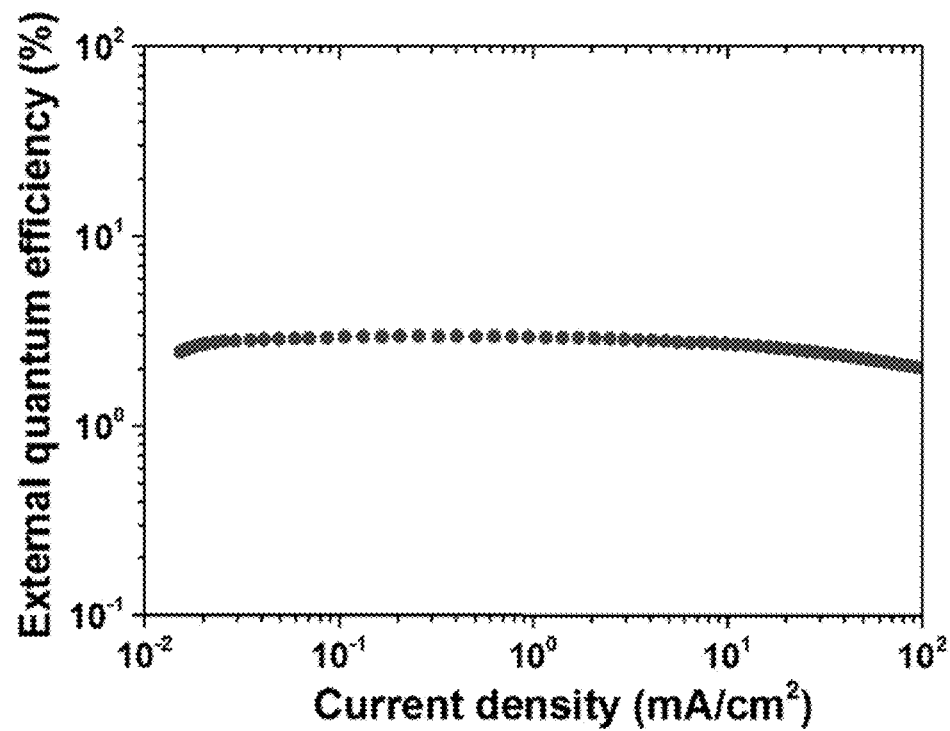
FIG. 11 shows a current density-external quantum efficiency characteristic of Px-CNP organic electroluminescence device.

The characteristics of the organic electroluminescence device (FIG. 8) were measured. FIG. 9 shows the emission spectrum. As in Example 1, the emission spectrum was in the range of about 500 nm to about 700 nm. FIG. 10 shows the voltage-current density-emission intensity characteristics. The data indicated by the leftward arrow indicates the voltage-current density characteristic, and the data indicated by the rightward arrow indicates the voltage-emission intensity characteristic. FIG. 11 shows the current density-external quantum efficiency characteristic. The maximum external quantum efficiency was 3.0%.

[Chemical formula 215]

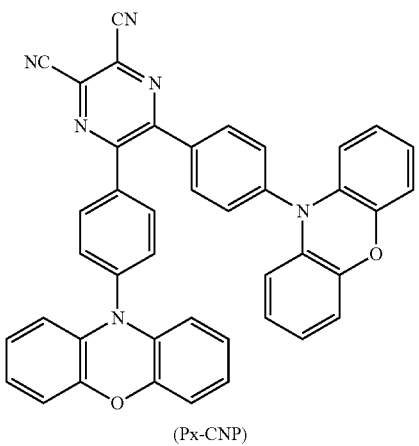

(Px-CNP)

EXAMPLE 3

Figure 12:
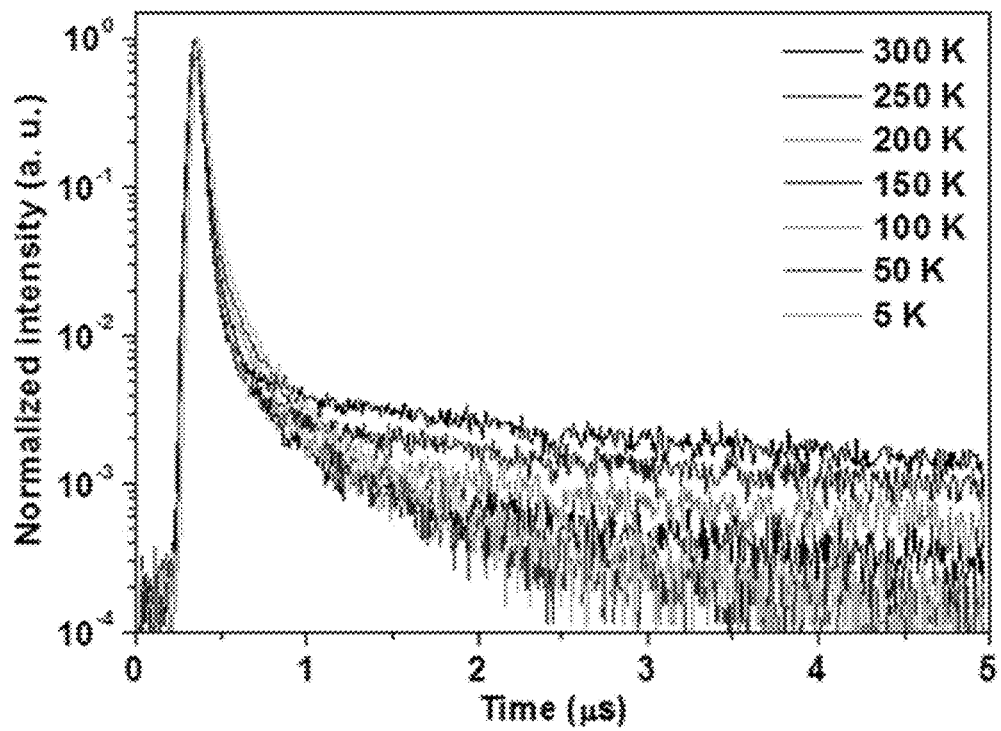
FIG. 12 shows a transient decay curve of BCz-CNP organic photoluminescence device C.

The characteristics were evaluated in the same manner as in Example 1 except that BCz-CNP was used instead of Ac-CNP. The photoluminescence quantum efficiency was 15.6% in the toluene solution A with nitrogen bubbling, 10.8% in the toluene solution A without nitrogen bubbling, and 54.7% in the organic photoluminescence device C. From the transient decay curve, it can be seen that BCz-CNP is a luminescent body ($\tau_{prompt}$=35 nanoseconds, $\tau_{delayed}$=135 microseconds) including a delay component in addition to the fluorescence component (see FIG. 12). In addition, it can be seen that BCz-CNP is a thermally activated delayed fluorescent material (TADF) because there is a change in the lifetime of the delay component depending on the temperature.

Figure 13:
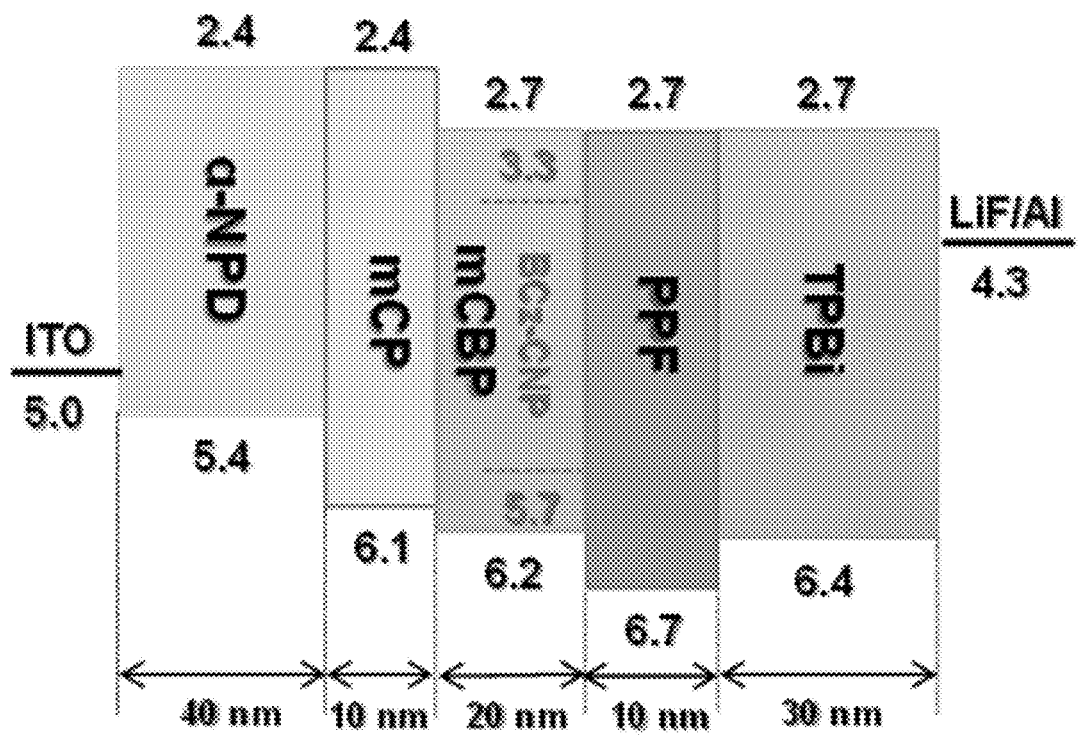
FIG. 13 shows a film configuration of a BCz-CNP organic electroluminescence device.

The characteristics of the organic electroluminescence device (FIG. 13) were measured. As in Example 1, the emission spectrum was in the range of about 500 nm to about 700 nm. The maximum external quantum efficiency was 11.9%.

[Chemical formula 216]

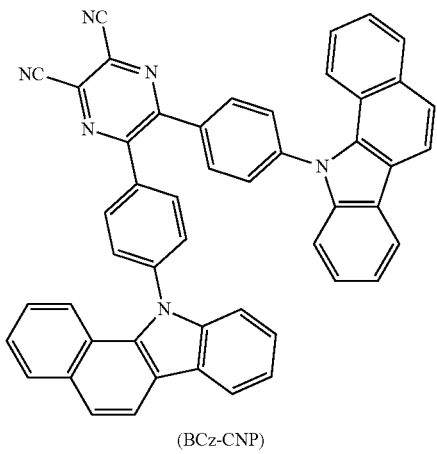

(BCz-CNP)

EXAMPLE 4

An organic photoluminescence device B including a thin film having a thickness of 100 nm was obtained by depos-iting on a quartz substrate under a condition of vacuum degree of $10^{-4}$ Pa or less using PCz-DCP as a vapor deposition source.

An organic photoluminescence device C including a thin film having a PCz-DCP concentration of 6.0% by weight and a thickness of 100 nm was obtained by depositing on a quartz substrate under a condition of $10^{-4}$ Pa or less using PCz-DCP and CBP respectively as a vapor deposition source.

Figure 14:
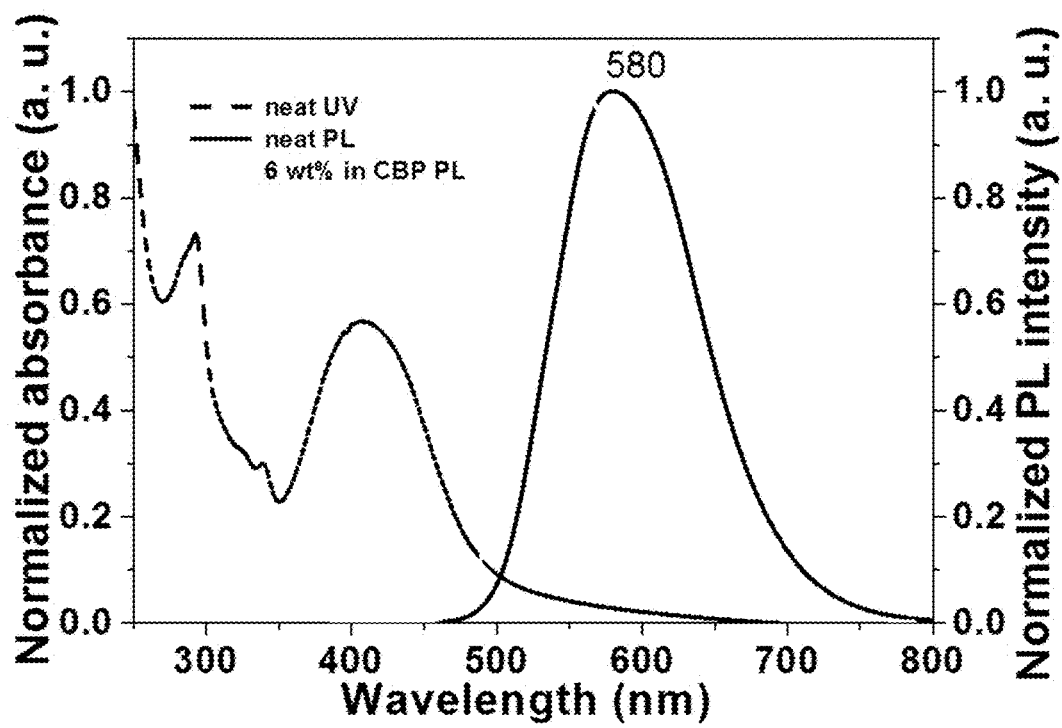
FIG. 14 shows an absorption/emission spectrum of PCz-DCP organic photoluminescence device B and PCz-DCP organic photoluminescence device C.

For the organic photoluminescence device B and the organic photoluminescence device C, emission spectrum and absorption spectrum with 310 nm excitation light were measured. The results are shown in FIG. 14.

The photoluminescence quantum efficiency was 36.5% in the organic photoluminescence device C.

Figure 15:
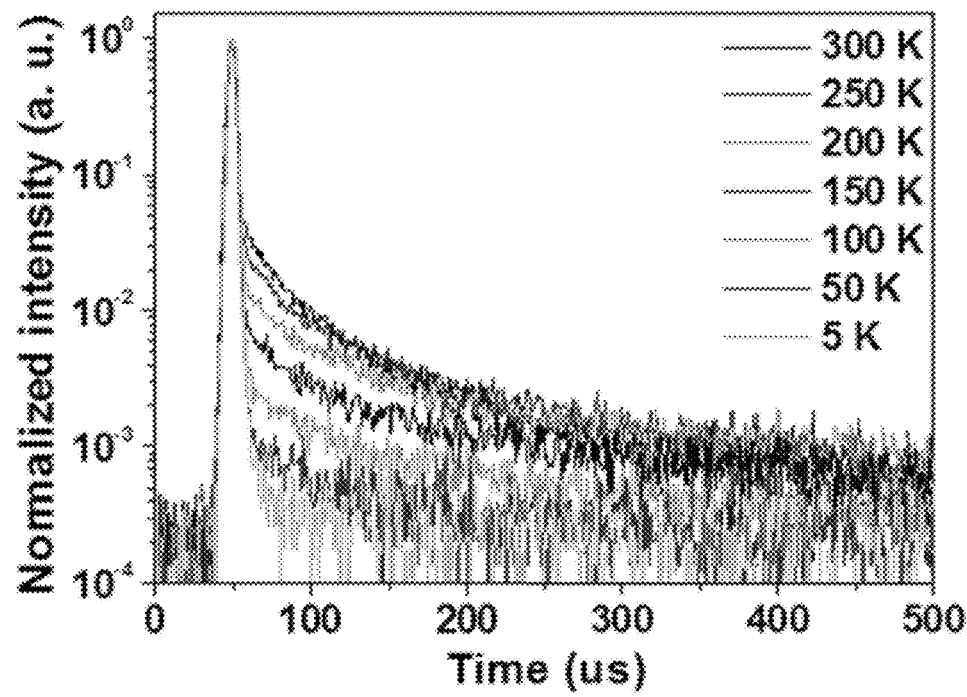
FIG. 15 shows a transient decay curve of PCz-DCP organic photoluminescence device C.

Transient decay curves of organic photoluminescence device C at 5 K, 50 K, 100 K, 150 K, 200 K, 250 K, and 300 K are shown in FIG. 15. In the transient decay curves, a linear component (fluorescence component) is observed at the beginning, but a component (delay component) deviating from linearity is observed after several microseconds. From this result, it can be seen that PCz-DCP is a luminescent body ($\tau_{prompt}$=28 nanoseconds, $\tau_{delayed}$=147 microseconds) containing a delay component in addition to the fluorescence component. Also, since there is a change in the lifetime of the delay component depending on the temperature, it can be seen that PCz-DCP is a thermally activated delayed fluorescent material (TADF).

A 35 nm thick hole transport layer, a 15 nm thick luminescent layer, a 10 nm thick hole blocking layer, and a 40 nm thick electron blocking layer were laminated by a vacuum evaporation method ($5.0 \times 10^{-4}$ Pa or less) in this order on a glass substrate on which an anode made of indium tin oxide (ITO) and having a film thickness of 110 nm was formed.

TAPC was used as the material for the hole transport layer.

[Chemical formula 217]

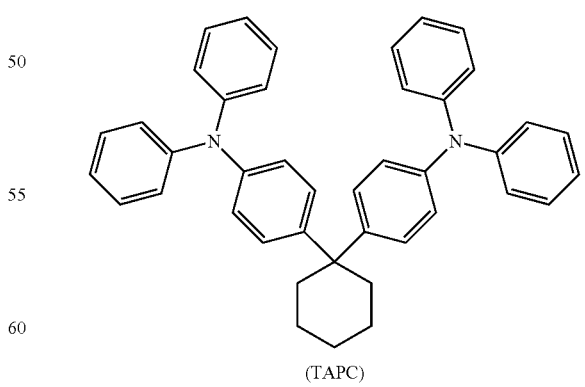

(TAPC)

CBP was used as the host material of the luminescent layer.

[Chemical formula 218]

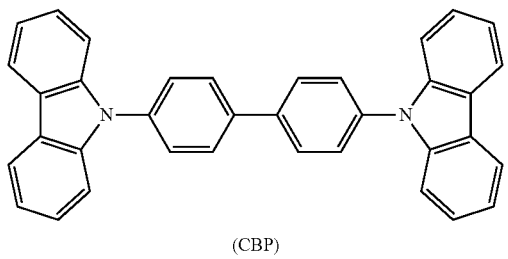

(CBP)

PCz-DCP was used as the doping material for the luminescent layer. The PCz-DCP concentration was set to 6.0 wt %.

[Chemical formula 219]

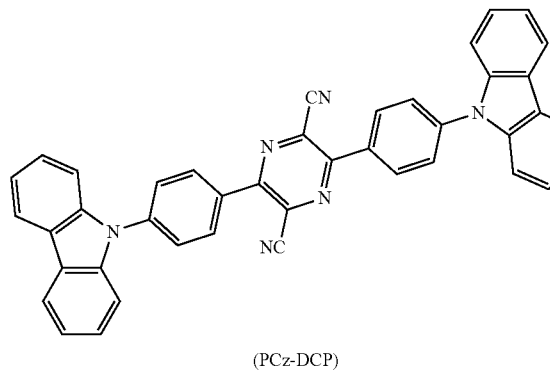

(PCz-DCP)

PPF was used as the material of the hole blocking layer. B3PyPB was used as the material of the electron transport layer.

[Chemical formula 220]

(B3PyPB)

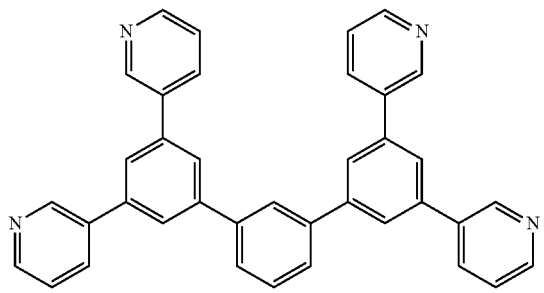

Figure 16:
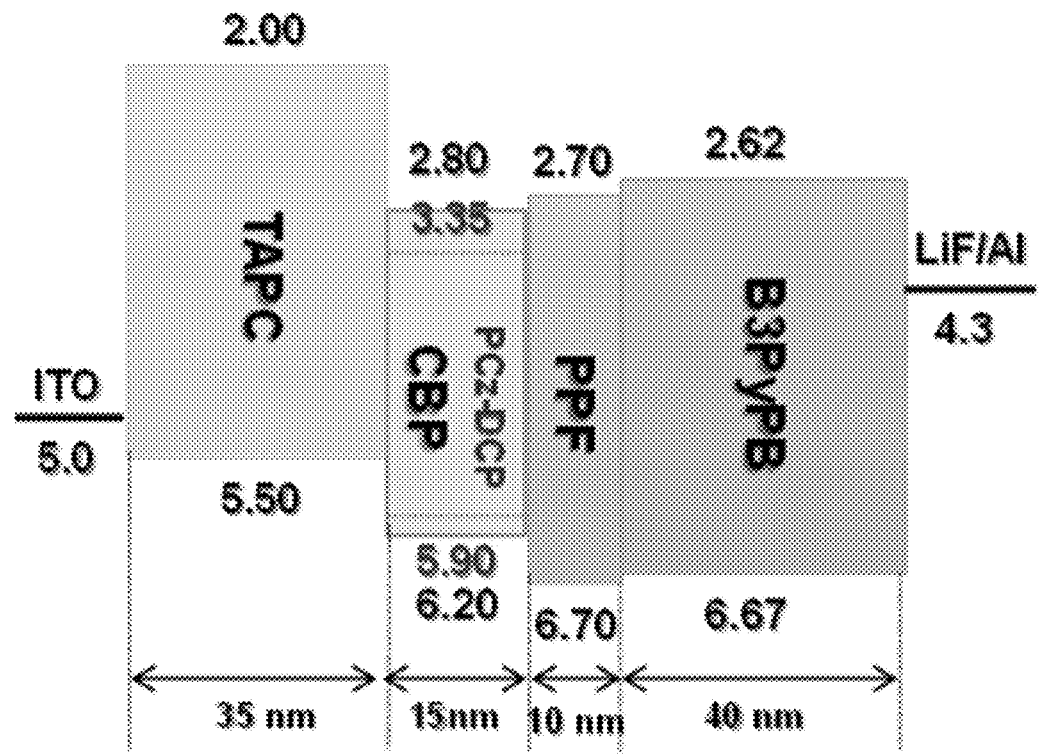
FIG. 16 shows a film configuration of a PCz-DCP organic electroluminescence device (Device B).

Subsequently, a lithium fluoride film having a thickness of 0.8 nm and an aluminum film having a thickness of 80 nm were laminated in this order by a vacuum vapor deposition method to form a cathode, thereby obtaining an organic electroluminescence device (Device B)(see FIG. 16).

Figure 18:
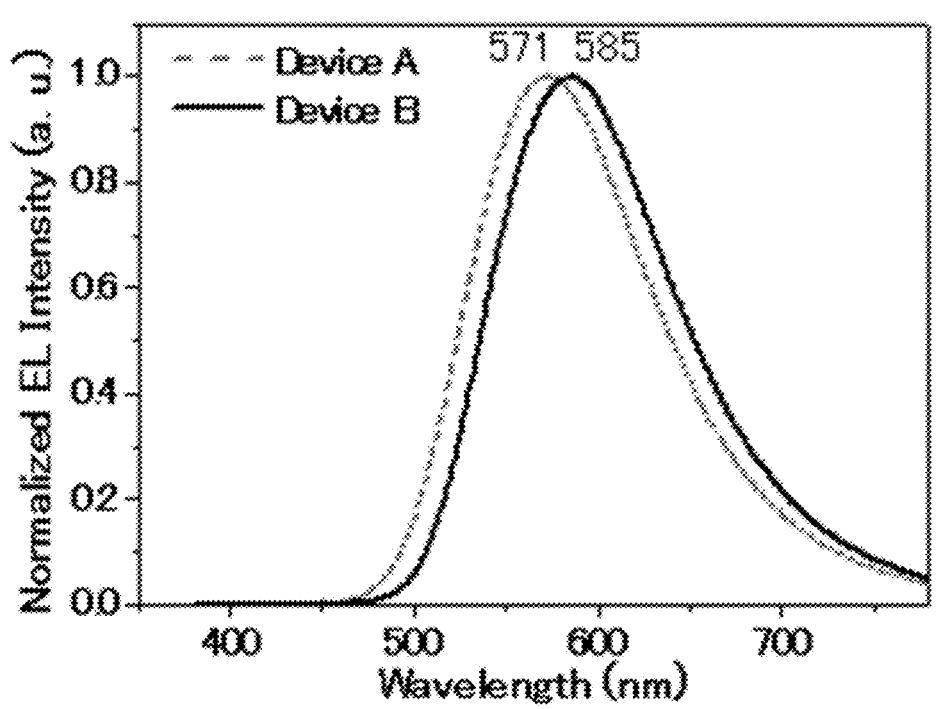
FIG. 18 shows a light emission spectrum of PCz-DCP organic electroluminescence devices (Device B and Device A).
Figure 19:
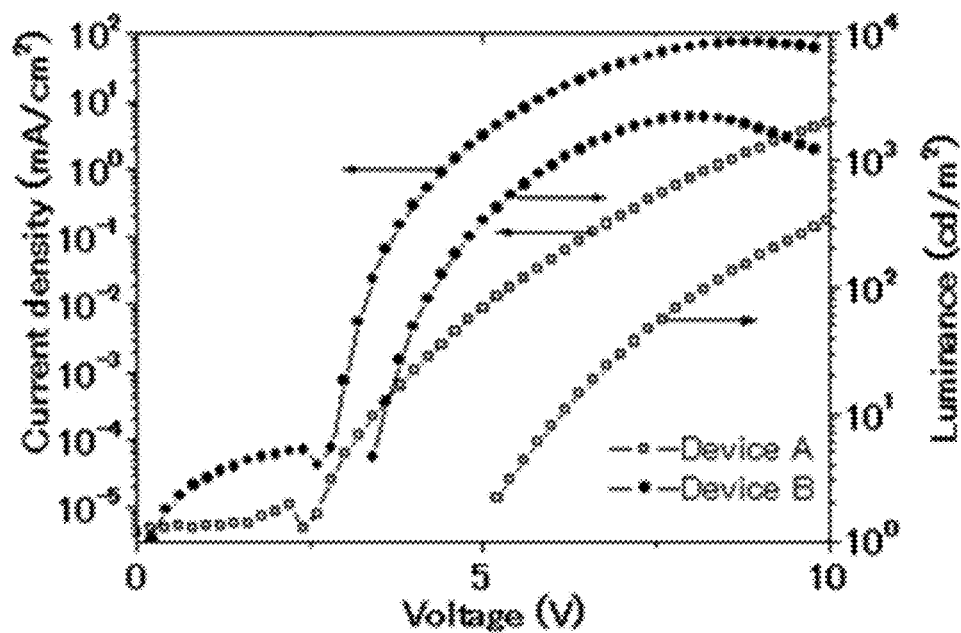
FIG. 19 shows a voltage-current density-emission intensity characteristic of PCz-DCP organic electroluminescence devices (Device B and Device A).
Figure 20:
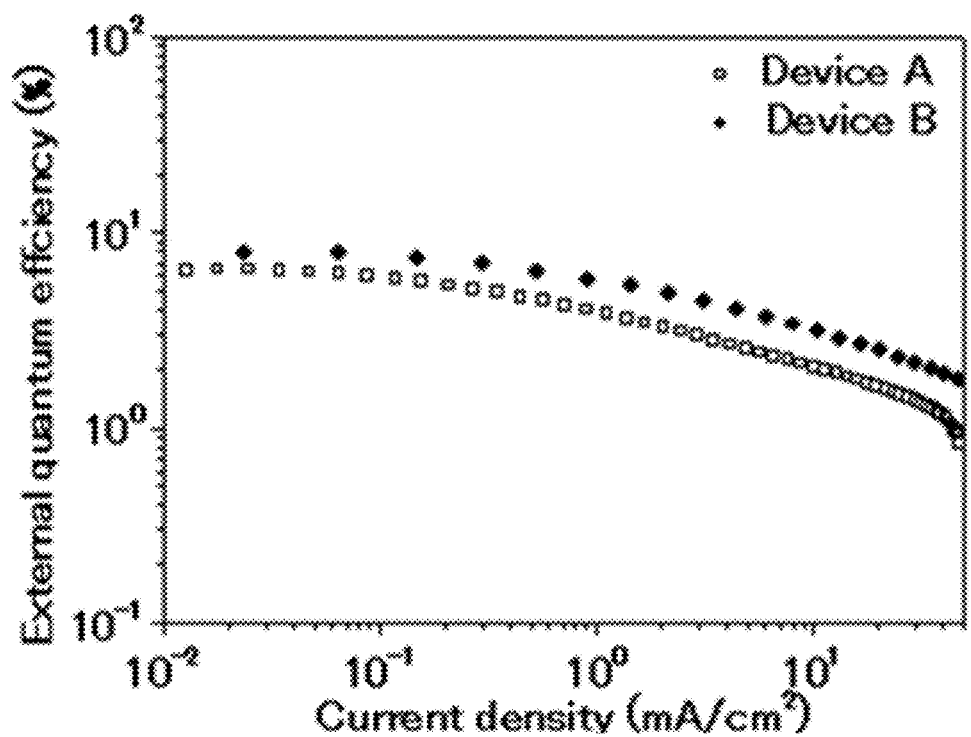
FIG. 20 shows a current density-external quantum efficiency characteristic of PCz-DCP organic electroluminescence devices (Device B and Device A).

Characteristics of the organic electroluminescence device (Device B) were measured. FIG. 18 shows the emission spectrum. As in Example 1, the emission spectrum was in the range of about 500 nm to about 700 nm. FIG. 19 shows the voltage-current density-emission intensity characteristics. The data indicated by the leftward arrow indicates the voltage-current density characteristic, and the data indicated by the rightward arrow indicates the voltage-emission intensity characteristic. FIG. 20 shows the current density-external quantum efficiency characteristic. The maximum external quantum efficiency was 7.8%.

EXAMPLE 5

Figure 17:
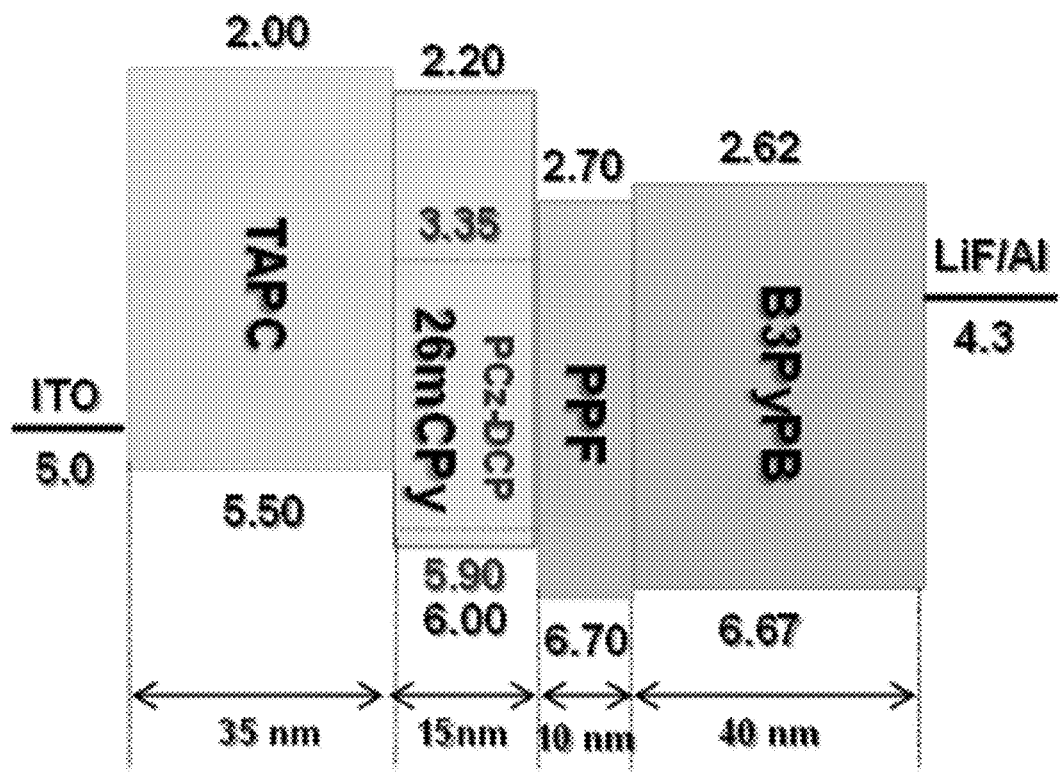
FIG. 17 shows a film configuration of a PCz-DCP organic electroluminescence device (Device A).

An organic electroluminescence device (Device A) was obtained in the same manner as in Example 4 (see FIG. 17) except that 26 mCPy was used instead of CBP.

The characteristics of the organic electroluminescence device (Device A) were measured. FIG. 18 shows the emission spectrum. As in Example 1, the emission spectrum was in the range of about 500 nm to about 700 nm. FIG. 19 shows the voltage-current density-emission intensity characteristics. The data indicated by the leftward arrow indicates the voltage-current density characteristic, and the data indicated by the rightward arrow indicates the voltage-emission intensity characteristic. FIG. 20 shows the current density-external quantum efficiency characteristic. The maximum external quantum efficiency was 6.4%.

[Chemical formula 221]

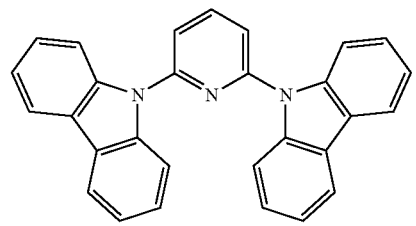

(26mCPy)

EXAMPLE 6

Figure 21:
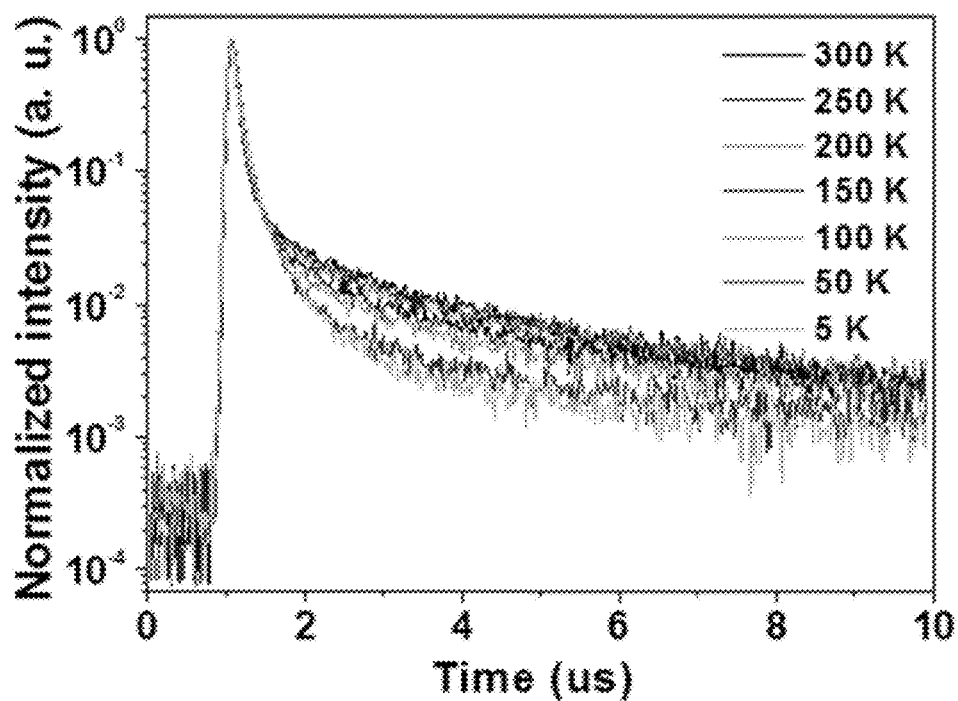
FIG. 21 shows a transient decay curve of PAc-DCP organic photoluminescence device C.

The characteristics were evaluated in the same manner as in Example 4 except that PAc-DCP was used instead of PCz-DCP. In the toluene solution, light emission in the visible region could not be observed. The photoluminescence quantum efficiency was 31.9% in the organic photoluminescence device C. From the transient decay curves, it can be seen that PAc-DCP is a luminescent body ($\tau_{prompt}$=19 nanoseconds, $t_{delayed}$=2.6 microseconds) containing a delay component in addition to the fluorescent component (FIG. 21). Also, since there is a change in the lifetime of the delay component depending on the temperature, it can be seen that PAc-DCP is a thermally activated delayed fluorescent material (TADF).

Figure 22:
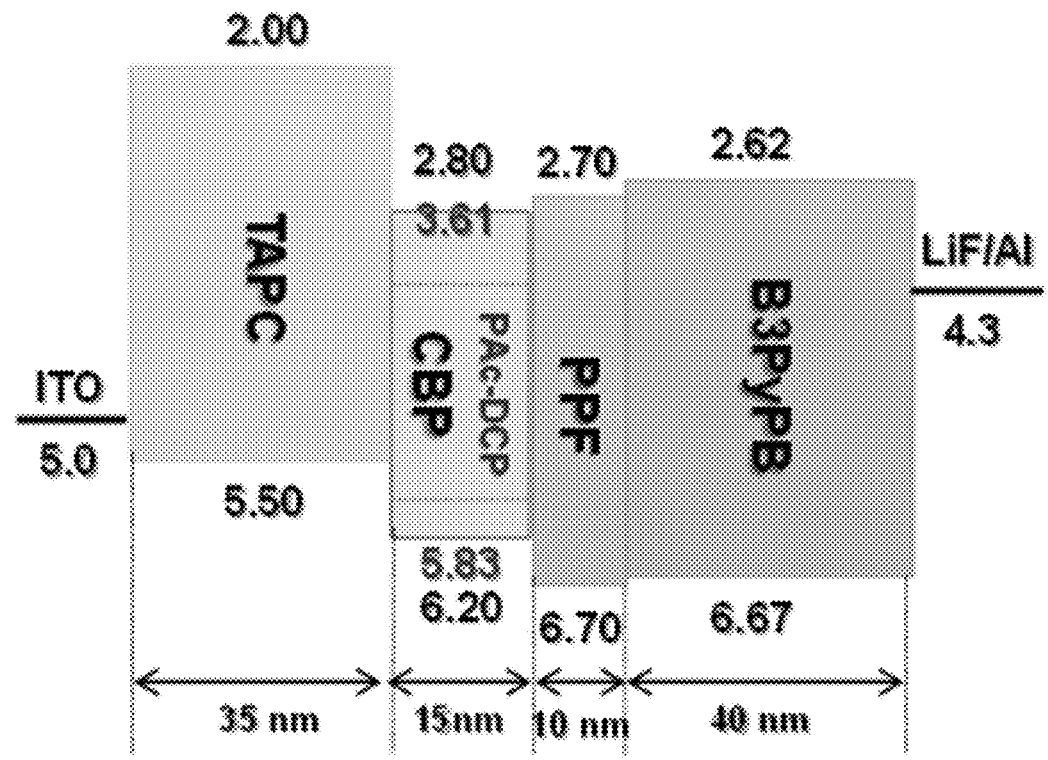
FIG. 22 shows a film configuration of a PAc-DCP organic electroluminescence device (Device B).
Figure 24:
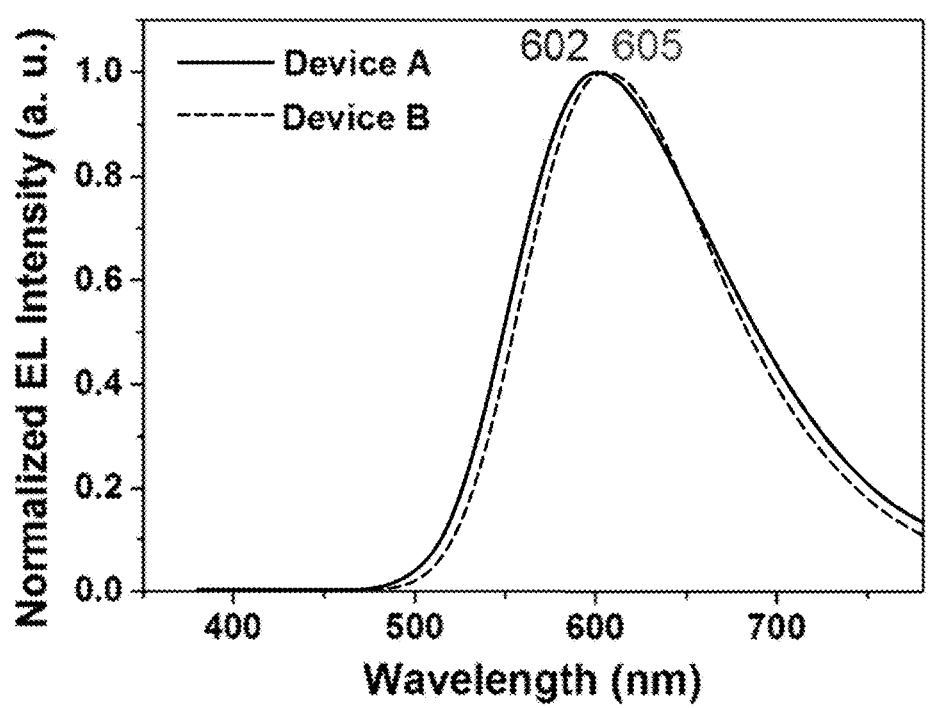
FIG. 24 shows light emission spectrum of PAc-DCP organic electroluminescence devices (Device B and Device A).
Figure 25:
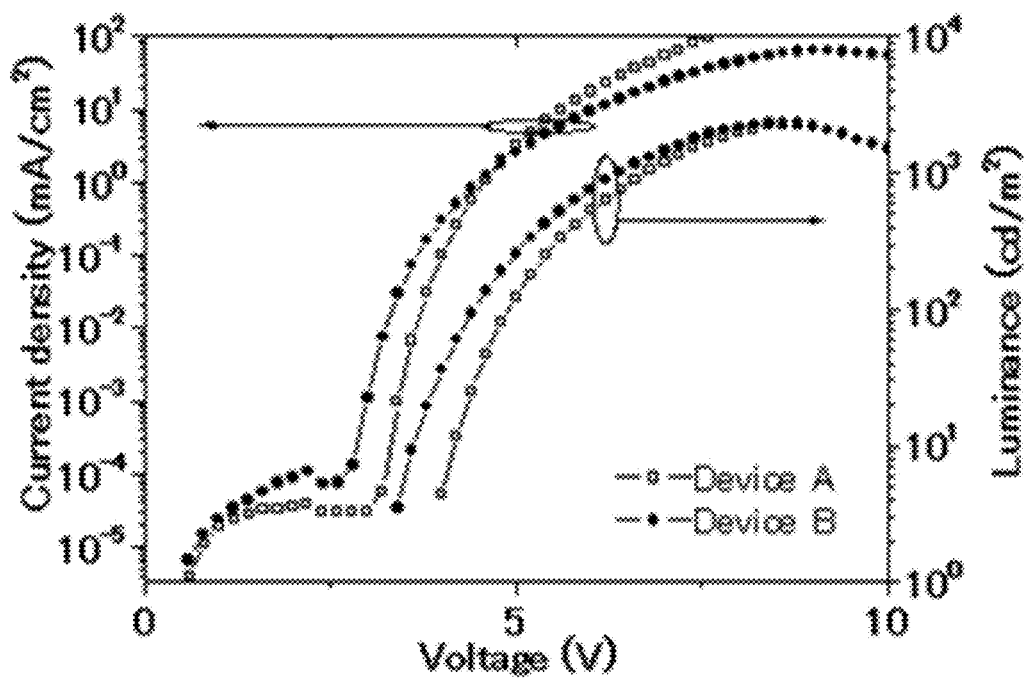
FIG. 25 is shows a voltage-current density-emission intensity characteristic of PAc-DCP organic electroluminescence devices (Device B and Device A).
Figure 26:
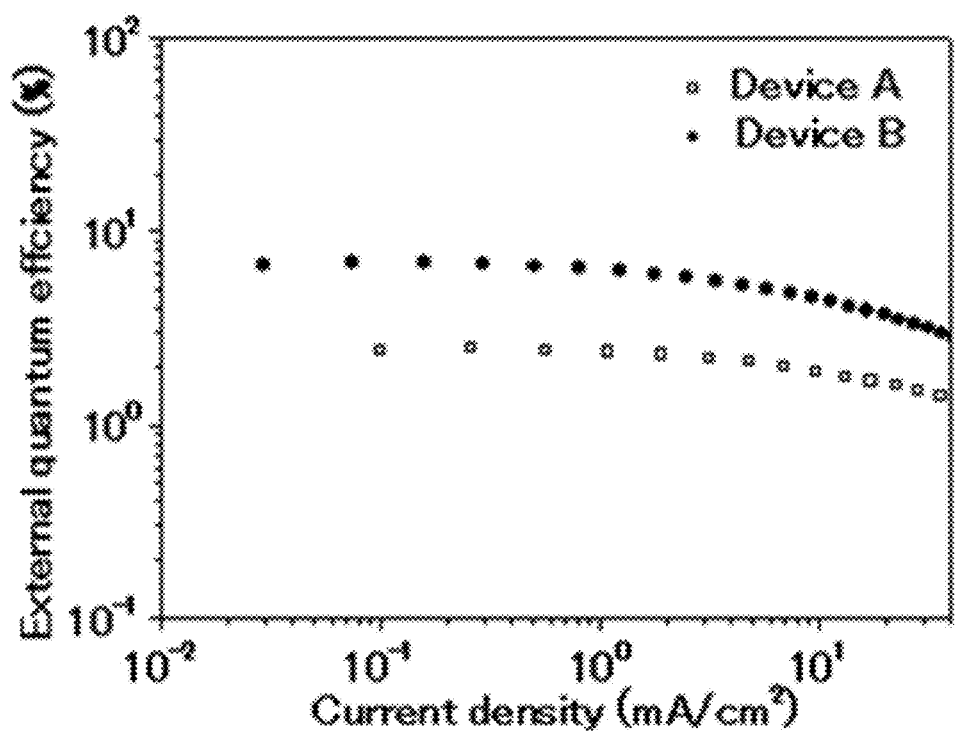
FIG. 26 shows current density-external quantum efficiency characteristic of PAc-DCP organic electroluminescence devices (Device B and Device A).

The characteristics of the organic electroluminescence device (Device B: FIG. 22) were measured. FIG. 24 shows the emission spectrum. As in Example 1, the emission spectrum was in the range of about 500 nm to about 700 nm. FIG. 25 shows voltage-current density-emission intensity characteristics. The data indicated by the leftward arrow indicates the voltage-current density characteristic, and the data indicated by the rightward arrow indicates the voltage-emission intensity characteristic. FIG. 26 shows the current density-external quantum efficiency characteristic. The maximum external quantum efficiency was 6.9%.

[Chemical formula 222]

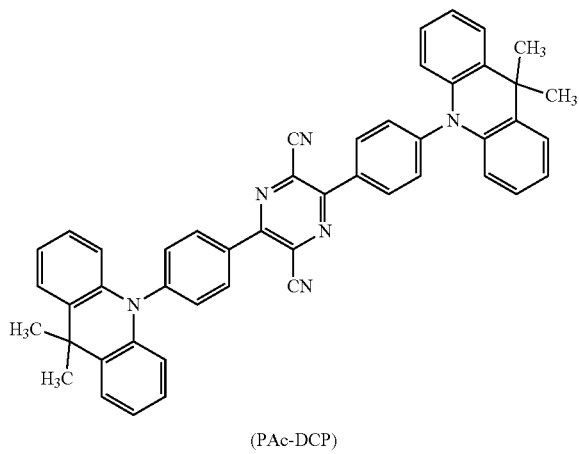

(PAc-DCP)

EXAMPLE 7

Figure 23:
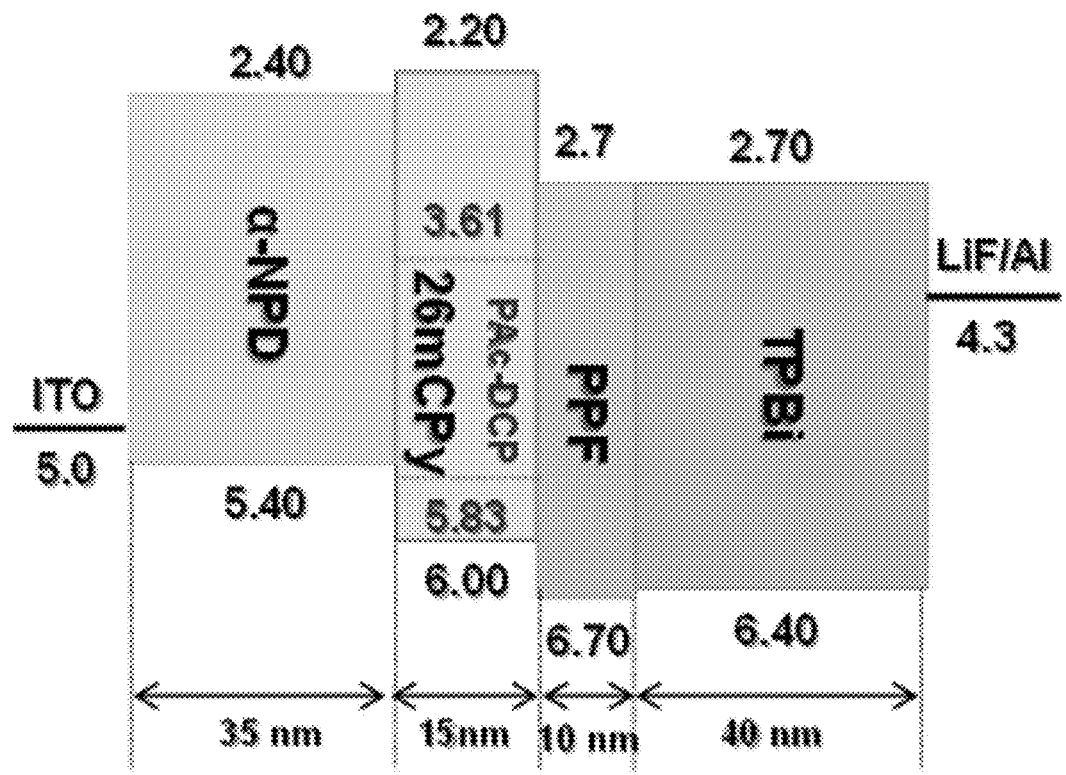
FIG. 23 shows a film configuration of a PAc-DCP organic electroluminescence device (Device A).

An organic electroluminescence device (Device A) was obtained in the same manner as in Example 6 except that α-NPD was used instead of TAPC, 26 mCPy was used instead of CBP, and TPBi was used instead of B3PyPB (see FIG. 23).

The characteristics of the organic electroluminescence device (Device A) were measured. FIG. 24 shows the emission spectrum. As in Example 1, the emission spectrum was in the range of about 500 nm to about 700 nm. FIG. 25 shows voltage-current density-emission intensity characteristics. The data indicated by the leftward arrow indicates the voltage-current density characteristic, and the data indicated by the rightward arrow indicates the voltage-emission intensity characteristic. FIG. 26 shows the current density-external quantum efficiency characteristic. The maximum external quantum efficiency was 2.4%.

A luminescent material obtained by synthesizing a compound having 2,3-dicyanopyrazine as a central skeleton (a compound represented by formula (I)) was found to have a high EL luminescence characteristic by evaluation based on TADF. Moreover, it was able to achieve an EQE value far higher than the theoretical limit value (5%) of the external quantum efficiency (EQE) of ordinary fluorescent molecules. The compound represented by formula (I) is a very promising material as a TADF luminescent material.

A luminescent material obtained by synthesizing a compound represented by formula (II) having 2,5-dicyanopyrazine as a central skeleton was found to have a high EL luminescence characteristic by evaluation based on TADF. In addition, it was able to achieve an EQE value higher than the theoretical limit value (5%) of the external quantum efficiency (EQE) of ordinary fluorescent molecules. The compound represented by formula (II) is a promising material as a TADF luminescent material.

REFERENCE EXAMPLE 400 mg of 2,3-diamino-3-(phenylthio) acrylonitrile was dissolved in 45 ml of 1,2-dimethoxyethane, and the resulting solution was added to a solution containing 150 ml of 0.1 M citric acid-sodium citrate buffer solution (pH=3.0) and 150 ml of water, followed by leaving for 5 hours at room temperature. Red-colored acicular crystals were filtered and washed with 3 ml of n-hexane-ethyl acetate (3:1). 7.5 mg (yield 45%) of 3,6-diamino-2,5-dicyanopyrazine was obtained.

$^{13}$C-NMR (d$_6$-DMSO):149.730, 115.115, 113.251 ppm

EXAMPLE 8

23.73 g (106.2 mmol) of copper (II) bromide and 10.95 g (118.0 mmol) of t-butylnitrite were dissolved in 100 ml of dry acetonitrile. To the resulting solution, 3.40 g (21.2 mmol) of 3,6-diamino-2,5-dicyanopyrazine was gradually added at 60° C. Foaming occurred when 3,6-diamino-2,5-dicyanopyrazine was added. After completion of the addition, the mixture was reacted by stirring at 70° C. for 5 hours (reaction rate: 69.1%). The reaction solution was cooled to room temperature, poured into water, then extracted three times with chloroform, and separated into an organic phase and an aqueous phase. The organic phase was washed with water, then dried over anhydrous sodium sulfate, filtered and concentrated. The crude product was purified by silica gel chromatography and dried under vacuum to obtain 2,5-dicyano-3,6-dibromopyrazine (4.1 g, yield 67.0 mol %)

$^{13}$C-NMR (125 MHz, CDCl$_3$): δ 140.78, 134.25, 112.62.
MS: m/z 287.01[M]$^+$

EXAMPLE 9

52.2 ml of acetonitrile (water content: about 250 ppm) was added to 40.0 g (217.4 mmol) of 3,6-diamino-2,5-dicyanopyrazine and stirred to obtain a homogeneous solution. To this solution, 145.7 (652.3 mmol) of copper (II) bromide was added. Then, while maintaining the solution at 40° C., 87.20 g (101 ml, 761.0 mmol) of t-butyl nitrite with a purity of 90% was added dropwise over 90 minutes. After completion of dropwise addition, reaction was carried out by stirring at 40° C. for 30 minutes (reaction rate (gross yield) of 80.1%). The reaction solution at 40° C. was filtered to remove insoluble matter. The filtrate was poured into water to precipitate the solid at 10° C. and then filtered. The solid content was dissolved in toluene at 40° C. The resulting solution was filtered to remove insoluble matter. The filtrate was concentrated under reduced pressure at 55° C. N-hexane was added dropwise to the concentrate at 25° C., and after completion of the dropwise addition, it was cooled to 10° C. and filtered. Light yellow solid on the filter cloth was dried to obtain 45.34 g (yield (net yield) of 70.3 mol %, purity of 97%) of 2,5-dicyano-3,6-dibromopyrazine.

EXAMPLE 10

68 ml of dry acetonitrile was added to 2.25 g (14.1 mmol) of 3,6-diamino-2,5-dicyanopyrazine, and stirred to obtain a homogeneous solution. To this solution, 15.53 g (69.5 mmol) of copper (II) bromide was added. Then, while the solution at 40° C., a mixture of 8.00 g (9.2 ml, 69.8 mmol) of t-butyl nitrate with a purity of 90% and 9.2 ml of dry acetonitrile was added dropwise over 40 minutes. After completion of dropwise addition, reaction was carried out by stirring at 40° C. for 4 hours (reaction rate (gross yield) of 79.4%). The reaction solution at 40° C. was filtered to remove insoluble matter. The filtrate was poured into water to precipitate the solid at 10° C. and then filtered. The solid content was dissolved in chloroform at 40° C. The resulting solution was filtered to remove insoluble matter. The filtrate was concentrated under reduced pressure at 40° C. N-hexane was added dropwise to the concentrate at 25° C., and after completion of the dropwise addition, it was cooled to 10° C.

and filtered. Light yellow solid on the filter cloth was dried to obtain 2.97 g (yield (net yield) of 72 mol %, purity of 98%) of 2,5-dicyano-3,6-dibromopyrazine.

EXAMPLE 11

60 g of dry acetonitrile was added to 2.0 g (12.5 mmol) of 3,6-diamino-2,5-dicyanopyrazine and stirred to obtain a homogeneous solution. To this solution, 13.96 g (62.5 mmol) of copper (II) bromide was added. Then, while maintaining the solution at 40° C., a mixed solution of an n-butyl nitrite 7.21 g (8.1 ml, 62.9 mmol) with a purity of 90% and 8.1 ml of dry acetonitrile was added dropwise over 85 minutes. After completion of dropwise addition, reaction was carried out by stirring at 40° C. for 2 hours (reaction rate (gross yield) of 79.2%). The reaction solution at 40° C. was filtered to remove insoluble matter. The filtrate was poured into water to precipitate the solid at 10° C. and then filtered. The solid content was dissolved in chloroform at 40° C. The resulting solution was filtered to remove insoluble matter. The filtrate was concentrated under reduced pressure at 40° C. N-hexane was added dropwise to the concentrate at 25° C., and after completion of the dropwise addition, it was cooled to 10° C. and filtered. Light yellow solid on the filter cloth was dried to obtain 2.66 g (yield (net yield) of 69.9 mol %, purity of 94.6%) of 2,5-dicyano-3,6-dibromopyrazine.

EXAMPLE 12

Except that the mixed solution of 7.21 g of n-butyl nitrite with a purity of 90% and 8.1 ml of dry acetonitrile was replaced with a mixed solution of 6.79 g (7.8 ml) of isobutyl nitrite with a purity of 95% and 7.8 ml of dry acetonitrile, 2,5-dicyano-3,6-dibromopyrazine was obtained in the same manner as in Example 4. The reaction rate was 79.5%, the yield was 70.0 mol %, and the purity was 95.4%.

EXAMPLE 13

Except that the mixed solution of 7.21 g of n-butyl nitrite with a purity of 90% and 8.1 ml of dry acetonitrile was replace with a mixed solution of 7.74 g (8.8 ml) of an isoamyl nitrite with a purity of 95% and 8.8 ml of a dry acetonitrile, and the dropwise addition time was changed to 90 minutes, 2,5-dicyano-3,6-dibromopyrazine was obtained in the same manner as in Example 4. The reaction rate was 78.8%, the yield was 69.6 mol %, and the purity was 95.3%.

EXAMPLE 14

Except that the amount of 3,6-diamino-2,5-dicyanopyrazine was changed to 2.0 g, the amount of copper (II) bromide was changed to 13.96 g, the amount of acetonitrile was changed to 60 ml, the amount of t-butyl nitrite with a purity of 90% was changed to 7.13 g, the temperature during the reaction was changed to 30° C., the dropwise addition time was changed to 30 minutes, and the stirring time after completion of the dropwise addition was changed to 4 hours, 2,5-dicyano-3,6-dibromopyrazine was obtained in the same manner as in Example 4. The reaction rate was 76.4%.

EXAMPLE 15

Except that the amount of 3,6-diamino-2,5-dicyanopyrazine was changed to 2.0 g, the amount of copper (II) bromide was changed to 13.98 g, the amount of acetonitrile was changed to 60 ml, the amount of t-butyl nitrite with a purity of 90% was changed to 7.13 g, the temperature during the reaction was changed to 60° C., the dropping time was changed to 20 minutes, and the stirring time after completion of the dropwise addition was changed to 3 hours, 2,5-dicyano-3,6-dibromopyrazine was obtained in the same manner as in Example 4. The reaction rate was 76.3%.

EXAMPLE 16

Except that the amount of 3,6-diamino-2,5-dicyanopyrazine was changed to 2.0 g, the amount of copper (II) bromide was changed to 13.96 g, the amount of acetonitrile was changed to 60 ml, the amount of t-butyl nitrite with a purity of 90% was changed to 7.22 g, the stirring time after completion of the dropwise addition was changed to 3 hours, 2,5-dicyano-3,6-dibromopyrazine was obtained in the same manner as in Example 1. The reaction rate was 72.4%.

EXAMPLE 17

Except that the amount of 3,6-diamino-2,5-dicyanopyrazine was changed to 2.0 the amount of copper (II) bromide was changed to 13.96 g, the amount of acetonitrile was changed to 60 ml, the amount of t-butyl nitrite with a purity of 90% was changed to and stirring after completion of the dropwise addition was not carried out, 2,5-dicyano-3,6-dibromopyrazine was obtained in the same manner as in Example 1. The reaction rate was 77.8%.

INDUSTRIAL APPLICABILITY

The present invention can provide a novel dicyanopyrazine compound and a luminescent material, and can provide a luminescence device using the luminescent material.

In addition, the present invention can provide 2,5-dicyano-3,6-dihalogenopyrazine which is useful for producing a compound containing a dicyanopyrazine skeleton having an electron donating group from an inexpensive starting material in a small reaction step and in a high yield.

The invention claimed is:

1. A method for producing a 2,5-dicyano-3,6-dihalogenopyrazine comprising subjecting a 2,5-dicyano-3,6-diaminopyrazine to a halogenation reaction in a solvent in the presence of nitrous acid or nitrite.

2. The method according to claim 1, wherein a temperature during the halogenation reaction is in a range of from 30 to 60° C.

3. The method according to claim 1, further comprising reacting (2E)-2,3-diamino-3-(substituted sulfanyl)-2-propenenitrile in a solvent in the presence of oxygen under acidic conditions to obtain the 2,5-dicyano-3,6-diaminopyrazine.

4. The method according to claim 3, wherein the (2E)-2, 3-diamino-3-(substituted sulfanyl)-2-propenenitrile is a compound represented by formula (9),

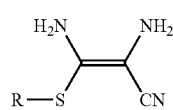

(9)

where R represents a substituted or unsubstituted aryl group, a substituted or unsubstituted alkyl group, a substituted or unsubstituted aralkyl group, or a substituted or unsubstituted alkenyl group.

* * * * *

UNITED STATES PATENT AND TRADEMARK OFFICE
CERTIFICATE OF CORRECTION

PATENT NO. : 10,522,763 B2
APPLICATION NO. : 16/260725
DATED : December 31, 2019
INVENTOR(S) : Takuma Yasuda et al.

Page 1 of 1

It is certified that error appears in the above-identified patent and that said Letters Patent is hereby corrected as shown below:

On the Title Page

Item (73) Assignees, change:
"KYUSHU UNIVERSITY, NATIONAL UNIVERSIT CORPORATION, Fukuoka-shi (JP); NIPPON SODA CO., LTD., Tokyo (JP)"

To read:
--KYUSHU UNIVERSITY, NATIONAL UNIVERSITY CORPORATION, Fukuoka-shi (JP); NIPPON SODA CO., LTD., Tokyo (JP)--

Signed and Sealed this
Seventeenth Day of March, 2020

Andrei Iancu
*Director of the United States Patent and Trademark Office*